US011168370B2

(12) United States Patent
Lo et al.

(10) Patent No.: US 11,168,370 B2
(45) Date of Patent: Nov. 9, 2021

(54) DETECTING MUTATIONS FOR CANCER SCREENING

(71) Applicant: The Chiness University of Hong Kong, Shatin (HK)

(72) Inventors: Yuk-Ming Dennis Lo, Kowloon (HK); Rossa Wai Kwun Chiu, Shatin (HK); Kwan Chee Chan, Shatin (HK); Peiyong Jiang, Shatin (HK)

(73) Assignee: The Chinese University of Hong Kong, New Territories (HK)

( * ) Notice: Subject to any disclaimer, the term of this patent is extended or adjusted under 35 U.S.C. 154(b) by 351 days.

(21) Appl. No.: 16/254,492

(22) Filed: Jan. 22, 2019

(65) Prior Publication Data

US 2019/0153541 A1    May 23, 2019

Related U.S. Application Data

(60) Division of application No. 15/362,631, filed on Nov. 28, 2016, now Pat. No. 10,240,209, which is a continuation of application No. PCT/CN2016/073753, filed on Feb. 14, 2016.

(60) Provisional application No. 62/271,196, filed on Dec. 22, 2015, provisional application No. 62/114,471, filed on Feb. 10, 2015.

(51) Int. Cl.
*C12Q 1/6886* (2018.01)
*G16B 20/00* (2019.01)
*G16B 30/00* (2019.01)
*G16B 30/10* (2019.01)
*G16B 20/20* (2019.01)
*C12Q 1/6806* (2018.01)

(52) U.S. Cl.
CPC ........... *C12Q 1/6886* (2013.01); *G16B 20/00* (2019.02); *G16B 20/20* (2019.02); *G16B 30/00* (2019.02); *G16B 30/10* (2019.02); *C12Q 1/6806* (2013.01); *C12Q 2600/154* (2013.01); *C12Q 2600/156* (2013.01)

(58) Field of Classification Search
CPC ........ G16B 40/00; G16B 20/20; G16B 30/00; G16B 30/10; C12Q 1/6886
USPC .......................................................... 702/19
See application file for complete search history.

(56) References Cited

U.S. PATENT DOCUMENTS

| 7,704,687 | B2 | 4/2010 | Wang et al. |
| 8,741,811 | B2 | 6/2014 | La et al. |
| 10,240,209 | B2 | 3/2019 | Lo et al. |
| 2003/0219765 | A1 | 11/2003 | Costa |
| 2005/0164241 | A1 | 7/2005 | Hahn et al. |
| 2005/0282196 | A1 | 12/2005 | Costa |
| 2007/0122823 | A1 | 5/2007 | Bianchi et al. |
| 2007/0202525 | A1 | 8/2007 | Quake et al. |
| 2009/0029377 | A1 | 1/2009 | Lo et al. |
| 2009/0087847 | A1 | 4/2009 | Lo et al. |
| 2010/0041048 | A1 | 2/2010 | Diehl et al. |
| 2010/0112575 | A1 | 5/2010 | Fan et al. |
| 2010/0136560 | A1 | 6/2010 | Vogelstein et al. |
| 2013/0040824 | A1 | 2/2013 | Lo et al. |
| 2013/0237431 | A1 | 9/2013 | Lo et al. |
| 2014/0080715 | A1 | 3/2014 | Lo et al. |
| 2014/0100121 | A1 | 4/2014 | Lo et al. |
| 2014/0274740 | A1 | 9/2014 | Srinivasan et al. |
| 2015/0011403 | A1 | 1/2015 | Lo et al. |
| 2015/0087529 | A1 | 3/2015 | Lo et al. |
| 2016/0002717 | A1 | 1/2016 | Lee et al. |
| 2016/0333416 | A1 | 11/2016 | Babiarz et al. |
| 2017/0211143 | A1 | 7/2017 | Shendure et al. |
| 2017/0260590 | A1 | 9/2017 | Eltoukhy et al. |
| 2017/0321284 | A1 | 11/2017 | McCarroll et al. |
| 2017/0356053 | A1 | 12/2017 | Otto et al. |
| 2018/0119230 | A1 | 5/2018 | Velculescu et al. |

FOREIGN PATENT DOCUMENTS

| AU | 2013278994 | | 7/2017 |
| CN | 104781422 | A | 7/2015 |
| CN | 104662168 | | 12/2017 |
| EA | 005140 | B1 | 12/2004 |
| EA | 010571 | B1 | 10/2008 |
| EA | 011608 | B1 | 4/2009 |

(Continued)

OTHER PUBLICATIONS

English translation of Office Action dated Jul. 1, 2020 in KR Patent Application No. 10-2020-7009028. 5 pages.

(Continued)

*Primary Examiner* — Jerry Lin

(74) *Attorney, Agent, or Firm* — Kilpatrick Townsend & Stockton LLP

(57) ABSTRACT

Embodiments are related to the accurate detection of somatic mutations in the plasma (or other samples containing cell-free DNA) of cancer patients and for subjects being screened for cancer. The detection of these molecular markers would be useful for the screening, detection, monitoring, management, and prognostication of cancer patients. For example, a mutational load can be determined from the identified somatic mutations, and the mutational load can be used to screen for any or various types of cancers, where no prior knowledge about a tumor or possible cancer of the subject may be required. Embodiments can be useful for guiding the use of therapies (e.g. targeted therapy, immunotherapy, genome editing, surgery, chemotherapy, embolization therapy, anti-angiogenesis therapy) for cancers. Embodiments are also directed to identifying de novo mutations in a fetus by analyzing a maternal sample having cell-free DNA from the fetus.

27 Claims, 50 Drawing Sheets

(56) References Cited

FOREIGN PATENT DOCUMENTS

| | | |
|---|---|---|
| EA | 018444 B1 | 8/2013 |
| EP | 2426217 A1 | 3/2012 |
| EP | 2864501 | 4/2015 |
| EP | 2864501 | 8/2018 |
| GB | 2485635 A | 5/2012 |
| HK | 1205533 | 6/2018 |
| JP | 2005514956 A | 5/2005 |
| JP | 2010534068 A | 11/2010 |
| JP | 2010534069 A | 11/2010 |
| JP | 2013509884 A | 3/2013 |
| JP | 2014534507 A | 12/2014 |
| JP | 2015527057 | 9/2015 |
| JP | 6371280 | 7/2018 |
| KR | 101884909 | 7/2018 |
| MX | 360264 | 10/2018 |
| SG | 11201408113Q | 9/2018 |
| TW | 201122470 A | 7/2011 |
| TW | 201403066 | 1/2014 |
| TW | I636255 | 9/2018 |
| WO | 2000/061612 A2 | 10/2000 |
| WO | 03062441 A1 | 7/2003 |
| WO | 2004/078999 A1 | 9/2004 |
| WO | 2004/111272 A2 | 12/2004 |
| WO | 2007/028155 A2 | 3/2007 |
| WO | 2007/100911 A2 | 9/2007 |
| WO | 2008/024009 A1 | 2/2008 |
| WO | 2008/146309 A2 | 12/2008 |
| WO | 2009/013492 A1 | 1/2009 |
| WO | 2009/013496 A1 | 1/2009 |
| WO | 2009/019455 A2 | 2/2009 |
| WO | 2010/112316 A1 | 10/2010 |
| WO | 2011038507 A1 | 4/2011 |
| WO | 2011/053790 A2 | 5/2011 |
| WO | 2011/054936 A1 | 5/2011 |
| WO | 2011057094 A1 | 5/2011 |
| WO | 2011/073665 A1 | 6/2011 |
| WO | 2011/090557 A1 | 7/2011 |
| WO | 2011/091046 A1 | 7/2011 |
| WO | 2011/103236 A2 | 8/2011 |
| WO | 2012/071621 A1 | 6/2012 |
| WO | 2013052913 A2 | 4/2013 |
| WO | 2013/086352 A1 | 6/2013 |
| WO | 2013/138510 A1 | 9/2013 |
| WO | 2014/039556 A1 | 3/2014 |
| WO | 2014043763 A1 | 3/2014 |
| WO | 2014/130890 A1 | 8/2014 |
| WO | 2016/015058 A2 | 1/2016 |
| ZA | 201409281 | 8/2017 |

OTHER PUBLICATIONS

English translation of Office Action dated Jul. 31, 2020 in TW Patent Application No. 105123553. 3 pages.
English translation of Office Action dated Aug. 25, 2020 in JP Patent Application No. 2018-503181. 6 pages.
Chandrananda, Dineika et al.; "High-resolution characterization of sequence signatures due to non-random cleavage of cell-free DNA"; BMC Medical Genomics; 2015; vol. 8, No. 29; 19 pages.
English translation of Search Report dated Aug. 31, 2020 in TW Patent Application No. 105104407. 2 pages.
Non-Final Office Action dated Sep. 3, 2020 in U.S. Appl. No. 13/801,748, filed Mar. 13, 2013. 20 pages.
English translation of Office Action dated Sep. 17, 2019 in JP Patent Application No. 2018-132118. 6 pages.
English translation of Office Action dated Jan. 7, 2020 in JP Patent Application No. 2017-559756. 6 pages.
Communication pursuant to Aritcle 94(3) EPC dated Feb. 7, 2020 in EP Patent Application 18185290.6. 5 pages.
English translation of Office Action and Search Report dated Feb. 14, 2020 in TW Patent Application No. 107128593. 5 pages.
Office Action dated Feb. 8, 2019, from Canadian Patent Application No. 2,876,327, 4 pages.
Final Notice of Office Action, and English translation thereof, dated Mar. 22, 2019, from Korean Patent Application No. 10-2018-7021883, filed Jul. 27, 2018, 13 pages.
Non-Final Office Action, U.S. Appl. No. 15/362,631, dated Jan. 11, 2018, 6 pages.
Lun, Fiona M. F., et al., "Noninvasive prenatal diagnosis of monogenic diseases by digital size selection and relative mutation dosage on DNA in maternal plasma;" Dec. 16, 2008; PNAS; vol. 105; No. 50; pp. 19920-19925.
Diehl, Frank, et al., "Detection and quantification of mutations in the plasma of patients with colorectal tumors;" Nov. 8, 2005; PNAS; vol. 102; No. 45; pp. 16368-16373.
Fan, H. Christina et al.; "Analysis of the Size Distributions of Fetal and Maternal Cell-Free DNA by Paired-End Sequencing"; Clinical Chemistry; 2010; 56:8; pp. 1279-1286.
Yu, Stephanie C. Y. et al.; "Size-based molecular diagnostics using plasma DNA for noninvasive prenatal testing"; PNAS; 2014; vol. 111, No. 23; pp. 8583-8588.
Chan, K.C. Allen et al.; "Molecular Characterization of Circulating EBV DNA in the Plasma of Nasopharyngeal Carcinoma and Lymphoma Patients"; Cancer Research; 2003; 63; pp. 2028-2032.
Ellinger, Jörg et al.; "Cell-Free Circulating DNA: Diagnostic Value in Patients With Testicular Germ Cell Cancer"; the Journal of Urology; 2009; vol. 181, pp. 363-371.
International Search Report and Written Opinion dated Jun. 18, 2013 in International Application No. PCT/IB2013/000312. 13 pages.
Lo., Y.M. Dennis et al.; "Maternal Plasma DNA Sequencing Reveals the Genome-Wide Genetic and Mutational Profile of the Fetus"; Science Translational Medicine; 2010; vol. 2, Issue 61; 14 pages; retrieved from the internet URL: www.stm.sciencemag.org.
Fan, H. Christina et al.; "Detection of Aneuploidy with Digital Polymerase Chain Reaction"; Analytical Chemistry; 2007; vol. 79, No. 19; pp. 7576-7579.
Chan, K.C. Allen et al.; "Size Distributions of Maternal and Fetal DNA in Maternal Plasma"; Clinical Chemistry; 2004; 50:1; pp. 88-92.
Ding, Chunming et al.; "MS analysis of single-nucleotide differences in circulating nucleic acids: Application to noninvasive prenatal diagnosis"; PNAS; 2004; vol. 101, No. 29; pp. 10762-10767.
Reed, W. et al.; "Non-invasive determination of the paternal HLA haplotype of a fetus using kinetic PCR to detect fetal microchimerism in maternal plasma"; Bone Marrow Transplantation; 2002; 29; pp. 527-529.
Chiu, Rossa W.K. et al.; "Non-invasive prenatal diagnosis by single molecule counting technologies"; Trends in Genetics; 2009; vol. 25, No. 7; pp. 324-331.
Fan, H. Christina et al.; "Noninvasive diagnosis of fetal aneuploidy by shotgun sequencing DNA from maternal blood"; PNAS; 2008; vol. 105, No. 42; pp. 16266-16271.
Chid, Rossa W.K. et al.; "Noninvasive prenatal diagnosis of fetal chromosomal aneupoloidy by massively parallel genomic sequencing of DNA in maternal plasma"; PNAS; 2008; vol. 105, No. 51; pp. 20458-20463.
Larrabee, Paige B. et al.; "Microarray Analysis of Cell-Free Fetal DNA in Amniotic Fluid: a Prental Molecular Karyotype"; the American Journal of Human Genetics; 2004; 75; pp. 485-491.
Li, Ying et al.; "Size Separation of Circulatory DNA in Maternal Plasma Permits Ready Detection of Fetal DNA Polymorphisms"; Clinical Chemistry; 2004; 50:6; pp. 1002-1011.
Lo, Y.M. Dennis et al.; "Digital PCR for the molecular detection of fetal chromosomal aneuploidy"; PNAS; 2007; vol. 104, No. 32, pp. 13116-13121.
Peter, Inga et al.; "Cell-free DNA Fragmentation Patterns in Amniotic Fluid Identify Genetic Abnormalities and Changes due to Storage"; Diagnostic Molecular Pathology; 2008; pp. 185-190.
Lapaire, Olav et al.; "Larger Columns and Change of Lysis Buffer Increase the Yield of Cell-Free DNA Extracted from Amniotic Fluid"; Letters to the Editor, Clinical Chemistry; 2006; 52:1; pp. 156-157.
Lapaire, Olav et al.; "Cell-Free Fetal DNA in Amniotic Fluid: Unique Fragmentation Signatures in Euploid and Aneuploid Fetuses"; Clinical Chemistry; 2007; 53:3; pp. 405-411.

(56) References Cited

OTHER PUBLICATIONS

Lapaire, Olav et al.; "Array-CGH analysis of cell-free fetal DNA in 10mL of amniotic fluid supernatant"; Prenatal Diagnosis; 2007; 27; pp. 616-621.
Bianchi, Diana W. et al.; "Large Amounts of Cell-free Fetal DNA Are Present in Amniotic Fluid"; Clinical Chemistry; 2001; 47:10; pp. 1867-1869.
Lecoeur, Hervé; "Nuclear Apoptosis Detection by Flow Cytometry: Influence of Endogenous Endonucleases"; Experimental Cell Research; 2002; 277; pp. 1-14.
Jiang, Wei-Wen et al.; "Increased plasma DNA integrity index in head and neck cancer patients"; International Journal of Cancer; 2006; 119; pp. 2673-2676.
Zheng, Yama W.L. et al.; "Nonhematopoietically Derived DNA is Shorter than Hematopoietically Dervied DNA in Plasma: A Transplantation Model"; Clinical Chemistry; 2012; 58:3; pp. 549-558.
Jahr, Sabine et al.; "DNA Fragments in the Blood Plasma of Cancer Patients: Quantitations and Evidence for Their Origin from Apoptotic and Necrotic Cells"; Cancer Research; 2001; 61; pp. 1659-1665.
Final Office Action, U.S. Appl. No. 13/801,748 dated Apr. 25, 2019, 14 pages.
Final Office Action, U.S. Appl. No. 13/801,748, dated Oct. 3, 2016, 12 pages.
Final Office Action, U.S. Appl. No. 13/801,748, dated Apr. 6, 2018, pp. 1-26.
Non-Final Office Action, U.S. Appl. No. 13/801,748, dated Oct. 19, 2018, 14 pages.
Non-Final Office Action, U.S. Appl. No. 13/801,748, dated Jan. 22, 2016, pp. 1-16.
Non-Final Office Action, U.S. Appl. No. 13/801,748, dated Aug. 11, 2017, pp. 1-21.
Advisory Action U.S. Appl. No. 13/801,748, dated Feb. 24, 2017, 3 pages.
International Search Report and Written Opinion dated Apr. 20, 2011 in International Application No. PCT/US2010/055655. 20 pages.
International Search Report and Written Opinion dated Feb. 23, 2011 in International Application No. PCT/EP2010/066935. 13 pages.
Kitzman, Jacob O. et al.; "Noninvasive Whole-Genome Sequencing of a Human Fetus"; Science Translational Medicine; Jun. 6, 2012; vol. 4, Issue 137; 137ra76; 19 pages.
Snyder, Matthew W. et al.; "Cell-free DNA Comprises an in Vivo Nucleosome Footprint that Informs Its Tissues-Of-Origin"; Cell; Jan. 14, 2016; 164: 57-68 (30 pages).
"TruSeq DNA PCR-Free Sample Preparation Kit"; Data Sheet: Sequencing [online]; © 2013 Illumina, Inc.; Retrieved from the internet : <URL: http://www.illumina.com/content/dam/illumina-marketing/documents/products/datasheets/datasheet_truseq_dna_pcr_free_sample_prep.pdf> [retrieved on Dec. 7, 2016]; 4 pages.
International Search Report dated Jan. 12, 2016 in International Application No. PCT/US2015/042310. 4 pages.
Tao, el al., "Rapid growth of a hepatocellular carcinoma and the driving mutations revealed by cell-population genetic analysis of whole-genome data," PNAS, 2011, vol. 108, No. 29, pp. 12042-12047.
Chan, K.C.A., et al., "Cancer genome scanning in plasma: detection of tumor-associated copy number aberrations, single-nucleotide variants, and tumoral heterogeneity by massively parallel sequencing," Clinical Chemistry, 2013, vol. 59, No. 1, pp. 211-224.
Chan, K.C.A., et al., "Noninvasive detection of cancer-associated genome-wide hypomethylation and copy number aberrations by plasma DNA bisulfate sequencing," PNAS, Nov. 19, 2013, vol. 110, No. 47, pp. 18761-18768.
Xie, C., et al., "CNV-seq, a new method to detect copy number variation using high-throughput sequencing," BMC Bioinformatics, 2009, vol. 10, No. 30, 9 pages.
Fan, et al., "Whole-Genome Molecular Haplolyping of Single Cells," Nature Biotechnology; vol. 29, No. 1 Jan. 2011; pp. 51-57 (9 pages).

Forshew, et al., "Noninvasive identification and Monitoring of Cancer Mutations by Targeted Deep Sequencing of Plasma DNA," Science Translational Medicine, May 30, 2012, vol. 4, Issue 136, 13 pages.
Mouliere el al., "High Fragmentation Characterizes Tumour-Derived Circulating DNA," PLoS One, Sep. 2011, vol. 6, Issue 9; 10 pages.
Su et al., "inferring Combined CNV/SNP Haplotypes from Genotype Data," Bioinformatics, 2010, vol. 26, No. 11, pp. 1437-1445.
Meyerson, Matthew et al.; "Advances in understanding cancer genomes through second-generation sequencing"; Nature Reviews | Genetics; Oct. 2010; vol. 11; pp. 685-696.
Nannya, Yasuhito, et al.; "A Robust Algorithm for Copy Number Detection Using High-Density Oligonucleotide Single Nucleotide Polymorphism Genotyping Arrays"; Cancer Research; Jul. 15, 2005; 65: (14); pp. 6071-6079.
Palomaki, Glenn E. et al.; "DNA sequencing of maternal plasma to detect Down syndrome: An international clinical validation study"; Genetics in Medicine; Nov. 2011; vol. 13, No. 11; pp. 913-920 and online material appendices (73 pages).
Stratton, Michael R. et al.; "The cancer genome"; Nature; Apr. 9, 2009; vol. 458; doi:10.1038/nature07943; pp. 719-724.
Daniels, Melissa et al.; "Whole genome sequencing for lung cancer"; Journal of Thoracic Disease; Apr. 2012; vol. 4, No. 2; pp. 155-163.
Aird, Daniel et al.; "Analyzing and minimizing PCR amplification bias in Illumina sequencing libraries"; Genome Biology; 2011; 12:R18; http://genomebiology.com/2011/12/2/R18; 14 pages.
Beck, et al., "Next Generation Sequencing of Serum Circulating Nucleic Acids from Patients with Invasive Ductal Breast Cancer Reveals Differences to Health and Nonmalilgnant Controls", American Assoc for Cancer Res , 2010 , 335-342.
Beck, et al., "Profile of the Circulating DNA in Apparently Healthy Individuals", Clinical Chemistry, vol. 55, No. 4, 2009, 730-738.
Chang, et al., "Assessment of Plasma DNA Levels, Allelic Imbalance, and CA 125 as Diagnostic Tests for Cancer", Journal of the National Cancer institute, vol. 94, No. 22, Nov. 20, 2002, 1697-1703.
Diaz, et al., "Supplemental Information", Nature, 2012, 25 pages.
Diaz, et al., "The Molecular Evolution of Acquired Resistance to Targeted EGFR Blockade in Colorectal Cancers", Nature, Jun. 28, 2012, 486(7404), pp. 537-540.
Diehl, et al., "Circulating mutant DNA to assess tumor dynamics", Nature Medicine, published online Jul. 31, 2008, 1-6.
Gerlinger , et al., "Intraturnor heterogeneity and branched evolution revealed by multiregion sequencing", the New England Journal of Medicine, vol. 366, 2012, 883-892.
Hanlon, et al., "Evaluation of 13q14 Status in Multiple Myeloma by Digital Single Nucleotide Polymorphism Technology", Journal of Molecular Diagnostics, vol. 11, No. 5, Sep. 2009, 450-457.
Hou, et al., "Single-Cell Exome Sequencing and Monoclonal Evolution of a JAK2-Negative Myeloproliferative Neoplasm", Cell, Mar. 2, 2012, pp. 873-885.
Jacobs, Kevin B. et al; "Detectable Clonal Mosaicism and its Relationship to Aging and Cancer", Nature Genetics, vol. 44, No. 6, Jun. 2012, pp. 651-653.
Jung, et al., "Cell-free DNA in the blood as a solid tumor biomarker—A critical appraisal of the literature", Clinica Chimica Acta, vol. 411, 2010, 1611-1624.
Karlsson, et al., "Amplification-free sequencing of cell-free DNA for prenatal non-invasive diagnosis of chromosomal aberrations," Genomics 105 (2015), 150-158. (from WOR SG 1056045).
Kinde, Isaac et al.; "Detection and quantification of rare mutations with massively parallel sequencing"; Jun. 7, 2011; PNAS; vol. 108, No. 23; pp. 9530-9535.
Kozarewa, Iwanka et al.; "Amplification-free Illumina sequencing-library preparation facilitates improved mapping and assembly of (G+C)-biased genomes"; Nature Methods; Apr. 2009; vol. 6, No. 4; pp. 291-295.
Lafambroise, et al., "Allele-Specific Amplification in Cancer Revealed by SNP Array Analysis", PLoS Computational Biology; vol. 1, Issue 6, 2005, 0507-0517.

(56) References Cited

OTHER PUBLICATIONS

Leary, et al., "Detection of Chromosomal Alterations in the Circulation of Cancer Patients with Whole-Genome Sequencing", Sci Transl Med, vol. 4, No. 162, 21 pages, Nov. 28, 2012.

Leary, et al., "Development of Personalized Tumor Biomarkers Using Massively Parallel Sequencing", www.ScienceTranslataionalMedicine.org. vol. 2, Issue 20, Feb. 24, 2010, 8 pages.

Leary, "Supplementary Materials for Detection of Chromosomal Alterations in the Circulation of Cancer Patients with Whole-Genome Sequencing", Science Translational Medicine 4, Nov. 28, 2012, 9 pages.

Liao, et al., "Targeted Massively Parallel Sequencing of Maternal Plasma DNA Permits Efficient and Unbiased Detection of Fetal Alleles", Clinical Chemistry, vol. 57, No. 1, 2011, 92-101.

Longo, Dan L., "Tumor Heterogeneity and Personalized Medicine", the New England Journal of Medicine, [online], retrieved from the internet URL: www.nejm.org, Mar. 8, 2012, 2 pages.

McDermott, et al., "Genomics and the Continuum of Cancer Care", the New England Journal of Medicine, Jan. 27, 2011, 340-350.

Miller, et al., "Genome-wide molecular characterization of central nervous system primitive neuroectodermal tumor and pineoblastoma", Neuro-Oncology; 13(8), 2011, 866-879.

Müller, et al., "Identification of Loss of Heterozygosity on Circulating Free DNA in Peripheral Blood of Prostate Cancer Patients: Potential and Technical Improvements", Clinical Chemistry, vol. 54(4); 2008; 688-696.

Murtaza, et al., "Non-invasive analysis of acquired resistance to cancer therapy by sequencing of plasma DNA", Nature May 2, 2013; 497(7447), 108-112.

Navin, et al., "Future Medical Applications of Single-Cell Sequencing in Cancer", Genome Medicine, vol. 3, No. 31, 2011.

Navin, et al., "Tumour Evolution Inferred by Single-Cell Sequencing", Nature, vol. 472, Apr. 7, 2011, 6 pages.

Pennisi, E., "Single-Cell Sequencing Tackles Basic and Biomedical Questions", Science, vol. 336, May 25, 2012, 2 pages.

Prokunina-Olsson, "Cancer Sequencing Gets a Little More Personal", www.ScienceTranslationalMedicine.org; vol. 2; Issue 20, Feb. 24, 2010, pp. 1-3.

Psifidi, et al., "Novel Quantitative Real-Time LCR for the Sensitive Detection of SNP Frequencies in Pooled DNA: Method Development, Evaluation and Application", PLoS One, vol. 6, Issue 1, Jan. 1, 2011, 1-11.

Qin, et al., "Studying copy number variations using a nanofluidic platform", Nucleic Acids Research, vol. 36, No. 18, 2008, 1-8.

Razavi, et al., "Cell-free DNA (cfDNA) mutations from clonal hemalopoiesis: Implications for interpretation of liquid biopsy tests", GRAIL-MSK WBC Poster, ASCO , Jun. 2017 , 1 page.

Razavi, et al., "Performance of a high-intensity 508-gene circulating-tumor DNA (ctDNA) assay in patients with metastatic breast, lung, and prostate cancer", GRAIL-MSK concordance Poster, ASCO, Jun. 2017, 1 page.

Salani, et al., "Measurement of Cyclin E Genomic Copy Number and Strand Length in Cell-Free DNA Distinguish Malignant versus Benign Effusions", Clinical Cancer Research, vol. 13, Oct. 1, 2007, 5805-5809.

Schwarzenbach, Heidi, et al., "Cell-free nucleic acids as biomarkers in cancer patients", Nature Reviews Cancer: Advance Online Publication (AOP) , pp. 426-437.

Shaw, et al., "Genomic analysis of circulating cell free DNA infers breast cancer dormancy", Genome Research; 13 pages, Oct. 11, 2011.

Snyder, et al., "Universal noninvasive detection of solid organ transplant rejection", PNAS, vol. 103, No. 15, Apr. 12, 2011, 6229-6234.

Snyder, et al., "Noninvasive fetal genome sequencing: a primer," Prenat Diagn. Jun. 2013, 33(6), 547-554. [from WOR SG 1056045].

Stratton, "Exploring the Genomes of Cancer Cells: Progress and Promise", Science, Mar. 25, 2011, 1553-1558.

Taback, et al., "Prognostic Significance of Circulating Microsatellite Markers in the Plasma of Melanoma Patients", Cancer Research, vol. 61, Aug. 1, 2001, 5723-5726.

Therry, et al., "Origin and Quantification of Circulating DNA in Mice with Human Colorectal Cancer Xenografts", NAR, vol. 38, No. 18, 2010, 6159-6175.

Van Dijk, Erwin L. et al.; "Library preparation methods for next-generation sequencing: Tone down the bias"; Experimental Cell Research; 2014; vol. 322; http://dx.doi.org/10.1016/j.yexcr.2014.01.008; pp. 12-20.

Wang, et al., "Digital Karyotyping", PNAS, vol. 99, No. 25, Dec. 10, 2002, 16156-16161.

Weber, et al., "Detection of human tumor cells by amplicon fusion site polymerase chain reaction (AFS-PCR)", Journal of Clinical Investigation, vol. 121, No. 2, 2011, 545-553.

Welch, et al. , "The Origin and Evolution of Mutations in Acute Myeloid Leukemia", Cell, 150, Jul. 20, 2012, pp. 264-278.

Xu, et al., "Single-Cell Exome Sequencing Reveals Single-Nucleotide Mutation Characteristics of a Kidney Tumor", Cell, 148, Mar. 2, 2012, pp. 886-895.

Yap, et al., "Intratumor Heterogeneity: Seeing the Wood for the Trees", ScienceTranslationalMedicine, vol. 4, Issue 127, [online], retrieved from the internet URL: www.sciencetranslationalmedicine.org, Mar. 28, 2012, 4 pages.

Yung, et al., "Single-Molecule Detection of Epidermal Growth Factor Receptor Mutations in Plasma by Microfluidics Digital PCR in Non-Small Cell Lung Cancer Patients", Clin Cancer Res, vol. 15, No. 6, Mar. 15, 2009, 2076-2084.

Zhao, et al., "Homozygous Deletions and Chromosome Amplifications in Human Lung Carcinomas Revealed by Single Nucleotide Polymorphism Array Analysis", Cancer Research, 65(13), 2005, 5561-5570.

"Communication pursuant to Article 94(3) EPC dated Feb. 27, 2017 in EP Patent Application No. 13807105.5, 10 pages", dated Feb. 27, 2017.

"English translation of Office Action", mailed in JP Patent Application No. 2015-517896, dated Jul. 26, 2016, 11 pages.

"English translation of Office Action", received in KR Patent Application 10-2015-7001225, dated Oct. 25, 2016, 8 pages.

"English translation of Office Action dated Aug. 14, 2017 in IL Patent Application No. 235967, 4 pages", dated Aug. 14, 2017.

"English translation of Office Action dated Feb. 8, 2017 in TW Patent Application No. 102122036, 3 pages", Feb. 8, 2017.

"Examination Report No. 1" , received in AU Patent Application No. 2013278994, dated Aug. 17, 2016, 3 pages.

"International Search Report and Written Opinion", International Application No. PCT/AU2011 /001562, dated Feb. 17, 2012, 8 pages.

"International Search Report received for PCT Application No. PCT/IB2013/054898", dated Dec. 23, 2013, 17 pages.

"Office Action", CA Patent Application No. 2,876,327, 4 pages, dated Jul. 7, 2017.

English translation of Official Notification dated Mar. 10, 2017 in EA Patent Application No. 201500027, with English translation, 21 pages, dated Mar. 10, 2017.

"Extended European Search Report", issued for EP Application No. 13807105.5, dated Feb. 15, 2016, 11 pages.

"Written Opinion", SG Patent Application No. 11201403113Q, 8 pages, dated Aug. 16, 2017.

"Written Opinion", SG Patent Application No. 11201706529T, 8 pages, dated Jun. 26, 2018.

Cibulskis, et al., "Sensitive detection of somatic point mutations in impure and Heterogeneous cancer samples," Nature Biotechnology 2013, vol. 31, No. 3, pp. 213-221.

Goode, et al., "A simple consensus approach improves somatic mutation prediction accuracy," Genome Medicine 2013, vol. 5:90, pp. 1-14.

Heidary, et al., "The dynamic range of circulating tumor DNA in metastatic breast cancer," Breast Cancer Research 2014, vol. 16:421, pp. 1-10.

English translation of Office Action, JP Patent Application No. 2015-517896, dated Feb. 6, 2018.

(56) References Cited

OTHER PUBLICATIONS

Non-Final Office Action dated Oct. 19, 2018 in U.S. Appl. No. 13/801,748, filed Mar. 13, 2013, 14 pages.
English Translation of Office Action, MX Patent Application No. MX/a/2014/016058, dated Mar. 13, 2018.
Office Action, CA Patent Application No. 2,876,327, dated Mar. 23, 2016, pp. 1-4.
Written Opinion SG Patent Application No. 11201408113Q, dated Aug. 4, 2016, pp. 1-9.
Extended European Search Report, EP 16 74 8745, dated Sep. 18, 2018, 9 pages.
English translation of Office Action in KR 10-2018-7021883, dated Sep. 6, 2018.
Mitchell, William Marvin et al.; "High Sensitivity and Specificity of Chromosomal Pertubations in Human Invasive Breast Cancer (BrCa) Associated with Circulating Nucleic Acids (CNA) Using Concatemers of Short Sequence DNA Tags in Next Generation Sequencing (NGS)"; Experimental Biology Meeting 2011; Washington, DC, USA; Apr. 9-13, 2011; the FASEB Journal; vol. 25, No. 1_supplement; Apr. 2011 PREV201300063370; 1 page.
Larkin, J.M.G. et al.; "A phase II trial of nilotinib in the treatment of patients with KIT mutated advanced acral and mucosal melanoma (NICAM)"; Journal of Clinical Oncology (2011), vol. 29, No. 15_suppl, TPS229-TPS229; 3 pages.
Examination Report No. 1 dated Nov. 21, 2018 in AU Patent Application No. 2017204553, 11 pages.
Extended European Search Report dated Nov. 29, 2018 in EP Patent Application No. 18185290.6, 18 pages.
English translation of Office Action dated Nov. 29, 2018 in IL Patent Application No. 235967, 3 pages.
U.S. Appl. No. 15/362,631, Notice of Allowance dated Aug. 10, 2018, 5 pages.
U.S. Appl. No. 15/362,631, Notice of Allowance dated Oct. 31, 2018, 5 pages.
U.S. Appl. No. 15/362,631, Notice of Allowance dated Jun. 28, 2018, 7 pages.
U.S. Appl. No. 15/362,631, Restriction Requirement dated Apr. 17, 2017, 6 pages.
U.S. Appl. No. 15/362,631, Restriction Requirement dated Sep. 18, 2017, 6 pages.
Australian Application No. 2013278994, Notice of Acceptance dated Mar. 23, 2017, 3 pages.
Fan et al., Whole-Genome 1-15 Molecular Haplotyping of Single Cells, Nature Biotechnology, vol. 29, No. 1, Jan. 1, 2011, pp. 51-57.
Chinese Application No. 201380042981.X, Notice of Decision to Grant dated Aug. 21, 2017, 2 pages.
Chinese Application No. 201380042981.X, Office Action dated Nov. 30, 2016, 5 pages.
Chinese Application No. 201380042981.X, Office Action dated Apr. 13, 2016, 6 pages.
Chinese Application No. 201380042981.X, Office Action dated Nov. 2, 2015, 8 pages.
Eurasian Application No. 201500027, Office Action dated Oct. 22, 2018, 13 pages (8 pages of Original Document and 5 pages of English Translation).
Eurasian Application No. 201500027, Office Action dated Dec. 19, 2017, 21 pages (5 pages of Original Document and 16 pages of English Translation).
Eurasian Application No. 201500027, Office Action dated May 23, 2016, 5 pages (3 pages of Original Document and 2 pages of English Translation).
European Patent Application No. 13807105.5, Notice of Decision to Grant dated Jul. 12, 2018, 3 pages.
Israel Application No. 235967, Office Action dated Apr. 10, 2018, 2 pages.
Japanese Application No. 2015-517896, Notice of Decision to Grant dated Jun. 12, 2018, 2 pages.
Japanese Application No. 2015-517896, Office Action dated Jun. 6, 2017, 7 pages (3 pages of Original Document and 4 pages of English Translation).
Kitzman et al., Supplementary Materials for Noninvasive Whole-Genome Sequencing of a Human Fetus, Science Translational Medicine, vol. 4, No. 137, Jun. 6, 2012, 11 pages.
Korean Application No. 10-2015-7001225, Notice of Decision to Grant dated Apr. 26, 2018, 4 pages (3 pages of Original Document and 1 page of English Translation).
Korean Application No. 10-2015-7001225, Office Action dated Aug. 29, 2017, 9 pages (5 pages of Original Document and 4 pages of English Translation).
Mexican Application No. MX/A/2014/016058, Notice of Allowance dated Aug. 27, 2018, 2 pages.
Mexican Application No. MX/A/2014/016058, Office Action dated Aug. 17, 2017, 4 pages.
International Application No. PCT/CN2016/073753, International Preliminary Report on Patentability dated Aug. 24, 2017, 5 pages.
International Application No. PCT/CN2016/073753, International Search Report and Written Opinion dated May 10, 2016, 7 pages.
International Application No. PCT/IB2013/054898, International Preliminary Report on Patentability dated Dec. 31, 2014, 7 pages.
Singapore Application No. 11201408113Q, Notice of Decision to Grant dated Jul. 26, 2018, 5 pages.
Singapore Application No. 11201408113Q, Written Opinion dated Dec. 8, 2015, 8 pages.
Singapore Application No. 11201706529T, Notice of Decision to Grant dated May 14, 2019, 5 pages.
Taiwan Application No. 102122036, Notice of Decision to Grant dated Jul. 18, 2018, 3 pages.
South Africa Application No. 2014/09281, Notice of Acceptance dated Jul. 25, 2017.
English translation of Office Action dated Aug. 31, 2020 in TW Patent Application No. 105104407. 5 pages.
Final Office Action dated Apr. 27, 2021 in U.S. Appl. No. 13/801,748, filed Mar. 13, 2013. 12 pages.
Examination Report No. 1 dated May 17, 2021 in AU Patent Application No. 2016218631. 4 pages.
Examination Report No. 1 dated Jun. 28, 2021 in AU Patent Application No. 2020200122. 5 pages.

| | Breast | Kidney | Colon | Liver | Lung | Prostate | Cervix | Stomach | Skin | Endometrium | Thyroid | Ovary |
|---|---|---|---|---|---|---|---|---|---|---|---|---|
| TP53 | 23% | 6% | 44% | 27% | 34% | 13% | 5% | 33% | 24% | 18% | 6% | 46% |
| APC | 2% | 1% | 45% | 3% | 2% | 2% | 2% | 8% | 6% | 5% | 3% | 2% |
| BRAF | 1% | 2% | 12% | 1% | 2% | 1% | 1% | 1% | 42% | 2% | 41% | 7% |
| PTEN | 4% | 3% | 5% | 2% | 2% | 7% | 4% | 4% | 8% | 38% | 2% | 3% |
| VHL | 0% | 36% | 1% | 0% | 0% | 0% | 0% | 0% | 1% | 1% | 0% | 0% |
| KRAS | 2% | 0% | 33% | 2% | 16% | 4% | 6% | 6% | 2% | 15% | 2% | 12% |
| EGFR | 1% | 1% | 2% | 1% | 29% | 3% | 1% | 4% | 3% | 4% | 1% | 2% |
| PIK3CA | 27% | 2% | 13% | 3% | 4% | 2% | 14% | 10% | 7% | 23% | 3% | 9% |
| RET | 1% | 1% | 4% | 1% | 2% | 0% | 1% | 2% | 3% | 2% | 26% | 1% |
| ARID1A | 4% | 2% | 11% | 8% | 4% | 1% | 4% | 15% | 6% | 24% | 0% | 9% |
| PBRM1 | 1% | 24% | 4% | 1% | 2% | 0% | 1% | 3% | 4% | 2% | 0% | 0% |
| CTNNB1 | 1% | 7% | 5% | 23% | 2% | 3% | 3% | 8% | 6% | 18% | 3% | 6% |
| FOXL2 | 0% | 0% | 1% | 0% | 1% | 0% | 0% | 1% | 0% | 0% | 0% | 21% |
| TSHR | 1% | 0% | 2% | 0% | 2% | 0% | 0% | 2% | 4% | 1% | 21% | 0% |
| TERT | 3% | 2% | 3% | 15% | 1% | 0% | 1% | 1% | 20% | 2% | 11% | 4% |
| CDKN2A | 2% | 2% | 1% | 5% | 8% | 1% | 5% | 4% | 18% | 2% | 3% | 5% |
| GRIN2A | 2% | 1% | 8% | 2% | 5% | 1% | 2% | 6% | 17% | 4% | 1% | 1% |
| PIK3R1 | 2% | 0% | 4% | 1% | 1% | 0% | 2% | 1% | 2% | 16% | 0% | 1% |
| PTCH1 | 1% | 1% | 6% | 1% | 2% | 0% | 1% | 5% | 16% | 3% | 1% | 1% |
| NRAS | 1% | 0% | 4% | 0% | 1% | 1% | 1% | 1% | 16% | 2% | 7% | 1% |
| ROS1 | 1% | 1% | 5% | 1% | 4% | 1% | 2% | 5% | 14% | 4% | 1% | 2% |
| CDH1 | 11% | 0% | 3% | 1% | 1% | 1% | 1% | 13% | 2% | 3% | 0% | 0% |
| FGFR3 | 0% | 0% | 2% | 0% | 0% | 1% | 1% | 1% | 13% | 1% | 0% | 0% |
| KMT2C | 9% | 3% | 11% | 4% | 8% | 4% | 8% | 11% | 12% | 8% | 3% | 3% |
| NF1 | 3% | 1% | 7% | 2% | 6% | 0% | 3% | 6% | 12% | 5% | 1% | 4% |
| HRAS | 0% | 0% | 0% | 0% | 0% | 2% | 4% | 1% | 11% | 0% | 4% | 0% |
| GATA3 | 11% | 0% | 3% | 0% | 2% | 0% | 0% | 3% | 2% | 1% | 1% | 1% |
| KMT2D | 3% | 3% | 10% | 3% | 6% | 2% | 8% | 9% | 11% | 7% | 0% | 1% |

FIG. 1

1300
Using dynamic cutoff to screen the mutations
32,529 (8,059/11,903 67%)
Tier A: Realign the reads covering the mutation sites
8,298 (Recovery rate: 7,325/11,903 61%; PPV: 88%)
Tier D: Size filter: at least 10-bp difference
6,838 (Recovery rate: 6,109/11,903 51%; PPV: 89%)
FIG. 13

| FPR<1e-10 and score1 > 0.01 | | Predicted sensitivity of mutation detection in plasma (%) | | | | | |
|---|---|---|---|---|---|---|---|
| | Cutoff for mutant alleles | 1% | 2% | 5% | 10% | 15% | 20% |
| Sequencing depth | Buffy coat / Plasma | | | | | | |
| 50 | <=1 / >=6 | 0.0001 | 0.0 | 1.4 | 23.8 | 62.2 | 87.0 |
| 100 | <=1 / >=7 | 0.0010 | 0.1 | 13.3 | 78.0 | 98.2 | 99.9 |
| 150 | <=2 / >=7 | 0.0170 | 1.2 | 47.5 | 98.2 | 100 | 100 |
| 200 | <=2 / >=8 | 0.0237 | 2.1 | 66.7 | 99.8 | 100 | 100 |
| 250 | <=2 / >=9 | 0.0277 | 3.2 | 79.9 | 100 | 100 | 100 |
| 500 | <=3 / >=10 | 1.3695 | 41.7 | 99.9 | 100 | 100 | 100 |
| 600 | <=4 / >=11 | 2.0092 | 53.8 | 100 | 100 | 100 | 100 |
| 1000 | <=6 / >=12 | 41.6960 | 98.9 | 100 | 100 | 100 | 100 |

FIG. 18

| FPR<0.1% and score1 >0.01 | Cutoff for mutant alleles | | Predicted sensitivity of mutation detection in plasma (%) | | | | | |
|---|---|---|---|---|---|---|---|---|
| Sequencing depth | Buffy coat | Plasma | 1% | 2% | 5% | 10% | 15% | 20% |
| 50 | <=1 | >=3 | 0.175 | 1.899 | 24.242 | 73.497 | 94.085 | 98.966 |
| 100 | <=1 | >=3 | 1.90 | 14.29 | 73.50 | 98.97 | 99.98 | 100 |
| 150 | <=2 | >=4 | 1.86 | 18.47 | 86.79 | 99.91 | 100 | 100 |
| 200 | <=2 | >=4 | 5.27 | 37.12 | 97.07 | 100 | 100 | 100 |
| 250 | <=2 | >=4 | 10.9 | 55.95 | 99.47 | 100 | 100 | 100 |
| 500 | <=3 | >=5 | 38.40 | 93.29 | 100 | 100 | 100 | 100 |
| 600 | <=4 | >=6 | 39.37 | 95.42 | 100 | 100 | 100 | 100 |
| 1000 | <=6 | >=7 | 77.98 | 99.92 | 100 | 100 | 100 | 100 |

FIG. 19

| Fixed cutoff | | | | | Size filter | | | | |
|---|---|---|---|---|---|---|---|---|---|
| Cutoff used for mutation identification (at least N mutant alleles seen in plasma) | The number of putative mutations identified in plasma | The number of somatic mutations verified in tumor tissue | PPV% | Recovery rate% | Size cutoff of at least X bp difference | The number of putative mutations identified in human genome | The number of somatic mutations verified in tumor tissue | PPV% | Recovery rate% |
| 2 | 1238513 | 11395 | 0.92 | 95.73 | 5 | 616199 | 10822 | 1.76 | 90.9 |
|   |         |       |      |       | 10 | 500002 | 10117 | 2.02 | 85.0 |
|   |         |       |      |       | 15 | 393749 | 8583  | 2.18 | 72.1 |
|   |         |       |      |       | 20 | 302989 | 6176  | 2.04 | 51.9 |
| 3 | 423581  | 11114 | 2.62 | 93.37 | 5  | 238275 | 10595 | 4.45 | 89.0 |
|   |         |       |      |       | 10 | 186803 | 9901  | 5.30 | 83.2 |
|   |         |       |      |       | 15 | 140332 | 8404  | 5.99 | 70.6 |
|   |         |       |      |       | 20 | 100861 | 6031  | 5.98 | 50.7 |
| 4 | 278504  | 10847 | 3.89 | 91.13 | 5  | 149269 | 10358 | 6.94 | 87.0 |
|   |         |       |      |       | 10 | 115078 | 9680  | 8.41 | 81.3 |
|   |         |       |      |       | 15 | 84331  | 8215  | 9.74 | 69.0 |
|   |         |       |      |       | 20 | 58226  | 5878  | 10.10 | 49.4 |
| 5 | 197631  | 10590 | 5.36 | 88.97 | 5  | 106435 | 10133 | 9.52 | 85.1 |
|   |         |       |      |       | 10 | 81133  | 9475  | 11.68 | 79.6 |
|   |         |       |      |       | 15 | 58571  | 8037  | 13.72 | 67.5 |
|   |         |       |      |       | 20 | 39388  | 5730  | 14.55 | 48.1 |
| 6 | 145772  | 10375 | 7.12 | 87.16 | 5  | 79705  | 9930  | 12.46 | 83.4 |
|   |         |       |      |       | 10 | 60411  | 9285  | 15.37 | 78.0 |
|   |         |       |      |       | 15 | 43200  | 7872  | 18.22 | 66.1 |
|   |         |       |      |       | 20 | 28653  | 5600  | 19.54 | 47.0 |

FIG. 23

| Fixed cutoff | | | | Size filter | | | |
|---|---|---|---|---|---|---|---|
| Cutoff used for mutation identification (at least N mutant alleles seen in plasma) | The number of putative mutations identified in plasma | The number of somatic mutations verified in tumor tissue | PPV% | Recovery rate% | Size cutoff of at least X bp difference | The number of putative mutations identified in human genome | The number of somatic mutations verified in tumor tissue | PPV% | Recovery rate% |
| 2 | 303265 | 10587 | 3.49 | 88.94 | 5 | 156732 | 10072 | 6.43 | 84.6 |
|  |  |  |  |  | 10 | 127277 | 9417 | 7.40 | 79.1 |
|  |  |  |  |  | 15 | 99588 | 7986 | 8.02 | 67.1 |
|  |  |  |  |  | 20 | 75324 | 5712 | 7.58 | 48.0 |
| 3 | 21837 | 10388 | 47.57 | 87.27 | 5 | 28643 | 9921 | 34.64 | 83.3 |
|  |  |  |  |  | 10 | 24250 | 9273 | 38.24 | 77.9 |
|  |  |  |  |  | 15 | 19336 | 7868 | 40.69 | 66.1 |
|  |  |  |  |  | 20 | 14012 | 5619 | 40.10 | 47.2 |
| 4 | 15493 | 10152 | 65.53 | 85.29 | 5 | 14896 | 9712 | 65.20 | 81.6 |
|  |  |  |  |  | 10 | 13382 | 9077 | 67.83 | 76.3 |
|  |  |  |  |  | 15 | 11115 | 7702 | 69.29 | 64.7 |
|  |  |  |  |  | 20 | 7949 | 5486 | 69.01 | 46.1 |
| 5 | 13629 | 9936 | 72.90 | 83.47 | 5 | 13121 | 9519 | 72.55 | 80.0 |
|  |  |  |  |  | 10 | 11896 | 8904 | 74.85 | 74.8 |
|  |  |  |  |  | 15 | 9925 | 7556 | 76.13 | 63.5 |
|  |  |  |  |  | 20 | 7061 | 5367 | 76.01 | 45.1 |
| 6 | 12596 | 9765 | 77.52 | 82.04 | 5 | 12277 | 9359 | 76.23 | 78.6 |
|  |  |  |  |  | 10 | 11143 | 8754 | 78.56 | 73.5 |
|  |  |  |  |  | 15 | 9283 | 7425 | 79.98 | 62.4 |
|  |  |  |  |  | 20 | 6574 | 5266 | 80.10 | 44.2 |

| Source | ID | Correlation between plasma mutation and H3K4me1 | Correlation between plasma mutation and H3K27ac | Correlation between plasma mutation and H3K9me3 |
|---|---|---|---|---|
| Breast | E027 | -0.415 | NA | 0.352 |
| Monocytes | E029 | -0.421 | -0.38 | 0.444 |
| blood | E030 | -0.400 | NA | 0.482 |
| liver | E066 | -0.553 | -0.50 | 0.570 |
| brain | E071 | -0.410 | -0.42 | 0.366 |
| colon | E076 | -0.401 | -0.39 | 0.134 |
| Gastric | E094 | -0.459 | -0.48 | 0.318 |
| lung | E096 | -0.460 | -0.47 | 0.016 |
| Ovary | E097 | -0.391 | -0.42 | 0.080 |
| pancreas | E098 | -0.463 | -0.47 | 0.301 |
| Sigmoid colon | E106 | -0.464 | -0.44 | 0.455 |
| Small intestine | E109 | -0.472 | -0.42 | 0.356 |

*De novo* mutation identification in plasma

Using dynamic cutoff to screen the mutations in plasma
46,652 (47/47 100%)

⇨

Tier A: Realign the reads covering the mutation sites
287 (Recovery rate: 41/47 87%; PPV: 14%)

⇨

Tier C: Mutant fraction (M%) > 30%
43 (Recovery rate: 30/47 62%; PPV: 70%)

Tier B: Mutant fraction (M%) > 20%
89 (Recovery rate: 41/47 87%; PPV: 46%)

⇨

Tier D: Size filter: at least 10-bp difference
53 (Recovery rate: 39/47 83%; PPV: 74%)

FIG. 35

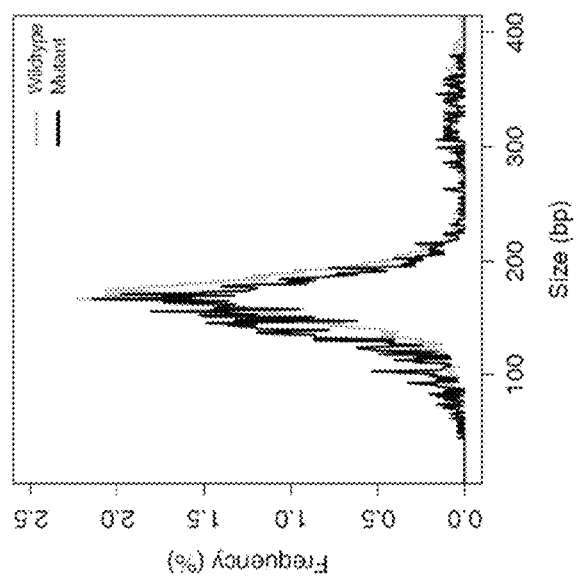
FIG. 36A
FIG. 36B
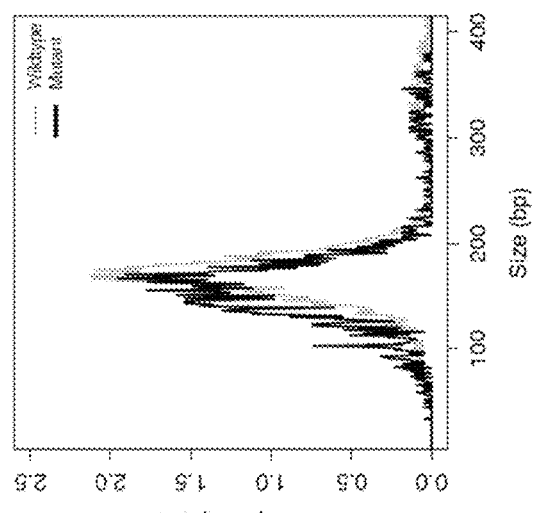
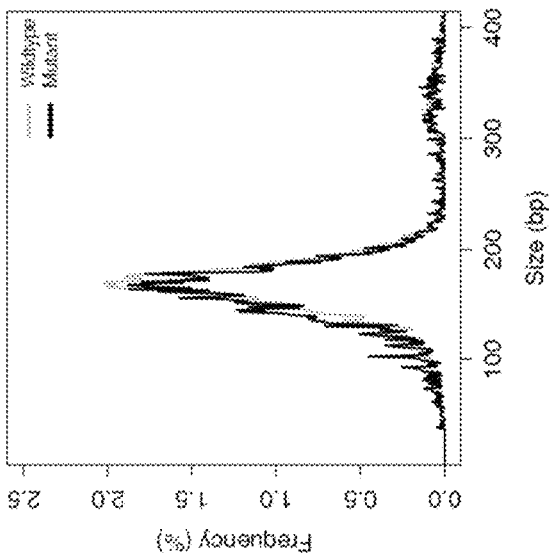
FIG. 36C
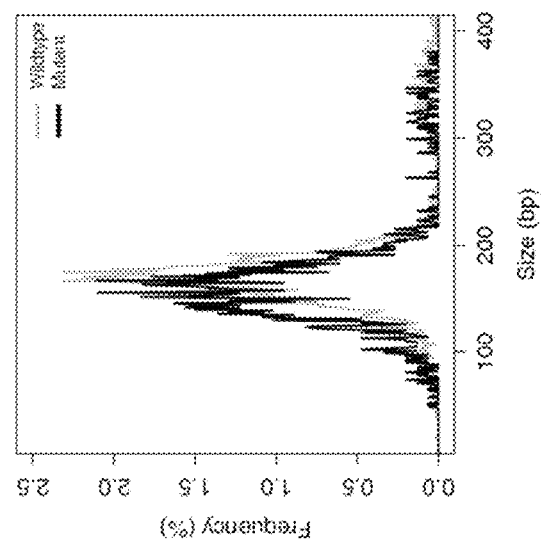
FIG. 36D

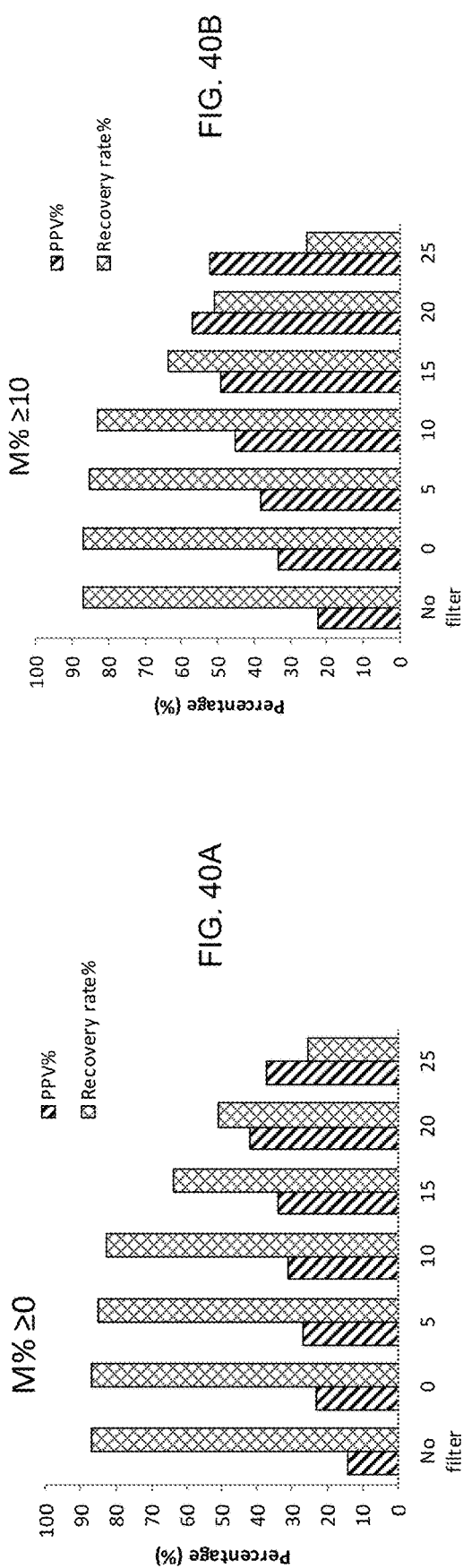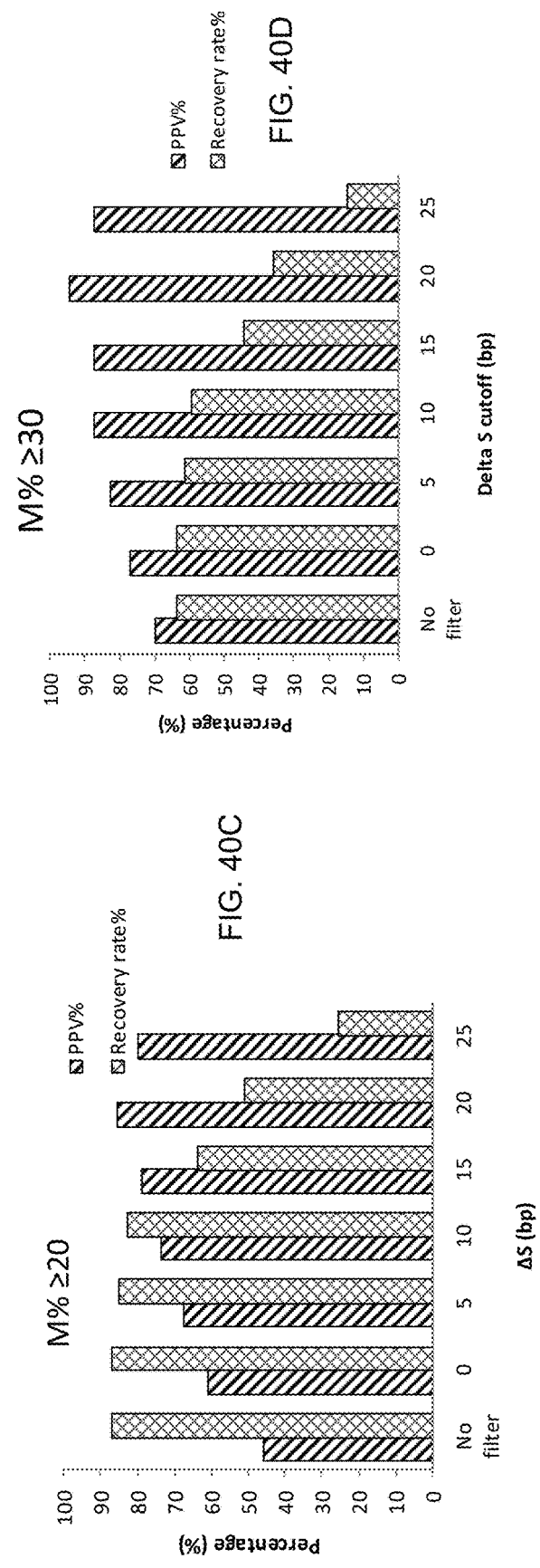
FIG. 40A, FIG. 40B, FIG. 40C, FIG. 40D

| Name | Chr position | Maternal plasma (NGS) Genotype | Count | Father NGS | Father Sanger seq | Mother NGS | Mother Sanger seq | Cord blood NGS | Cord blood Sanger seq | Placenta NGS | Placenta Sanger seq | Remark |
|---|---|---|---|---|---|---|---|---|---|---|---|---|
| TP1 | chr1:86987866 | CT | 259:44 | CC | CC | CC | CC | CT | CT | CT | CT | |
| TP2 | chr2:231414780 | CT | 239:53 | CC | CC | CC | CC | CT | CT | CT | CT | |
| TP3 | chr3:126060289 | GA | 246:50 | GG | GG | GG | GG | GA | GA | GA | GA | |
| TP4 | chr4:73534843 | AC | 204:45 | AA | AA | AA | AA | AC | AC | AC | AC | |
| TP5 | chr4:75070975 | CC | 294:0 | CC | CC | CC | CC | CT | CT | CC | CC | Cord blood-specific |
| TP6 | chr4:95295449 | CA | 261:35 | CC | CC | CC | CC | CC | CC | CA | CA | Placenta-specific |
| TP7 | chr5:83895390 | GA | 253:42 | GG | GG | GG | GG | GA | GA | GA | GA | |
| TP8 | chr6:54202751 | CA | 232:38 | CC | CC | CC | CC | CA | CA | CA | CA | |
| TP9 | chr7:41399864 | TA | 282:59 | TT | TT | TT | TT | TA | TA | TA | TA | |
| TP10 | chr8:117728725 | CT | 235:43 | CC | CC | CC | CC | CT | CT | CT | CT | |
| TP11 | chr10:22255065 | AG | 207:48 | AA | AA | AA | AA | AG | AG | AG | AG | |
| TP12 | chr11:76736964 | TC | 234:58 | TT | TT | TT | TT | TC | TC | TC | TC | |
| TP13 | chr12:106632793 | GA | 230:44 | GG | GG | GG | GG | GA | GA | GA | GA | |
| TP14 | chr14:57083665 | TC | 205:52 | TT | TT | TT | TT | TC | TC | TC | TC | |
| TP15 | chr17:66731200 | CT | 241:44 | CC | CC | CC | CC | CT | CT | CT | CT | |
| TP16 | chr19:33302746 | GA | 248:32 | GG | GG | GG | GG | GG | GG | GA | GA | Placenta-specific |
| TP17 | chr20:41416859 | CT | 165:49 | CC | CC | CC | CC | CT | CT | CT | CT | |
| TP18 | chr21:26925757 | CT | 220:47 | CC | CC | CC | CC | CT | CT | CT | CT | |

FIG. 42

| Name | Chr position | Maternal plasma (NGS) Genotype | Count | Father NGS | Father Sanger seq | Mother NGS | Mother Sanger seq | Cord blood NGS | Cord blood Sanger seq | Placenta NGS | Placenta Sanger seq | Remark |
|---|---|---|---|---|---|---|---|---|---|---|---|---|
| TP19 | chr1:2816785 | GA | 216:38 | GG | GG | GG | GG | AG | AG | GA | GA | |
| TP20 | chr2:60295478 | CT | 310:60 | CC | CC | CC | CC | CT | CT | CT | CT | |
| TP21 | chr3:75762726 | AG | 331:39 | AG (58:1) | AG | AG (62:1) | AG | AG (66:3) | AG | AG (27:1) | AG | All heterozygous |
| TP22 | chr3:77051026 | CT | 264:53 | CC | CC | CC | CC | CT | CT | CT | CT | |
| TP23 | chr4:34755555 | CG | 262:49 | CC | CC | CC | CC | CG | CG | CG | CG | |
| TP24 | chr4:54613139 | CT | 168:28 | CC | CC | CC | CC | CT | CT | CT | CT | |
| TP25 | chr4:68332287 | AG | 182:41 | AA | AA | AA | AA | AG | AG | AG | AG | |
| TP26 | chr4:113248268 | AT | 225:51 | AA | AA | AA | AA | AT | AT | AT | AT | |
| TP27 | chr4:181441802 | TA | 206:41 | TT | TT | TT | TT | TA | TA | TA | TA | |
| TP28 | chr5:2366786 | CT | 233:43 | CC | CC | CC | CC | CT | CT | CT | CT | |
| TP29 | chr5:146803590 | CG | 270:44 | CC | CC | CC | CC | CG | CG | CG | CG | |
| TP30 | chr6:32603242 | GA | 133:16 | GG (36) | GG | GG (24) | GG | GG (36) | GG | GA (21:3) | GG | Placenta-specific; HLA region |
| TP31 | chr6:55920652 | TC | 271:54 | TT | TT | TT | TT | TC | TC | TC | TC | |
| TP32 | chr6:106112398 | GA | 277:57 | GG | GG | GG | GG | GA | GA | GA | GA | |
| TP33 | chr6:169649376 | TC | 182:32 | TT | TT | TT | TT | TC | TC | TC | TC | |
| TP34 | chr6:169937294 | AG | 224:47 | AA | AA | AA | AA | AG | AG | AG | AG | |
| TP35 | chr8:17334059 | CG | 281:36 | CC | CC | CC | CC | CG | CG | CG | CG | |
| TP36 | chr8:107961680 | AC | 309:49 | AA | AA | AA | AA | AC | AC | AC | AC | |
| TP37 | chr9:36612823 | TC | 290:35 | TT | TT | TT | TT | TC | TC | TC | TC | |
| TP38 | chr10:50117829 | AT | 247:65 | AA | AA | AA | AA | AT | AT | AT | AT | |
| TP39 | chr10:121730789 | GA | 204:41 | GG | GG | GG | GG | GA | GA | GA | GA | |
| TP40 | chr12:57200848 | TC | 270:67 | TT | TT | TT | TT | TC | TC | TC | TC | |
| TP41 | chr12:130838521 | CT | 159:31 | CC | CC | CC | CC | CT | CT | CT | CT | |
| TP42 | chr14:33427740 | GA | 240:44 | GG | GG | GG | GG | GA | GA | GA | GA | |
| TP43 | chr15:27113788 | TC | 239:43 | TT | TT | TT | TT | TC | TC | TC | TC | |
| TP44 | chr16:82769063 | GA | 132:18 | GG (45) | GG | GG (22) | GA | GG (37) | GA | GA (11:1) | GA | Placenta-specific; inconsistent NGS and Sanger seq results |
| TP45 | chr17:34340?6 | TC | 229:47 | TT | PCR failed | TT | PCR failed | TC | PCR failed | TC | PCR failed | Re-optimise PCR |
| TP46 | chr17:78880681 | GA | 223:39 | GG | GG | GG | GG | GA | GA | GA | GA | |
| TP47 | chr18:101029B1 | GA | 156:23 | GG | GG | GG | GG | GA | GA | GA | GA | |
| TP48 | chr20:44745129 | AG | 191:34 | AA | AA | AA | AA | GA | GA | GA | GA | |

FIG. 43

Down-sampling analysis

Simulated mutations: 3000
*De novo* mutations: 47
Fetal DNA fraction (%): 32%

| Seq depth (X) | Pass dynamic cutoff | Pass realignment | Pass size filter | Recovered from 47 mutations | False positives | Recovered from 3000 simulated mutations | PPV% | Recovery rate (%) |
|---|---|---|---|---|---|---|---|---|
| 25 | 834 | 482 | 476 | 10 | 4 | 462 | 99.16 | 15.49 |
| 50 | 3496 | 1522 | 1499 | 28 | 10 | 1461 | 99.33 | 48.87 |
| 100 | 10132 | 2072 | 2021 | 35 | 32 | 1954 | 98.42 | 65.28 |

The no. of mutations = 3000

The number of true mutations detected at different tumor DNA fractions (%)

| Depth (X) | 1% | 2% | 3% | 4% | 5% | 10% | 15% | 20% | 30% | FP |
|---|---|---|---|---|---|---|---|---|---|---|
| 25 | 0 | 0 | 1 | 4 | 10 | 102 | 340 | 709 | 1587 | 4 |
| 50 | 0 | 0 | 3 | 10 | 24 | 311 | 961 | 1706 | 2664 | 10 |
| 60 | 0 | 1 | 6 | 21 | 51 | 541 | 1415 | 2187 | 2873 | 12 |
| 80 | 0 | 4 | 22 | 67 | 151 | 1113 | 2176 | 2736 | 2986 | 18 |
| 90 | 0 | 7 | 35 | 104 | 227 | 1411 | 2441 | 2860 | 2996 | 25 |
| 100 | 0 | 10 | 53 | 152 | 319 | 1692 | 2633 | 2929 | 2999 | 32 |
| 200 | 11 | 155 | 550 | 1113 | 1685 | 2921 | 2998 | 3000 | 3000 | 45 |
| 400 | 49 | 642 | 1667 | 2435 | 2806 | 3000 | 3000 | 3000 | 3000 | na |
| 600 | 250 | 1665 | 2658 | 2942 | 2992 | 3000 | 3000 | 3000 | 3000 | na |
| 800 | 643 | 2430 | 2941 | 2996 | 3000 | 3000 | 3000 | 3000 | 3000 | na |

FIG. 45B

The no. of mutations = 6000

The number of true mutations detected at different tumor DNA fractions (%)

| Depth (X) | 1% | 2% | 3% | 4% | 5% | 10% | 15% | 20% | 30% | FP |
|---|---|---|---|---|---|---|---|---|---|---|
| 25 | 0 | 1 | 3 | 9 | 19 | 205 | 681 | 1418 | 3173 | 4 |
| 50 | 0 | 1 | 6 | 19 | 49 | 622 | 1923 | 3413 | 5327 | 10 |
| 60 | 0 | 2 | 13 | 42 | 103 | 1082 | 2829 | 4374 | 5746 | 12 |
| 80 | 0 | 8 | 43 | 134 | 302 | 2227 | 4352 | 5472 | 5972 | 18 |
| 90 | 1 | 13 | 70 | 209 | 453 | 2822 | 4882 | 5721 | 5991 | 25 |
| 100 | 1 | 21 | 106 | 305 | 638 | 3384 | 5266 | 5858 | 5997 | 32 |
| 200 | 21 | 310 | 1101 | 2227 | 3370 | 5841 | 5996 | 6000 | 6000 | 45 |
| 400 | 98 | 1284 | 3333 | 4869 | 5612 | 6000 | 6000 | 6000 | 6000 | na |
| 600 | 500 | 3331 | 5317 | 5883 | 5985 | 6000 | 6000 | 6000 | 6000 | na |
| 800 | 1287 | 4861 | 5882 | 5992 | 6000 | 6000 | 6000 | 6000 | 6000 | na |

FIG. 45C

The no. of mutations = 9000

The number of true mutations detected at different tumor DNA fractions (%)

| Depth (X) | 1% | 2% | 3% | 4% | 5% | 10% | 15% | 20% | 30% | FP |
|---|---|---|---|---|---|---|---|---|---|---|
| 25 | 0 | 1 | 4 | 13 | 29 | 307 | 1021 | 2128 | 4760 | 4 |
| 50 | 0 | 1 | 8 | 29 | 73 | 933 | 2884 | 5119 | 7991 | 10 |
| 60 | 0 | 3 | 19 | 63 | 154 | 1623 | 4244 | 6561 | 8619 | 12 |
| 80 | 0 | 12 | 65 | 201 | 453 | 3340 | 6528 | 8208 | 8957 | 18 |
| 90 | 1 | 20 | 105 | 313 | 680 | 4233 | 7324 | 8581 | 8987 | 25 |
| 100 | 1 | 31 | 159 | 457 | 956 | 5076 | 7899 | 8787 | 8996 | 32 |
| 200 | 32 | 466 | 1651 | 3340 | 5056 | 8762 | 8994 | 9000 | 9000 | 45 |
| 400 | 147 | 1927 | 5000 | 7304 | 8418 | 9000 | 9000 | 9000 | 9000 | na |
| 600 | 751 | 4996 | 7975 | 8825 | 8977 | 9000 | 9000 | 9000 | 9000 | na |
| 800 | 1930 | 7291 | 8823 | 8988 | 8999 | 9000 | 9000 | 9000 | 9000 | na |

FIG. 46A

The no. of mutations = 10000

The number of true mutations detected at different tumor DNA fractions (%)

| Depth (X) | 1% | 2% | 3% | 4% | 5% | 10% | 15% | 20% | 30% | FP |
|---|---|---|---|---|---|---|---|---|---|---|
| 25 | 0 | 1 | 5 | 14 | 32 | 341 | 1135 | 2364 | 5289 | 4 |
| 50 | 0 | 1 | 9 | 32 | 81 | 1036 | 3204 | 5688 | 8879 | 10 |
| 60 | 0 | 3 | 21 | 70 | 171 | 1803 | 4716 | 7290 | 9576 | 12 |
| 80 | 1 | 13 | 72 | 224 | 504 | 3711 | 7254 | 9120 | 9953 | 18 |
| 90 | 1 | 22 | 117 | 348 | 755 | 4703 | 8137 | 9535 | 9985 | 25 |
| 100 | 2 | 34 | 177 | 508 | 1063 | 5640 | 8777 | 9763 | 9996 | 32 |
| 200 | 35 | 517 | 1835 | 3712 | 5617 | 9736 | 9994 | 10000 | 10000 | 45 |
| 400 | 163 | 2141 | 5555 | 8115 | 9353 | 9999 | 10000 | 10000 | 10000 | na |
| 600 | 834 | 5551 | 8861 | 9805 | 9974 | 10000 | 10000 | 10000 | 10000 | na |
| 800 | 2145 | 8101 | 9803 | 9987 | 9999 | 10000 | 10000 | 10000 | 10000 | na |

FIG. 46B

The no. of mutations = 20000

The number of true mutations detected at different tumor DNA fractions (%)

| Depth (X) | 1% | 2% | 3% | 4% | 5% | 10% | 15% | 20% | 30% | FP |
|---|---|---|---|---|---|---|---|---|---|---|
| 25 | 0 | 2 | 10 | 29 | 65 | 682 | 2269 | 4728 | 10578 | 4 |
| 50 | 0 | 3 | 18 | 64 | 163 | 2072 | 6408 | 11376 | 17758 | 10 |
| 60 | 0 | 7 | 42 | 140 | 342 | 3607 | 9432 | 14581 | 19153 | 12 |
| 80 | 1 | 26 | 144 | 447 | 1007 | 7422 | 14508 | 18241 | 19905 | 18 |
| 90 | 2 | 43 | 233 | 696 | 1510 | 9406 | 16275 | 19069 | 19971 | 25 |
| 100 | 3 | 69 | 354 | 1017 | 2125 | 11280 | 17554 | 19526 | 19991 | 32 |
| 200 | 71 | 1035 | 3669 | 7423 | 11235 | 19471 | 19988 | 20000 | 20000 | 45 |
| 400 | 326 | 4282 | 11111 | 16231 | 18706 | 19999 | 20000 | 20000 | 20000 | na |
| 600 | 1668 | 11103 | 17723 | 19611 | 19949 | 20000 | 20000 | 20000 | 20000 | na |
| 800 | 4290 | 16203 | 19606 | 19974 | 19999 | 20000 | 20000 | 20000 | 20000 | na |

FIG. 46C

The no. of mutations = 30000

The number of true mutations detected at different tumor DNA fractions (%)

| Depth (X) | 1% | 2% | 3% | 4% | 5% | 10% | 15% | 20% | 30% | FP |
|---|---|---|---|---|---|---|---|---|---|---|
| 25 | 0 | 3 | 15 | 43 | 97 | 1023 | 3404 | 7092 | 15866 | 4 |
| 50 | 0 | 4 | 28 | 96 | 244 | 3109 | 9613 | 17064 | 26637 | 10 |
| 60 | 0 | 10 | 63 | 211 | 513 | 5410 | 14147 | 21871 | 28729 | 12 |
| 80 | 2 | 39 | 216 | 671 | 1511 | 11134 | 21761 | 27361 | 29858 | 18 |
| 90 | 3 | 65 | 350 | 1044 | 2265 | 14110 | 24412 | 28604 | 29956 | 25 |
| 100 | 5 | 103 | 531 | 1525 | 3188 | 16921 | 26331 | 29289 | 29987 | 32 |
| 200 | 106 | 1552 | 5504 | 11135 | 16852 | 29207 | 29982 | 30000 | 30000 | 45 |
| 400 | 489 | 6422 | 16666 | 24346 | 28058 | 29998 | 30000 | 30000 | 30000 | na |
| 600 | 2502 | 16654 | 26584 | 29416 | 29923 | 30000 | 30000 | 30000 | 30000 | na |
| 800 | 6434 | 24304 | 29410 | 29962 | 29998 | 30000 | 30000 | 30000 | 30000 | na |

DETECTING MUTATIONS FOR CANCER SCREENING

CROSS-REFERENCES TO RELATED APPLICATIONS

The present application is a divisional application of U.S. patent application Ser. No. 15/362,631, entitled "Detecting Mutations for Cancer Screening and Fetal Analysis" filed Nov. 28, 2016, which claims priority from and is a continuation application of International Patent Application No. PCT/CN2016/073753, filed Feb. 14, 2016, which claims priority to U.S. Provisional Application No. 62/114,471, entitled "Detecting Cancer" filed Feb. 10, 2015 and U.S. Provisional Application No. 62/271,196, entitled "Detecting De Novo Mutations" filed Dec. 22, 2015, the entire contents of which are herein incorporated by reference for all purposes.

This application is also related to commonly owned U.S. Patent Publication No. 2014/0100121 entitled "Mutational Analysis Of Plasma DNA For Cancer Detection" by Lo et al. filed Mar. 13, 2013; and PCT Patent Publication No. WO2014/043763 entitled "Non-Invasive Determination Of Methylome Of Fetus Or Tumor From Plasma" by Lo et al., filed Sep. 20, 2013, the disclosures of which are incorporated by reference in its entirety for all purposes.

BACKGROUND

It has been shown that tumor-derived DNA is present in the cell-free plasma/serum of cancer patients (Chen et al. Nat Med 1996; 2: 1033-1035). Most current methods are based on the direct analysis of mutations known to be associated with cancer (Diehl et al. Proc Natl Acad Sci USA 2005; 102: 16368-16373; Forshew et al. Sci Transl Med 2012; 4: 136ra68). But, such direct analysis of a panel of predetermined mutations to analyze has had a low accuracy in screening for cancer, e.g., by analyzing plasma DNA.

Further, such a direct analysis using a panel of predetermined mutations provides a limited view at the genetic make-up of a tumor. Thus, surgical biopsies are normally taken in order for sequencing to be performed on a tumor, to obtain genetic information about the tumor. The requirement of surgery increases risks and costs. Additionally, to find a location of a tumor, expensive scanning techniques are required before a surgical biopsy can be performed.

It is therefore desirable to provide new techniques to perform a broad screening, detection, or assessment for cancer, particularly in a noninvasive manner.

BRIEF SUMMARY

Embodiments are related to the accurate detection of somatic mutations in the plasma (or other samples containing cell-free DNA) of cancer patients and for subjects being screened for cancer. The detection of these molecular markers would be useful for the screening, detection, monitoring, management, and prognostication of cancer patients. For example, a mutational load can be determined from the identified somatic mutations, and the mutational load can be used to screen for any or various types of cancers, where no prior knowledge about a tumor or possible cancer of the subject may be required. Embodiments can be useful for guiding the use of therapies (e.g. targeted therapy, immunotherapy, genome editing, surgery, chemotherapy, embolization therapy, anti-angiogenesis therapy) for cancers. Embodiments are also directed to identifying de novo mutations in a fetus by analyzing a maternal sample having cell-free DNA from the fetus.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 1 shows a table 100 of the top 28 most commonly identified mutations among cancers.

FIG. 13 shows a filtering process 1300 (which uses dynamic cutoff, realignment, and size), and the resulting data for mutations identified from plasma according to embodiments of the present invention.

FIG. 18 is a table showing predicted sensitivities of mutation detection for various mutation fractions and sequencing depths for certain allelic count cutoffs according to embodiments of the present invention.

FIG. 19 is a table 1900 showing predicted sensitivities of mutation detection for various mutation fractions and sequencing depths for certain allelic count cutoffs for a false-positive detection rate of 0.1% according to embodiments of the present invention.

FIG. 23 is a table 2300 showing PPVs and recovery rates for various size cutoffs without realignment according to embodiments of the present invention.

FIG. 24 is a table 2400 showing PPVs and recovery rates for various size cutoffs with realignment according to embodiments of the present invention.

FIG. 35 shows a filtering process 3500 (which uses dynamic cutoff, realignment, and mutation fraction, and size cutoff) and the resulting data for de novo mutations identified from plasma according to embodiments of the present invention.

FIG. 36A shows size profiles of DNA fragments with the putative mutations identified in plasma using Tier A filtering criteria compared to wildtype allele. FIG. 36B shows size profiles of DNA fragments with the putative mutations identified in plasma using Tier B filtering criteria. FIG. 36C shows size profiles of DNA fragments with the putative mutations identified in plasma using Tier C filtering criteria. FIG. 36D shows size profiles of DNA fragments with the putative mutations identified in plasma using Tier D filtering criteria.

FIGS. 40A-40D show graphs of PPV % and recovery rates for various size filters at different mutant fraction cutoffs.

FIGS. 42 and 43 show a table of the 47 de novo mutations.

FIG. 44 shows the recovery rates and PPVs for the detection of the 47 de novo mutations and the 3,000 presumed somatic mutations FIGS. 45A-45C and 46A-46C show simulations at varying amount of mutations for various sequencing depths and tumor fractions.

TERMS

Figure 2:
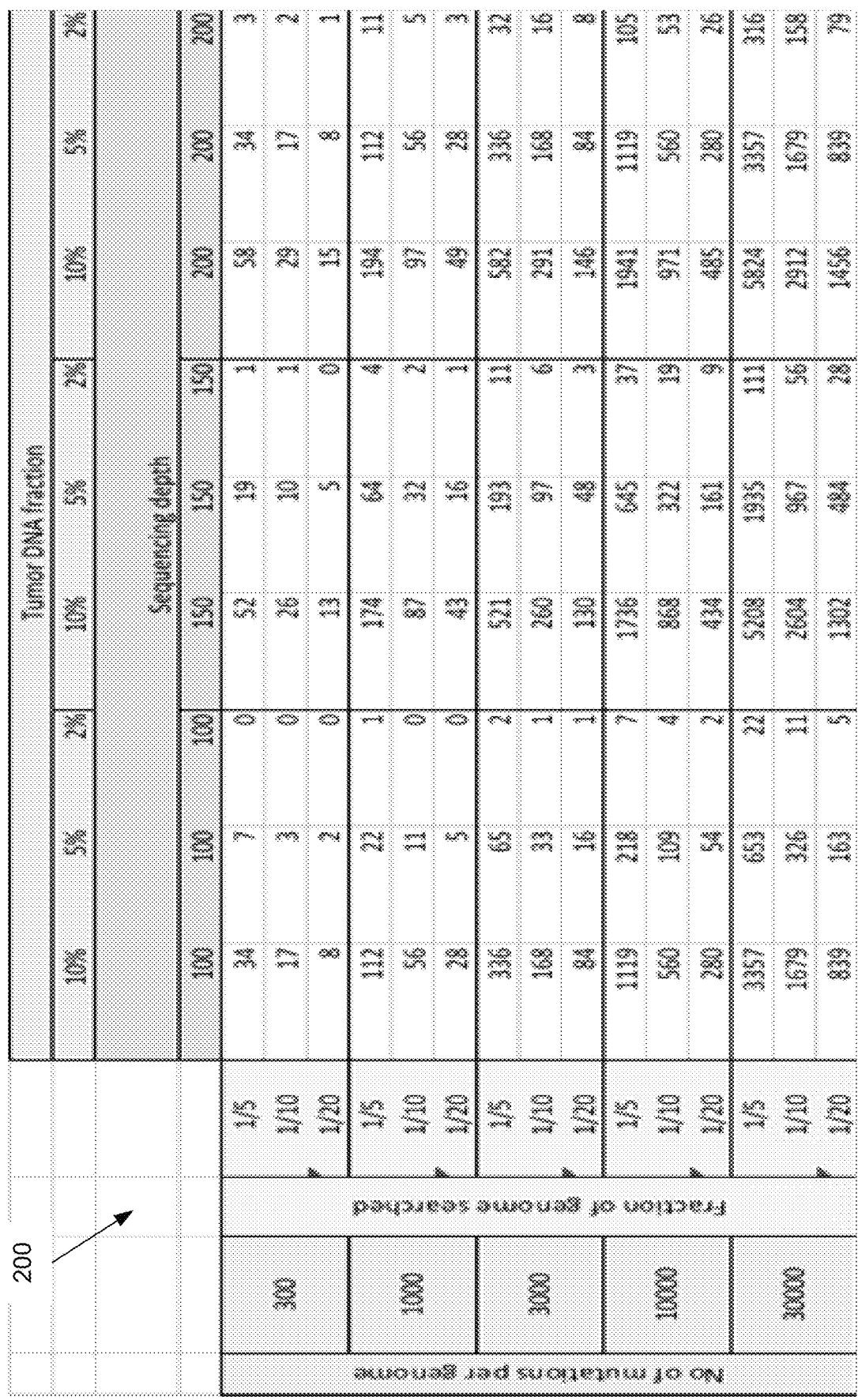
FIG. 2 is a table 200 showing an expected number of mutations to be detected for different tumor DNA fractions, sequencing depths, number of mutation per genome and the fraction of genome searched.

The term "biological sample" refers to any sample that is taken from a subject (e.g., a human, a person with cancer, a person suspected of having cancer, a person to be screened for cancer, a pregnant woman, or other organisms). A biological sample can include cell-free DNA, some of which can have originated from healthy cells and some from tumor cells. Cell-free DNA can be found in blood or its components (e.g. plasma or platelets) or its derivatives (e.g. serum) or other fluids, e.g., urine, other fluids from the urogenital tract, sweat, pleural fluid, ascitic fluid, peritoneal fluid, saliva, tears, nipple discharge, cerebrospinal fluid, intraocular fluid, amniotic fluid, and cervical lavage fluid. A non-fluid example is a stool sample, which may be mixed with diarrheal fluid. For some of such samples, the biological sample can be obtained noninvasively. In some embodiments, the biological sample can be used as a constitutional sample.

As used herein, the term "locus" or its plural form "loci" is a location or address of any length of nucleotides (or base pairs) that may have a variation across genomes of different individuals or across different cells within an individual (e.g., between tumor cells and healthy cells).

The term "random sequencing" as used herein refers to sequencing whereby the nucleic acid fragments sequenced have not been specifically identified or predetermined before the sequencing procedure. Sequence-specific primers to target specific gene loci are not required. In one embodiment, adapters are added to the end of a fragment, and the primers for sequencing attached to the adapters. Thus, any fragment can be sequenced with the same primer, and thus the sequencing can be random. Massively parallel sequencing may be performed using random sequencing.

The term "sequence tag" (also referred to as sequence read) as used herein refers to string of nucleotides sequenced from any part or all of a nucleic acid molecule. For example, a sequenced tag may be a short string of nucleotides (e.g., ~30) sequenced from a nucleic acid fragment, a short string of nucleotides at both ends of a nucleic acid fragment, or the sequencing of the entire nucleic acid fragment that exists in the biological sample. A nucleic acid fragment is any part of a larger nucleic acid molecule. A fragment (e.g. a gene) may exist separately (i.e. not connected) to the other parts of the larger nucleic acid molecule.

A "sequence variant" (also called a variant) corresponds to differences from a reference genome, which could be a constitutional genome of an organism or parental genomes. Examples of sequence variants include a single nucleotide variant (SNV) and variants involving two or more nucleotides. Examples of SNVs include single nucleotide polymorphisms (SNPs) and point mutations. As examples, mutations can be "de novo mutations" (e.g., new mutations in the constitutional genome of a fetus) or "somatic mutations" (e.g., mutations in a tumor). A wildtype allele corresponds to an allele in the constitutional genome. A constitutional genome may contain two wildtype alleles if the subject is heterozygous at that locus. A wildtype sequence variant corresponds to the sequence at a particular location in the constitutional genome. A constitutional genome may contain two wildtype sequence variants if the subject is heterozygous at that locus.

A "somatic mutation" refers to mutations in tissues or cells that develop post-natally. Organisms accumulate more mutations with age, due to errors in DNA replication, or as a result of exposure to carcinogens or other environmental factors. Typically, humans acquire one mutation per cell per cell division. But individually, such mutations are present at extremely low concentration in the tissue because these are non-clonal. However, tumor-associated mutations are clonally amplified and are present at higher fractional concentration in a tumor tissue. The fractional concentration of different mutations in a cancer can be different due to tumoral heterogeneity. This means that a tumor is typically made up of many different clones and each clone has their own mutational profile.

"Cancer-associated changes" or "cancer-specific changes" include, but are not limited to, cancer-derived mutations (including single nucleotide mutations, deletions or insertions of nucleotides, deletions of genetic or chromosomal segments, translocations, inversions), amplification of genes, genetic segments or chromosomal segments, virus-associated sequences (e.g. viral episomes and viral insertions), aberrant methylation profiles or tumor-specific methylation signatures, aberrant cell-free DNA size profiles, aberrant histone modification marks and other epigenetic modifications, and locations of the ends of cell-free DNA fragments that are cancer-associated or cancer-specific.

An "informative cancer DNA fragment" corresponds to a DNA fragment bearing or carrying any one or more of the cancer-associated or cancer-specific change or mutation. An "informative fetal DNA fragment" corresponds to a fetal DNA fragment carrying a mutation not found in either of the genomes of the parents. An "informative DNA fragment" can refer to either of the above types of DNA fragments.

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50×, 100×, etc., where "x" refers to the number of times a locus is covered with a sequence read. Sequencing depth can also be applied to multiple loci, or the whole genome, in which case x can refer to the mean number of times the loci or the whole genome, respectively, is sequenced. Ultra-deep sequencing can refer to at least 100× in sequencing depth.

The term "sequencing breadth" refers to what fraction of a particular reference genome (e.g., human) or part of the genome has been analyzed. The denominator of the fraction could be a repeat-masked genome, and thus 100% may correspond to all of the reference genome minus the masked parts. Any parts of a genome can be masked, and thus one can focus the analysis on any particular part of a reference genome. Broad sequencing can refer to at least 0.1% of the genome being analyzed, e.g., by identifying sequence reads that align to that part of a reference genome.

"Exhaustive sequencing" refers to obtaining molecular information from almost all practically analyzable clinically-relevant or biologically-relevant nucleic acid fragments in a sample, e.g., plasma. Due to limitations in the sample preparation steps, sequencing library preparation steps, sequencing, base-calling and alignment, not all plasma nucleic molecules (e.g., DNA or RNA) in a sample would be analyzable or sequenceable.

An "analyzable DNA molecule" refers to any DNA molecule that has successfully passed through all analytical steps to be analyzed and detected by any suitable means, including sequencing. A "sequenceable DNA molecule" refers to any DNA molecule that has successfully passed through all analytical steps to be sequenced and detected bioinformatically. Thus, exhaustive sequencing can refer to procedures implemented to maximize the ability to transform as many of the clinically-relevant or biologically-relevant DNA molecules (e.g., informative DNA fragments) in a finite plasma sample into sequenceable molecules. After one has created a sequencing library of sequenceable DNA molecules using such procedures, one may sequence all or part of the library. If one indeed fully consumes the sequenceable DNA molecules from the finite sample to obtain sequence information, this act could be termed "total template sequencing," which corresponds to one spectrum of exhaustive sequencing.

A "mutational load" of a sample is a measured value based on how many mutations are measured. The mutational load may be determined in various ways, such as a raw number of mutations, a density of mutations per number of bases, a percentage of loci of a genomic region that are identified as having mutations, the number of mutations observed in a particular amount (e.g. volume) of sample, and proportional or fold increase compared with the reference data or since the last assessment. A "mutational load assessment" refers to a measurement of the mutational load of a sample.

The "positive predictive value (PPV)" of a screening test refers to the number of true positives (TP) identified by a test expressed as a proportion of the sum of the true positives and false positives (FP) classified by the test, e.g., TP/(TP+FP). A "negative predictive value (NPV)" refers to the number of true negatives (TN) identified by the test expressed as a proportion of the sum of true negatives and false negatives (FN) classified by the test, e.g., TN/(TN+FN).

The term "constitutional genome" (also referred to a CG) is composed of the consensus nucleotides at loci within the genome, and thus can be considered a consensus sequence. The CG can cover the entire genome of the subject (e.g., the human genome), or just parts of the genome. The constitutional genome (CG) can be obtained from DNA of cells as well as cell-free DNA (e.g., as can be found in plasma). Ideally, the consensus nucleotides should indicate that a locus is homozygous for one allele or heterozygous for two alleles. A heterozygous locus typically contains two alleles which are members of a genetic polymorphism. As an example, the criteria for determining whether a locus is heterozygous can be a threshold of two alleles each appearing in at least a predetermined percentage (e.g., 30% or 40%) of reads aligned to the locus. If one nucleotide appears at a sufficient percentage (e.g., 70% or greater) then the locus can be determined to be homozygous in the CG. Although the genome of one healthy cell can differ from the genome of another healthy cell due to random mutations spontaneously occurring during cell division, the CG should not vary when such a consensus is used. Some cells can have genomes with genomic rearrangements, e.g., B and T lymphocytes, such as involving antibody and T cell receptor genes, respectively. Such large scale differences would still be a relatively small population of the total nucleated cell population in blood, and thus such rearrangements would not affect the determination of the constitutional genome with sufficient sampling (e.g., sequencing depth) of blood cells. Other cell types, including buccal cells, skin cells, hair follicles, or biopsies of various normal body tissues, can also serve as sources of CG.

The term "constitutional DNA" refers to any source of DNA that is reflective of the genetic makeup with which a subject is born. Random mutations may occur during cell division. Unlike cancer-associated mutations, there is no clonal amplification of the random mutations. Thus, the CG obtained from the consensus sequence of the constitutional DNA is reflective of the genetic makeup with which a subject is born. For a subject, examples of "constitutional samples", from which constitutional DNA can be obtained, include healthy blood cell DNA, buccal cell DNA, hair root DNA, salivary DNA and DNA from skin scrapings. The DNA from these healthy cells defines the CG of the subject. The cells can be identified as healthy in a variety of ways, e.g., when a person is known to not have cancer or the sample can be obtained from a tissue that is not likely to contain cancerous or premalignant cells (e.g., hair root DNA when liver cancer is suspected). As another example, a plasma sample may be obtained when a patient is cancer-free, and the determined constitutional DNA compared against results from a subsequent plasma sample (e.g., a year or more later). In another embodiment, a single biologic sample containing <50% of tumor DNA can be used for deducing the constitutional genome and the tumor-associated genetic alterations. In such a sample, the concentrations of tumor-associated single nucleotide mutations would be lower than those of each allele of heterozygous SNPs in the CG. Such a sample can be the same as the biological sample used to determine a sample genome, described below.

The term "sample genome" (also referred to as SG) is a collection of sequence reads that have been aligned to locations of a genome (e.g., a human genome). The sample genome (SG) is not a consensus sequence, but includes nucleotides that may appear in only a sufficient number of reads (e.g., at least 2 or 3, or higher cutoff values). If an allele appears a sufficient number of times and it is not part of the CG (i.e., not part of the consensus sequence), then that allele can indicate a "single nucleotide mutation" (also referred to as an SNM). Other types of mutations can also be detected, e.g. mutations involving two or more nucleotides (such as those that affect the number of tandem repeat units in a microsatellite or simple tandem repeat polymorphism), chromosomal translocation (which can be intrachromosomal or interchromosomal) and sequence inversion.

The term "reference genome" (also referred to as RG) refers to a haploid or diploid genome to which sequence reads from the biological sample and the constitutional sample can be aligned and compared. For a haploid genome, there is only one nucleotide at each locus. For a diploid genome, heterozygous loci can be identified, with such a locus having two alleles, where either allele can allow a match for alignment to the locus.

The term "level of cancer" can refer to whether cancer exists, a stage of a cancer, a size of tumor, the cancer's response to treatment, and/or other measure of a severity or progression of a cancer. The mutational load can be used to determine the level of cancer. The more advanced the cancer, the higher the mutational load would be. The level of cancer could be a number or other characters, such as letters or other symbols. The level could be zero. The level of cancer also includes premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer. Detection can mean 'screening' or can mean checking if someone, with suggestive features of cancer (e.g. symptoms or other positive tests) or with risk factors for cancer (e.g. habits such as smoking or alcohol drinking or history of viral infections, e.g. hepatitis virus infection), has cancer.

The term "classification" as used herein refers to any number(s) or other characters(s) that are associated with a particular property of a sample. For example, a "+" symbol (or the word "positive") could signify that a sample is classified as having a particular level of cancer. The classification can be binary (e.g., positive or negative) or have more levels of classification (e.g., a scale from 1 to 10 or 0 to 1). The term "cutoff" and "threshold" refer to a predetermined number used in an operation. A threshold value may be a value above or below which a particular classification applies. A cutoff may be predetermined with or without reference to the characteristics of the sample or the person. For example, cutoffs may be chosen based on the age or sex of the tested individual. A cutoff may be chosen after and based on output of the test data. For example, certain cutoffs may be used when the sequencing of a sample reaches a certain depth.

DETAILED DESCRIPTION

The identification of mutations in a biological sample of an organism (e.g., due to cancer or in a fetus) is hampered by the prevalence of sequencing errors and other difficulties. Embodiments provide techniques for accurately identifying mutations in an organism by analyzing cell-free DNA molecules (fragments) of the organism. For a fetal analysis of a sample obtained non-invasively, the cell-free DNA molecules of the fetus would be in a maternal sample (e.g. maternal plasma) that also contains cell-free DNA molecules of the pregnant female. Significant numbers of true mutations (as opposed to false positives) can be identified or the proportion of true mutations detected can be substantially enhanced using certain sequencing techniques (e.g., PCR-free preparation of sequencing libraries) and certain filtering criteria.

When a sufficient sequencing depth and sequencing breadth are used, an accurate measurement of mutational load of a subject can be determined, thereby allowing an assessment of a level of cancer in the subject. Below, the theoretical basis and practical implementation is described for the requirements of DNA-based tumor markers (e.g., in plasma) for cancer detection, monitoring, and prognostication.

I. Mutational Markers for Cancer

Not many cancers have clear mutational or other markers for identifying that cancer exists or is highly likely to be present in an individual. And, even if such markers do exist, there are generally few such known markers that are unique for a specific cancer. Thus, it can be difficult to detect cancer in plasma or other such sample with cell-free DNA, where such mutational markers would not be in high concentration. One exception is Epstein-Barr virus (EBV) DNA in nasopharyngeal carcinoma (NPC) patients. Hence, EBV DNA can be found in the nuclei of NPC tumor cells in most NPC cases in China (Tsang et al. Chin J Cancer 2014; 33: 549-555). Furthermore, EBV DNA can be found in the plasma of NPC patients (Lo et al. Cancer Res 1999; 59: 1188-1191).

This example is used to illustrate the difficulty in obtaining sufficient data to screen for cancer using point mutations of a panel to screen for a particular type of cancer. This example further illustrates the need to detect many mutations in plasma to reach the sensitivity for cancer screening.

A. EBV DNA in NPC Patients

NPC is closely associated with EBV infection. In southern China, the EBV genome can be found in the tumor tissues in almost all NPC patients. The plasma EBV DNA derived from NPC tissues has been developed as a tumor marker for NPC (Lo et al. Cancer Res 1999; 59: 1188-1191). This tumor marker has been shown to be useful for the monitoring (Lo et al. Cancer Res 1999; 59: 5452-5455) and prognostication (Lo et al. Cancer Res 2000; 60: 6878-6881) of NPC. It has been shown that plasma EBV DNA analysis using real-time PCR is useful for the detection of early NPC in asymptomatic subjects and can potentially be useful for the screening of NPC (Chan et al. Cancer 2013; 119:1838-1844). In this previous study, the real-time PCR assay used for plasma EBV DNA analysis targeted the BamHI-W-fragment of the EBV genome. There are about six to twelve repeats of the BamHI-W-fragments in each EBV genome and there are approximately 50 EBV genomes in each NPC tumor cell (Longnecker et al. Fields Virology, 5$^{th}$ Edition, Chapter 61 "Epstein-Barr virus"; Tierney et al. J Virol. 2011; 85: 12362-12375). In other words, there would be of the order of 300-600 (e.g., about 500) copies of the PCR target in each NPC tumor cell. This high number of target per tumor cell may explain why the plasma EBV DNA is so sensitive in the detection of early NPC.

B. Targeted Sequencing for EBV DNA

As illustrated in the above example, the high sensitivity of real-time PCR analysis of plasma EBV DNA is related to the presence of multiple copies of the PCR target in each NPC tumor genome. We therefore reason that further increase in the number of tumor-associated targets that one would seek to detect in a cancer patient's plasma would further increase the sensitivity and clinical utility of plasma DNA analysis. EBV DNA molecules in the plasma of NPC patients are mainly short fragments of below 180 bp (Chan et al. Cancer Res 2003; 63: 2028-2032). As the size of an EBV genome is approximately 172 kb, each EBV genome would be fragmented into approximately 1,000 plasma DNA fragments. Thus, the 50 EBV genomes in a NPC tumor cell would be fragmented into some 50,000 plasma DNA fragments and be released into the circulation of an NPC patient.

We reason that the more of these 50,000 tumor-derived EBV DNA fragments that one would target, the higher is the sensitivity of detecting an EBV-associated cancer that one would be able to achieve. One can detect 5%, 10%, 20%, 25%, 30%, 40%, 50%, 75%, 90% or 99% of the EBV genome for use in analysis. One can aim to target the parts of the EBV genome that one could differentiate bioinformatically from the human genome.

The high sensitivity of detection offered by detecting such a high multiplicity of EBV genomic targets in plasma is particularly important in the detection of disease recurrence in patients receiving curative intent radiotherapy. The detection rate of recurrent NPC in patients who received curative intent radiotherapy is inferior to the detection rate of treatment-naïve NPC (Leung et al. Clin Cancer Res 2003; 9: 3431-3134). The overall detection rates for the two groups of cancers using real-time EBV DNA PCR targeting the BamHI-W-fragment were 62.5% and 96.4%, respectively. Such high detection rates illustrate the need for high multiplicity in any screening technique. Such high multiplicity in a highly correlated target is typically not available for other cancers.

The detection of a high multiplicity of EBV genomic targets (or deduced mutations as described later) in plasma would be expected to increase the detection rate in the former group. Another utility of this approach would be for the screening of NPC. For screening, it is particularly important that one can detect early stage cancer. A highly sensitive plasma EBV DNA detection system would allow this goal. As explained later, embodiments can provide highly sensitive detection without requiring the use of a predetermined mutational or other molecular marker.

II. Screening for Cancers

A problem in screening for cancer is that it may not be known what kind of cancer a subject might have or be predisposed to. Another problem is that an individual may be susceptible to more than one type of cancer. Accordingly, embodiments can identify mutations from a biological sample of the subject, thereby not needing to screen for only a predetermined panel of mutations. Details of how to accurately identify mutations from cell-free DNA in a sample are described in later sections. Processes and difficulties of cancer screening are now described.

Once mutations are identified in a biological sample (e.g., plasma), the mutations can be used in cancer screening. The term screening generally refers to the identification of disease through the proactive act of performing some form of assessment. Assessment tools could include the assessment of a person's demographic profile, performing blood tests, tests of other body fluids (e.g., urine, ascitic fluid, pleural fluid, cerebrospinal fluid), tests on tissue biopsies, endoscopy (e.g. colonoscopy), and imaging tests (e.g. via magnetic resonance imaging, computed tomography, ultrasonography or positron emission tomography). A combination of the assessment modalities may be used, e.g., multiple samples may be used and the results may be combined to provide a final assessment.

A. Different Stages of Screening and Probabilistic Assessment

Disease screening can generally be applied at different stages of disease, namely but not limited to primary, secondary, and tertiary screening. Primary screening refers to the identification of disease before symptom onset and is sometimes referred as asymptomatic screening. Primary screening could be performed on the general population or a selected population with characteristics that render them at increased risk for the disease to be screened. For example, smokers are at increased risk for small cell carcinoma of the lungs. Chronic HBV carriers are at increased risk for HCC. Secondary screening refers to the identification of disease when the subject presents with symptoms and differentiation between a group of presumptive diagnoses would need to be made. Tertiary screening refers to the early identification of progression of disease, increase in disease stage or severity (e.g. the development of metastasis), or relapse of disease. At every stage of disease screening or cancer screening, the aim is to identify or exclude the presence of disease or disease progression, usually before the natural course of the disease presents itself in symptoms, as treatment options may be compromised or less effective at such a later time.

The act of screening is a probabilistic assessment. In general, the purpose of screening is to rule out (i.e. exclude) or to rule in (i.e. confirm) a presumptive diagnosis. The assessment is to determine if a person has a high or a low chance (alternatively termed risk) of developing the disease, having the disease, or having disease progression. In other words, a classification of whether the subject is at high or low risk is made after each assessment. Successive stages of assessment may be needed, and repeat testing may be performed.

B. EBV Examples

EBV is used as an example illustrating screening. A middle aged southern Chinese male has a higher risk of developing NPC than persons with a different demographic profile. The plasma EBV DNA test could then be applied as a primary screening tool of this individual. If the plasma EBV DNA load is below the cutoff used to differentiate individuals with NPC, this person would be deemed to have a low chance of having NPC at this moment (Chan et al. Cancer 2013; 119: 1838-1844). The person may elect or be recommended to have the plasma EBV DNA test again later (e.g. after one or two years).

If the plasma EBV DNA load is found to be higher than the cutoff used to differentiate those with NPC, or show progressive increase from the person's own previous values, this person may be deemed to be of high risk of having NPC. This person may be recommended to the next stage of testing to further rule in or out the disease, e.g., using other tests to confirm the disease. For example, another plasma EBV DNA test could be performed 2 or 6 weeks later to assess if there is persistence in the elevation of plasma EBV DNA. Depending on the index of suspicion, the person may be recommended to have endoscopy for visual inspection of the nasopharynx with and without further tissue biopsy and histological assessment to confirm the presence of NPC. Alternatively, imaging (e.g., magnetic resonance imaging) may be performed to visualize the presence or absence of tumor. Such examples illustrate the benefits of the screening being able to dictate which additional tests should be performed.

The same test could be applied as a tool for secondary and tertiary screening. For illustration, the plasma EBV DNA test could be used to assess the likelihood of NPC in a subject presenting with recurrent epistaxis (i.e. bleeding from the nose) or hoarseness of voice, which are common presenting symptoms of NPC. If the test results show an EBV DNA load is higher than the cutoff used to differentiate the populations with and without disease, this person would be deemed to be of high chance as having NPC, thereby determining a higher level of cancer (Lo et al. Cancer Res 1999; 59: 1188-1191). He may then be referred for further confirmatory testing. On the other hand, if the plasma EBV DNA test shows an EBV DNA load that is lower than the cutoff to discriminate the populations with and without disease, the chance of NPC may be deemed to be low, and other presumptive diagnoses may be considered.

In terms of tertiary screening, an NPC subject with curative treatment by radiotherapy may be tested by the plasma EBV DNA test for the early identification of possible NPC recurrence, in other words, relapse (Lo et al. Cancer Res 1999; 59: 5452-5455; Lo et al. Cancer Res 2000; 60: 6878-6881). The probability of NPC recurrence would be deemed high if the plasma EBV DNA levels increases beyond a stable post-treatment baseline of the subject's own values or beyond the cutoff used to identify the population with NPC recurrence.

C. Other Screening Tests and Preferable Characteristics

The example of plasma EBV DNA testing for the management of NPC is only provided as one illustration of how cancer or disease screening is performed. It would be ideal if other effective screening tests or modalities could be developed for other cancers. Currently, screening tests for other cancers are either non-existent or have poor performance profiles. For example, serum alpha-fetoprotein (AFP) is a marker used for the assessment of HCC. However, serum AFP shows poor sensitivity and specificity. In terms of sensitivity, less than 50% of HCCs are positive for AFP. In terms of specificity, other liver inflammatory conditions could be associated with elevated serum AFP.

Therefore, serum AFP is generally not used as a primary screening tool for asymptomatic low risk individuals. If used, there would be many false-negative and false-positive identification of HCC. Instead, it may be applied to high risk individuals with a high index of suspicion for developing HCC. For example, a chronic HBV carrier with a hypoechoic shadow shown on liver ultrasound may be tested for serum AFP. If positive, it serves as an additional piece of evidence to support the presumptive diagnosis of HCC. In addition, if a confirmed case of HCC is shown to be positive or elevated serum AFP, the serum AFP may be used as a post-treatment tool for the screening of HCC recurrence.

Other examples of cancer screening tools that have been implemented as part of various public health initiatives include, mammography for breast cancer screening, fecal occult blood assessment for colorectal screening, serum prostate specific antigen testing for prostate cancer screening, and cervical smear assessment for cervical cancer screening. Many screening programs have been implemented because it is generally perceived that the early identification of disease or disease progression would translate into health benefits, such as longer disease-free survival, higher quality of life years, and economic savings in the management of the diseases. For example, if cancers could be identified at an early stage or even at an asymptomatic stage, simpler treatment modalities or those with less side effects could be applied. For example, the tumor may still be at a stage where surgical removal could be considered.

In general, it is preferable to adopt tools that are noninvasive and with little side effects for screening. Invasive modalities or those with high potential for complications are reserved for individuals whose pre-test probability for the diseases is high enough to justify facing such risks during assessment. For example, liver biopsy is performed on individuals with very high index of suspicion of HCC, such as chronic HBV carriers or liver cirrhosis patients with a hypoechoic shadow shown on liver ultrasound.

In terms of the performance profile of the screening tests, it is preferable to have tests that either have a high positive predictive value (PPV) or a high negative predictive value (NPV). The actual preferred performance profile for any one screening indication is dependent on the purpose of the screening. Tests with high PPV are generally used to confirm or "rule in" a disease classification. Tests with a high NPV are generally used to exclude or "rule out" a disease classification. Some tests have both high PPV and NPV. These are usually tests that could offer a definitive classification, for example, tissue biopsies followed by histological examination.

D. Identification of Cancer-Specific Targets in Tumor Tissues for Screening

One could aim to detect the presence of any cancer-associated mutations originating from the genome of a cancer cell among plasma DNA for the detection of cancers. As demonstrated in the example of EBV DNA in NPC above, the high clinical sensitivity or detection rate of NPC using the plasma EBV DNA test is related to the ability to detect about 500 cancer-derived plasma DNA fragments per NPC cell, e.g., 300-600. To further enhance the sensitivity of the test or to perform one or more other screening tests, one may need to be able to detect 300 or more cancer-associated fragments per cancer cell (e.g., 400, 500, 600, 800, or 1,000 or more).

One possible way for having more than 500 cancer-specific targets for NPC, as well as to generalize this to other cancers and malignancies, would be the analysis of a set of subject-specific single nucleotide mutations, or mutations involving more than one nucleotide. To identify such subject-specific information, massively parallel sequencing of the tumor tissue of a cancer subject can be performed. The constitutional DNA of the subject can be sequenced as a reference for the identification of the mutations in the tumor tissue. The constitutional DNA can be obtained from any non-malignant cells of the subject, for example, but not limited to, blood cells and buccal cells. In addition to single nucleotide mutations, other cancer-specific or cancer-associated genetic and epigenetic changes (e.g., copy number aberrations and aberrant methylation) can also be used as targets for cancer detection.

Such changes can then be detected in a biological sample of the subject that may contain tumor DNA (e.g. plasma or serum, both of which contains cell-free DNA). In one embodiment, the aim is to assess the mutational load of the body through plasma DNA analysis. For this particular embodiment, the detection of cancer-specific mutations can be used for monitoring the progress of the subject after treatment because the tumor tissues would need to be obtained for the identification of the cancer-associated changes specific for the subject. The detection of the cancer-specific changes can be performed by allele-specific PCR, amplicon sequencing using massively parallel sequencing (e.g. using tagged-amplicon deep sequencing (Forshew et al. Sci Transl Med 2012; 4: 136ra68)), mass spectrometry analysis and microarray analysis, or ultra-deep sequencing, exhaustive sequencing and total template sequencing as described in some embodiments of this application.

In one embodiment, the sum (example of a mutational load) of the amounts of plasma DNA carrying each cancer-specific change can be determined and used to reflect the number of cancer cells in the body. The latter information would be useful for prognostication, monitoring and for assessment the response to treatment. In other embodiments, the mutational load can be determined as the product or the weighted mean of the amounts of the cancer-specific targets.

In some embodiments, the mutational load can be determined with little or no information about which mutations might exist in the sample, e.g., during an initial screen, as is described below. Further, a relative proportion of a mutation and the wildtype allele at a position can be used to infer the fractional concentration of tumor-derived DNA in the plasma sample.

III. Circulating Cell-Free DNA Mutational Load Assessment for Cancer Screening

To identify cancer mutations and determine a mutational load of an individual, embodiments can analyze a sample with circulating cell-free DNA. Tumors, cancers, and malignancies are known to release its DNA content into the circulation (Bettegowda et al. Sci Transl Med 2014; 6: 224ra24). Thus, the mutations associated with tumors, cancers, and malignancies could be detected in plasma and serum. Such mutations could also be detected in other body fluids, such as, but not limited to urine, other urogenital fluids, cervical lavage fluid, nipple discharge, saliva, pleural fluid, ascitic fluid and cerebrospinal fluid (Togneri et al. Eur J Hum Genet 2016; doi: 10.1038/ejhg.2015.281; De Mattos-Arruda et al. Nat Commun 2015; doi: 10.1038/ncomms9839; Liu et al. J Clin Pathol 2013; 66:1065-1069.).

The mutations could be detected in these body fluids because of the direct shedding of cells or cell-free DNA into the fluid from those organs that are in direct contact with the fluid, e.g., from the urinary (e.g. from the kidney or bladder) or genital (e.g. from the prostate) tract to the urine, transrenally from the plasma into the urine, from the brain to the cerebrospinal fluid, from the pancreas into pancreatic juice, from the gallbladder into bile, from the oropharynx to the saliva, from mammary cells to the nipple discharge fluid, from the abdominal organs to the ascitic fluid, or from the lungs to the pleural fluid. In addition, the mutations could be detected in the body fluids because they are partly derived from the filtration of plasma. Hence, contents in plasma, including the tumor-derived mutations from other organs more distant from the site of the fluid, could be detected in the body fluids.

The detection of mutations among cell-free nucleic acids in plasma, serum, and the other body fluids is attractive for the development of cancer screening tests because they provide access to the tumor-associated genetic and genomic changes relatively noninvasively and in lieu of the direct assessment of a tumor biopsy. In addition, nearly all forms of genetic and genomic changes associated with tumor, cancers, or malignancies have been detected among the cell-free nucleic acid population. Examples of cancer-associated changes or cancer-specific changes are provided herein. Cancer-specific generally refers to a change that comes from a cancer cell, and cancer-associated means the change can come from a cancer cell, or a premalignant lesion, or other tissues due to anatomical proximity, physiological association, developmental association or a reaction to the presence of the cancer.

Due to the noninvasive access to the tumor-associated genetic and genomic profile (especially determined from plasma and serum cell-free nucleic acids), if used as a screening test, the tumor-associated profile could be measured repeatedly, either within shorter interval (e.g. days or weeks) to "rule in" or "rule out" disease or over longer intervals, such as biennially, annually, or biannually.

Plasma DNA molecules naturally exist in the form of short DNA fragments (Yu et al. Proc Natl Acad Sci USA 2014; 111: 8583-8588). They are typically <200 bp long, and can fragment at certain cancer-associated locations, as is discussed in more detail below. The majority of the DNA molecules in human plasma originate from hematopoietic cells. When a person develops a non-hematopoietic malignancy, especially during the early stages, the tumor-derived DNA represents a minor fraction in plasma mixed with a background of non-tumor-derived hematopoietic DNA. The amount of tumor-derived DNA in a plasma sample could be expressed as a fraction of the total DNA or the number of genomic-equivalents or cell-equivalent of cancer cells. In the case of a hematopoietic malignancy, the fraction of malignancy-associated DNA in plasma would be expected to be higher than that in a non-hematopoietic malignancy and could be detected using the same embodiments described in this application.

In this application, we describe protocols that could be generically applied to the detection of any cancer as long as the tumor contributes DNA to the body fluid (Bettegowda et al. Sci Transl Med 2014; 6: 224ra24). The reason is because the embodiments described are not dependent on the detection of biomarkers that are typical of just a certain cancer type. The classification scheme used to differentiate individuals with and without cancer is based on mutational load assessment that could also be generically applied for the purpose of the detection of any cancer.

To develop a test for the screening of other cancers with high clinical sensitivity and specificity, the ability to detect a wide range and large number of mutations would be needed. There are several reasons to justify this test requirement. Unlike the association of EBV with NPC, most other cancers are not associated with a non-human genetic marker that could be distinguished from the non-cancer human DNA with relative ease. Therefore, to develop a screening test for the non-EBV related cancers, the test would need to detect the other varieties of cancer-associated changes.

A. Test Sensitivity Requirements (e.g., Breadth and Depth)

Based on the calculations above, to achieve the same sensitivity as the plasma EBV DNA test for NPC detection (Chan et al. Cancer 2013; 119: 1838-1844), the test would preferably need to be able to detect at least ~500 copies of plasma DNA bearing a cancer-associated change in order to achieve the detection of the equivalent DNA content of one tumor cell in the circulation. The NPC data is used as a model system to reason through the principles for achieving a clinically sensitive and specific cancer screening test. This could be achieved either by detecting 500 copies of one tumor-associated change, such as in the case of the plasma EBV DNA test, or one copy each of 500 different tumor-associated mutations, or a combination, namely multiple copies of a set of <500 mutations. Because plasma DNA fragments are generally <200 bp in length, one could assume that the detection of any one cancer-associated change would require the detection of one plasma DNA fragment bearing such a change, termed an informative cancer DNA fragment.

Some of those researchers skilled in the art have therefore developed tests to detect certain mutations in plasma as a means to detect cancer. For example, plasma detection of epidermal growth factor receptor mutations by digital polymerase chain reaction (PCR) has been used for the detection of non-small-cell lung cancer (Yung et al. Clin Cancer Res 2009; 15: 2076-2084). Panels including hundreds of other cancer-associated mutations, such as in oncogenes and tumor suppressor genes, have been developed for plasma DNA assessment. Theoretically, these tests should have achieved clinical sensitivities for the detection of those other cancers approaching performance like that of the plasma EBV DNA test for NPC. However, in practice, this is not the case.

1. Breadth

It is now appreciated that cancers are highly heterogeneous. The mutation profile varies greatly between cancers of different organs, varies greatly between different subjects with cancers of the same organ or even between different tumor foci in the same organ of the same subject (Gerlinger et al N Engl J Med 2012; 366: 883-892). Therefore, any one tumor-associated mutation is only positive in a small subset of any cancer subject. For example, the Catalogue of Somatic Mutations in Cancer (COSMIC) database documents the range of genetic mutations that have been detected in tumor tissues (cancer.sanger.ac.uk/cosmic).

FIG. 1 shows a table 100 of the top 28 most commonly identified mutations among cancers. The data show that the sum of the top 28 most prevalent mutations for cancers of any given organ is far from 100%. It is also noteworthy that different mutations could occur with each of the genes listed in FIG. 1. Therefore, if one assesses the prevalence of any one specific mutation among tumors, the number would be very low. Because the location of cancer mutations are so variable and unpredictable, in order to identify 500 different mutations in any one cancer subject, one could consider first analyzing a tumor biopsy. The identified mutations would then be used to inform what plasma DNA assays would be used for subsequent monitoring. However, the need for prior assessment of a tumor biopsy would preclude one from applying the plasma DNA test for primary or asymptomatic screening.

As shown in FIG. 1, only a proportion of each tumor type may exhibit any one of the top mutations. The data suggest that a large proportion of tumors do not feature any one of the top mutations listed in the COSMIC database. In other words, if one designs a cancer screening test based on the exclusive detection of the top mutations, many tumors would not be detected due to the absence of such mutations. These data suggest that the need to detect a large number of somatic mutations, as demonstrated by embodiments in this application, is important to realize a screening test that is generic to different tumors and yet could yield positive findings in a large proportion of the cancer population.

Thus, to develop a plasma DNA test for cancer detection or primary screening, one would need to scout through a much wider search space within the genome in order to collect enough mutations (e.g., copy number aberrations and sequence variants relative to a reference genome, such as a constitutional genome or parental genomes) or other cancer-specific or cancer-associated changes (e.g., methylation changes) to make up the sum of 500 cancer-specific plasma DNA fragments per cancer cell. Noting the data shown in FIG. 1, assuming the chance of any one well-documented cancer-associated mutation occurring in any one tumor is 1%, the test would need to target the detection of 50,000 putative mutation sites in order to have at least 500 mutations detected per tumor (based on Poisson probability distribution). 500,000 putative mutations or cancer-associated changes would need to be tested in order to have at least 5,000 mutations or cancer-associated changes represented for any one tumor. On the other hand, if the chance of any one well-documented cancer-associated mutations or changes occurring in any one tumor is 0.1%, then 50,000 mutations or changes would need to be tested in order to have at least 50 mutations or changes represented for any one tumor.

Therefore, to maximize the cancer detection rate, or clinical sensitivity, of the cancer screening test, the test would need to achieve a broad survey of plasma DNA fragments in a sample in order to identify enough fragments bearing any one type of cancer-associated change or mutation. The breadth of the survey could be achieved either with the use of genomewide approaches or targeted approaches that cover a large fraction of the genome, for example enough to cover at least 50,000 targets.

2. Depth

The depth of the survey also matters. Depending on the number of mutations detected per tumor, multiple plasma DNA fragments that bore that mutation would need to be detected to reach a specified threshold, e.g., 500 informative cancer DNA fragments for each genome-equivalent of cancer cell. For example, if only one mutation is identified in a particular tumor, then 500 plasma DNA fragments covering that mutation would be needed. On the other hand, if 50 different mutations are present in the tumor, on average, one would need to detect at least 10 informative cancer DNA fragments covering each one of those 50 mutations.

Tumor DNA typically represents a minor DNA population in plasma. Furthermore, some cancer-associated changes are heterozygous in nature (i.e. with one change per diploid genome). Thus, to detect 10 copies of informative cancer DNA fragment (i.e. plasma DNA fragments that carry at least one cancer-associated change) per locus, one would need to analyze at least 100 molecules from the locus in a plasma sample with 20% tumor DNA fraction. Hence, the ability to detect multiple plasma DNA fragments covering any single mutation site is dependent on how deep the plasma sample is surveyed. Yet, there is only a finite number of cancer cell genomes in the plasma sample, which affects both the required depth and breadth of the plasma DNA analysis.

For illustration of the detection of early cancers, assume one aims to develop a test or protocol that could detect a tumor fraction of 1% in a sample. Given that there are typically 1,000 genome-equivalents of DNA in every milliliter of plasma, there would be 10 cancer cell-equivalent of DNA in a milliliter sample with 1% tumor DNA fraction. This means that even if one could detect every single cancer-specific DNA fragment in the sample, there would only be a maximum of 10 genome-equivalents of any one cancer-associated change that would be available for detection. Accordingly, even if one has prior knowledge that a particular mutation is present in a tumor, its targeted detection would only provide a signal of 10 genome-equivalents in the best-case scenario, which may lack the analytical sensitivity for robust detection of a cancer at 1% fractional concentration. If the mutation to be detected is heterozygous, there would only be 5 plasma DNA fragments showing this mutation.

In the best-case scenario with 1% tumor DNA fraction, the depth of the analysis at this mutation site would need to be covered at least 1,000 times to be able to detect the 10 genome-equivalents of plasma DNA with the mutation. In this situation, the breadth of the analysis would need to make up for the relatively low number of copies detected per mutation site. The selective detection of a handful or even just hundreds of mutation sites is unlikely to be able to achieve the sensitivity required for a screening test to detect early cancer.

3. Other Problems

In addition, in routine analyses, the detection performance of any one assay is far from the best-case scenario. For example, there could be loss or reduction in plasma DNA templates and informative cancer DNA fragments during the sample processing steps, DNA sequencing library preparation steps, and probe based target capture hybridization process. Some steps may introduce biases in the relative proportions among different mutations and between the cancer and non-cancer derived DNA. For example, PCR amplification of target sequencing libraries, genomic DNA sequencing libraries, and amplicon sequencing could introduce GC biases as well as create PCR duplicates. For massively parallel DNA sequencing, errors in the identification of a sequenced fragment could result from sequencing errors arisen during PCR amplification or during the sequencing, during base-calling, or due to alignment errors. Lastly, the signal detection mechanism of the analysis platform may have a detection limit before a confident positive readout could be provided for the detection of a mutation (e.g., 5 mutant fragments might be needed for a detectable signal). All these factors mean that in practice, the breadth and depth requirements of the plasma DNA analysis may need to be even higher than the theoretical ideal scenarios discussed.

In essence, the discussion so far suggests that the sensitivity requirements of the cancer screening test is reaching the limitations of what molecular analysis platforms could achieve in practice. Biologically, it has been reported that the number of somatic mutations harbored by a malignant tumor ranges between about 1,000 to several 10,000s (Lawrence et al. Nature 2013; 499: 214-218). Based on our data, depending on the fractional concentration of tumor DNA in the plasma sample, one might just have enough informative cancer DNA fragments in the finite plasma sample (typically <10 milliliters plasma would be obtained per blood draw) to achieve early noninvasive cancer detection.

Therefore, to practically attain the sensitivity requirements of the cancer screening test, one would need to maximize the cancer information content that could be obtained in each plasma sample. In this application, we describe processes that can achieve the effective breadth and depth needed to reach the sensitivity requirements of the cancer screening test. In various embodiments, ultra-deep and broad sequencing, exhaustive, or total template sequencing is performed. PCR-free massively parallel sequencing may be performed to increase the cost-effectiveness of the ultra-deep and broad sequencing, exhaustive, or total template sequencing. The ultra-deep and broad sequencing, exhaustive, or total template sequencing can be achieved through single molecule sequencing.

Some embodiments can increase the number of accessible informative cancer DNA fragments by the combined detection of a variety of cancer-specific or cancer-associated changes, for example, single nucleotide mutations, in combination with cancer-specific or cancer-associated DNA methylation signatures (e.g. location of 5-methycytosine and hydroxymethylation), cancer-specific or cancer-associated short plasma DNA molecules, cancer-specific or cancer-associated histone modification marks, and cancer-specific or cancer-associated plasma DNA end locations. Certain cancer-specific or cancer-associated changes may be used as filtering criteria in identifying mutations.

B. Specificity Requirements (e.g., Filtering Criteria)

As described above, it is desirable to detect as many informative cancer DNA fragments as possible. But, it can be difficult to accurately detect such informative cancer DNA fragments given the level of noise (e.g., errors from various sources) present in current sequencing techniques.

1. Specificity of Identified Mutations

In order to achieve a high PPV or high NPV, the cancer screening test would need to show a high specificity profile. High specificity could be achieved at a number of levels. The specificity of the mutations and any cancer-associated changes to be detected would need to be as specific for cancer as possible. This could be achieved by, but not limited to, scoring a genetic or genomic signature as positive only when there is high confidence that it is cancer associated. This could be achieved by including signatures that have been previously reported in other cancers. For example, one can focus particularly on signatures that are prevalent in the cancer type that the individual is predisposed to, based on his or her demographic profile. Or, one can pay particular attention to mutational signatures that are associated with the mutagenic exposure that a subject has been exposed to (Alexandrov et al. Nature 2013; 500: 415-421). This could also be achieved by minimizing the number of sequencing and alignment errors that may be misidentified as a mutation. This may be achieved by comparing to the genomic profile of a group of healthy controls, and/or may be achieved by comparing with the person's own constitutional DNA.

These criteria could be applied as filtering criteria to assess the likelihood of a plasma DNA fragment being derived from the tumor and hence qualifies to be an informative cancer DNA fragment. Each filtering criterion could be used individually, independently, collectively with equal weighting or different weightings, or serially in a specified order, or conditionally depending on the results of the prior filtering steps. For conditional usage, a Bayesian-based approach can be used, as well as a classification or decision tree based approach. An individual use means just any one criterion. An independent use may involve more than one filtering criterion, but each filtering criterion does not depend on the application of another filtering criterion (e.g., parallel application can be performed), in contrast to a serial application in specific orders. As an example of collective usage using weightings, machine learning techniques can be used. For example, supervised learning can use measured mutational loads of samples with known classifications to train any models. Sequencing data from a large number of individuals (e.g. hundreds, thousands, or millions) can be used to train the models. In a simpler form, such known samples can be used to determine threshold values for one or more scores determined from the filtering criteria to determine whether a mutation is valid or not.

In one embodiment, if a plasma DNA fragment fulfills some or all of the criteria, one may deem it to be an informative cancer DNA fragment, while the others that do not fulfill some or all can be deemed a non-informative plasma DNA fragment. In another embodiment, each plasma DNA fragment could be given a weighting of informativeness of being an informative cancer DNA fragment depending on how strongly it fulfills the list of criteria. The higher the confidence that the fragment is tumor-derived, the higher the weighting. In one embodiment, the weighting can be adjusted based on the clinical profile of the test subject (e.g. sex, ethnicity, risk factor for cancer, such as smoking or hepatitis status, etc.).

A DNA fragment could be given a higher weighting of informativeness or cancer-specificity if it shows more than one cancer-specific change. For example, many cancers are globally hypomethylated, especially at the non-promoter regions. Cancer DNA has been shown to be shorter than the non-cancer DNA in plasma. Tumor-derived plasma DNA fragments tend to fragment at some specific locations. Therefore, a plasma DNA fragment that is short in size (for example <150 bp) (Jiang et al. Proc Natl Acad Sci USA 2015; 112: E1317-1325), with one or both ends that fall on cancer-associated end locations, shows a single nucleotide mutation, and localizes to a non-promoter region, and has a hypomethylated CpG site would be deemed as more likely to be cancer-associated. The detection of hypomethylated DNA could be achieved with the use of bisulfite DNA conversion or direct single molecule sequencing that could distinguish methyl-cytosine from non-methyl-cytosine. In this application, we describe processes, protocols and steps to increase the specificity in the identification of informative cancer DNA fragments. For example, one or more filtering criteria can be used to increase the specificity.

2. Specificity of Mutational Load

On another level, the specificity of the cancer screening test could be achieved by assessing if the amount (e.g., number) of cancer-associated changes detectable in plasma of patients with cancer reflects a mutational load commensurate with that expected for cancer. In one embodiment, one could compare the mutational load in plasma with the mutational load measured in the constitutional DNA, e.g., when the mutational load is determined with respect to a reference genome. In other embodiments, one could compare the mutational load in plasma with that observed in plasma of the subject at a different time, or of a cancer patient with known prognosis (good or bad) or stage of cancer, or of a healthy cancer-free population. The reference population may be age- or sex- or ethnicity-matched, as it has been reported that the mutational load in the body or in tissues increases with age even in persons not shown to have cancer (Slebos et al. Br J Cancer 2008; 98: 619-626). In this application, we describe how broad and deep the plasma DNA analysis would need to be performed to capture an adequate mutational load to enhance the differentiation between cancer subjects from the healthy population. Thus, not all of the DNA fragments in the plasma sample need to be detected to achieve cancer detection, e.g., if a sample has sufficient mutational information.

Whether an observed mutational load is suggestive of cancer could, in one embodiment, be based on cancer-specific reference ranges. In has been reported that cancers of different organs tend to harbor an expected range of mutation load. The number may range from 1,000 to several 10,000s (Lawrence et al. Nature 2013; 499: 214-218). Thus, if the plasma DNA cancer screening test shows evidence that a person's mutational load is approaching numbers in the range of any cancer group, a classification for high risk of cancer could be made (FIGS. 44, 45A-45C, and 46A-46C of section VIII). In another embodiment, a classification for cancer could be made if the mutational load in the plasma of a person is significantly higher than a reference range established from a healthy population without cancer.

Evidence for significantly higher mutational load could be based on statistical distributions, e.g., more than three standard deviations from the mean of the control reference data, or a number of multiples of the median of the control reference data, or greater than a particular percentile (for example the 99$^{th}$ centile) of the control reference data, or at least 1 or 2 or 3 orders of magnitude greater than the mean, median, or 99$^{th}$ centile of the control reference data. Those skilled in the art would be able to identify various statistical means to identify statistically significantly increased mutational load. In another embodiment, the classification could take into account variables that have been shown to affect the sensitivity and specificity profiles of the cancer screening test, such as the measured or presumed or inferred tumor DNA fraction of the sample, sequencing depth, sequencing breadth, and sequencing error rates (FIGS. 44, 45A-45C, and 46A-46C of section VIII).

The mutational load can be determined in various ways. The mutational load could be expressed as the number of mutations detected. The number of mutations could be normalized to the amount of sequencing data obtained, e.g. expressed as a percentage of the sequenced nucleotides or a density of mutations detected for the amount of sequencing performed. The number of mutations could also be normalized to the size of the human genome, e.g. expressed as a proportion of the genome or a density per region within the genome. The number of mutations could be reported for each occasion when mutation load assessment is performed or could be integrated over time, e.g. the absolute change, percentage change or fold change compared to a previous assessment. The mutational load could be normalized to the amount of the sample (e.g. volume of plasma) analyzed, to the amount of DNA obtained from the sample, or the amount of analyzable or sequenceable DNA. In one embodiment, the mutational load can be normalized to a biometric parameter of the tested subject, e.g. weight, height, or body mass index.

In this application, we describe how broad and deep the plasma DNA analysis would need to be to capture an adequate mutational load to enhance the differentiation between a subject with cancer from a population without cancer, hence, to achieve effective mutational load assessment.

IV. Ultra-Deep and Broad Sequencing

As explained in detail earlier, there is a need for ultra-deep and broad sequencing to achieve the performance profiles needed for the cancer screening test or the effective identification of fetal de novo mutations. In this application, we show a number of embodiments for achieving ultra-deep and broad sequencing. Such embodiments include, but not limited to, exhaustive sequencing, total template sequencing, PCR-free sequencing, single molecule sequencing (a type of PCR-free sequencing), and targeted sequencing. A combination of approaches may be used to achieve the needed depth and broadness. Such a combination can be used for a screening program as a whole, or for screening a particular individual or groups of individuals.

Figure 4B:
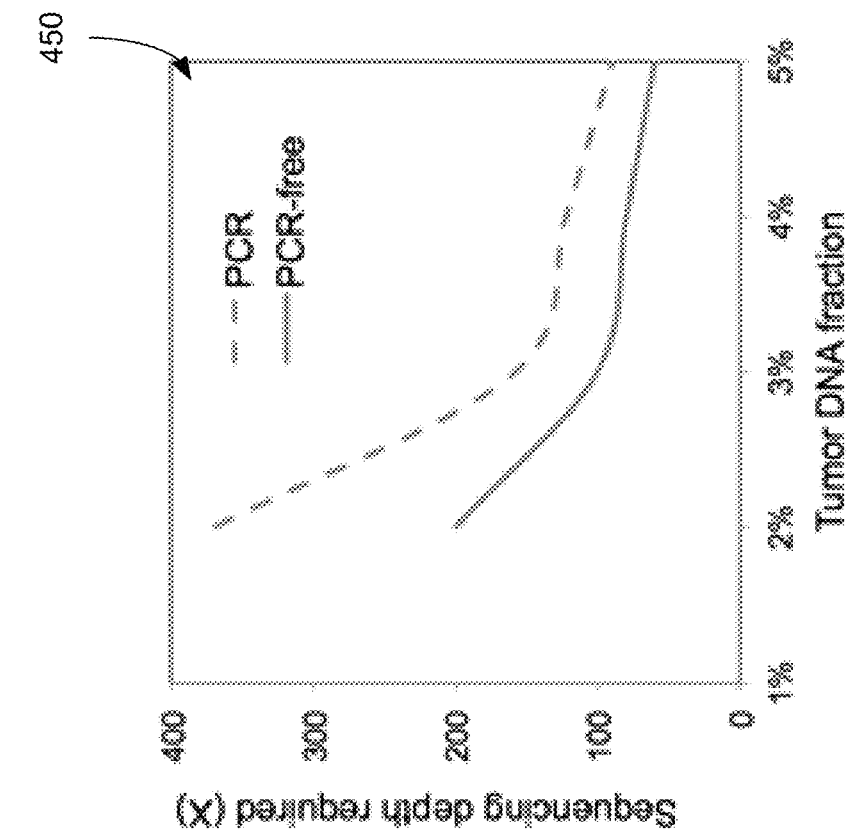
FIGS. 4A and 4B show a comparison between the sequencing depth required for PCR and PCR-free protocols to detect cancer-associated mutations in the plasma of a cancer subject at various tumor DNA fractions according to embodiments of the present invention.

For the purpose of cancer screening, to detect the cancer-associated mutations from plasma DNA sequencing, the sequencing depth would affect the ability to differentiate true cancer mutations and false-positives due to sequencing errors. A higher sequencing depth would be required when the tumor DNA fraction in the plasma is lower (FIG. 4B). Using a dynamic cutoff analysis (described in a later section), when the tumor DNA fraction is 2%, a sequencing depth of 200 folds would be able to detect 5.3% of the cancer associated mutations. The number of mutations detected would be higher than the expected number of false-positives, assuming that random sequencing errors occur with a frequency of 0.3%. The portion of the genome to be searched would be dependent on the expected number of mutations in the tumor tissue.

The portion of the genome to be searched would need to be large enough to obtain sufficient number of mutations to be detected. This breadth parameter would be dependent on the desired lower limit of detection of tumor DNA fraction and the type of cancer to be screened for. For example, in melanoma, the median frequency of mutation is around 10 per 1 Mb. In other words, there would be approximately 30,000 mutations in a genome. Assuming that the tumor DNA fraction is 2% and 1/10 of the genome is searched, it is expected that approximately 159 mutations would be detected by plasma DNA sequencing at 200×. On the other hand, if rhabdoid tumor is the target to be screened, the median frequency of mutations is only 0.2 per 1 Mb. Thus, the search of 1/10 of the genome would yield approximately 3 cancer mutations when the tumor DNA fraction is 2%. This number is not sufficient to be differentiated from sequencing errors.

FIG. 2 is a table 200 showing an expected number of mutations to be detected for different tumor DNA fractions, sequencing depths, number of mutation per genome and the fraction of genome searched. The expected number of false-positives is <10 for the whole genome for each case based on a dynamic cutoff analysis (or other suitable filtering analysis) and a sequencing error rate of 0.3%. Therefore, when the number of detectable mutations (e.g., based on depth and breadth) is larger than 10, embodiments would be useful for differentiating real cancer mutations from false positives.

As shown in the data of table 200, the portion of the genome to be analyzed would be dependent on the expected tumor fraction and the frequency of somatic mutations in the tumor. With the analysis of 5% of the genome, the number of mutations would be much higher than the number of false-positives when the tumor fraction is 10%, the frequency of mutations is 10 per Mb, and the sequencing depth is 200 folds. Using simulation analysis, we deduced that the number of mutations detected would be sufficient to discriminate from random sequencing errors even when on 0.1% of the genome is searched. For other frequency of mutations and sequencing depths, higher portions of the genome may need to be analyzed, e.g., 1%, 5%, 10%, and 20% of the genome can be analyzed by aligning sequence reads to a reference genome.

For the purpose of cancer screening, it is not necessary to identify 100% of the cancer-associated mutations. In one embodiment, one only has to show that a particular individual has a higher number of mutations detected in plasma (or other biological sample) than that in a reference control population without cancer. However, for this strategy to be highly accurate, the proportion of true mutations detected by a mutational load assessment protocol would need to be as high as possible (or the proportion of false positives needs to be as low as possible), so that the high number of variants detected by the assessment is reflective of the presence of cancer. If this could not be achieved, the high number of putative mutations detected in a sample may simply be reflective of a high number of false-positive variants and hence would not allow the discrimination of a subject with cancer and those without cancer. Therefore, embodiments in this application describe how to reduce the detection of false positives and how to increase the detection of true mutations to achieve effective mutational load assessment.

Ultra-deep and broad sequencing can be achieved by exhaustive sequencing or other means, e.g., light (non-exhaustive) sequencing of multiple targeted sequencing panels. Light sequencing can be used to minimize PCR duplicates so one can obtain the required depth. Multiple targeted sequencing panels can be used to provide broad coverage across the genome.

A. Exhaustive Sequencing and Total Template Sequencing

To develop an effective cancer screening test for the early identification of cancer and the identification of cancer at early stages, one would ideally obtain as much cancer relevant information from the plasma sample as possible. There are a number of issues hindering one's ability to obtain cancer-relevant information from the plasma sample: (1) the sample to be analyzed has a finite volume; (2) the tumor fraction in a particular biological sample may be low during early cancer; (3) the total amount of somatic mutations per tumor available for detection are on the order of 1,000 to 10,000; and (4) the analytical steps and technical processes would lead to a loss in information content. Therefore, one should try to minimize the loss of any cancer-related information content in the plasma sample that is amenable for detection.

Due to limitations in the sample preparation steps, sequencing library preparation steps, sequencing, base-calling and alignment, not all plasma DNA molecules in a sample would be analyzable or sequenceable. Exhaustive sequencing refers to procedures implemented to maximize the ability to transform as many of the informative DNA molecules (e.g., ones with mutations) in a finite sample into analyzable or sequenceable molecules. Several processes could be adopted to achieve exhaustive sequencing.

What constitutes the informative DNA population can vary based on what is being tested. For cancer testing, it would be the informative cancer plasma DNA fragments. For prenatal testing, it would be the fetal-derived DNA molecules in maternal plasma. For transplantation monitoring, it would be the donor-derived molecules in the plasma of the transplant recipient. For detecting other diseases, it would be those plasma DNA molecules derived from the organ or tissue or cells with the pathology. For detecting an abnormal biological process that involves mutations, it would be those plasma DNA molecules derived from the organ or tissue or cells involved in the process, e.g. the brain in ageing. Examples of such biological processes can include aging, genetic predisposition to mutations (e.g. xeroderma pigmentosum), mutagenic influences from the environment (e.g. radiation or UV exposure), or toxins and effects from drugs (e.g. cytotoxic agents). As to sample type, for testing of DNA in a urine sample, it could be cancer DNA molecules that have passed transrenally from the circulatory system (e.g. from plasma) into the urine sample (Botezatu et al. Clin Chem 2000; 46: 1078-1084). For other cancer, it could be cancer DNA molecules that have passed from a cancer of the urogenital tract (e.g. from the bladder or the kidneys) into the urine sample.

To be as exhaustive as possible, one could adopt any one, all or a combination of processes: (1) Use DNA preparation protocols that reduce DNA loss or have high DNA library conversion efficiency or sequencing efficiency; (2) Bypass the problem of PCR duplicates by using PCR-free DNA preparation protocols; (3) Reduce sequencing errors by using PCR-free DNA preparation protocols; (4) Reduce alignment errors by adopting effective alignment algorithms, e.g. a realignment strategy. By adopting some or all of these measures, the degree of loss in plasma DNA information content as well as wastage of sequencing resources can be reduced, so that ultra-deep and broad sequencing could be achieved more cost-effectively.

After applying such measures of exhaustive sequencing intent, the amount of cancer-relevant signal or informative cancer DNA fragments may become so effective that information from just a proportion of the sample is already adequate for reaching the classification to "rule in" or "rule out" cancer. For example, as shown in a later example of the mutational load comparison between a plasma sample from a HCC patient and from a cord blood plasma sample, the data at 75× depth was already adequate to clearly distinguish the HCC case from the cord blood plasma of a neonate without cancer. 220× of data was generated for the HCC plasma sample. But 75× of data was already enough because the number of informative cancer DNA fragments detected using the procedures for exhaustive sequencing intent was already adequate and of adequate quality for the positive classification of cancer.

If one indeed fully consumes the sequenceable plasma DNA molecules from the finite sample, this act could be termed "total template sequencing". This refers to one spectrum of exhaustive sequencing. For example, all the plasma DNA libraries were sequenced from the HCC case to reach the depth of 220×.

One can also perform exhaustive sequencing using a single molecule sequencer (Cheng et al. Clin Chem 2015; 61: 1305-1306). Examples of such single molecule DNA sequencers, include, but not limited to, a sequencer manufactured by Pacific Biosciences using the Single Molecule Real-Time DNA sequencing technology (www.pacificbiosciences.com/) and a nanopore sequencer (e.g. one manufactured by Oxford Nanopore (www.nanoporetech.com/)). A number of such single molecule sequencing platforms would allow one to directly obtain epigenetic information from the sequenced molecule (e.g. DNA methylation patterns) (Ahmed et al. J Phys Chem Lett 2014; 5: 2601-2607). As epigenetic aberrations have been described in cancer, having such epigenetic information would further enhance the screening, detection, monitoring and prognostication of cancer. For example, filtering techniques based on methylation are described below.

Another embodiment whereby epigenetic information can be obtained from the sequencing data is to perform bisulfite conversion of the template DNA, followed by DNA sequencing. Bisulfite conversion is a process whereby a methylated cytosine would remained unchanged, while an unmethylated cytosine would be converted to uracil. The latter would be read as a T residue during DNA sequencing. Bisulfite sequencing, a form of methylation-aware sequencing, can then be performed on a sequencing library for the bisulfite converted template DNA. Alignment can then be performed using approaches known to those skilled in the art, for example the method by Jiang et al. (PLoS One 2014; 9: e100360).

When sequencing of cell-free DNA is used for cancer, one can combine many types of molecular information from the sequencing results, namely, viral genomic sequences in plasma (for cancer associated with viral infections, e.g. EBV for NPC), tumor-associated single nucleotide variants, copy number aberrations, and epigenetic information (e.g. DNA methylation (including 5-methylcytosine profile and hydroxymethylation), histone acetylation/methylation changes, etc.). Such a combination of information can make the analysis more sensitive, specific, and clinically relevant.

B. PCR-Free Protocol

For the detection of any cancer-associated change in the plasma (or other sample type containing cell-free DNA) of a tested subject, the probability of detecting such a change should theoretically increase with the increase in the number of DNA molecules analyzed. Here we use a hypothetical example to illustrate this principle. Assume that 20% of the plasma DNA in a cancer subject is derived from the tumor, and the tumor has a point mutation at a particular nucleotide position. The mutation occurs only in one of the two homologous chromosomes. As a result, 10% of the plasma DNA covering this particular nucleotide position would carry this mutation. If we analyze one DNA molecule covering this nucleotide position, the probability of detecting the mutation would be 10%. If ten plasma DNA molecules covering this nucleotide change are analyzed, the probability of detecting the mutation would increase to 65.1% (Probability=$1-0.9^{10}$). If we further increase the number of molecules being analyzed to 100, the probability of detecting the mutation would increase to 99.99%.

This mathematical principle can be applied to predict the probability of detecting cancer-associated mutations when massively parallel sequencing is used for the analysis of plasma DNA from cancer subjects. However, typical massively parallel sequencing platforms used for sequencing plasma (e.g. the Illumina HiSeq2000 sequencing system with the TruSeq library preparation kit), PCR amplifications would be performed on the template DNA before sequencing.

Amplification refers to processes that result in increases (more than 1-fold) in the amount of template DNA when compared with the original input nucleic acid. In this application, amplification processes are steps performed during library preparation before the DNA template analysis step, e.g. sequencing. With amplification, the amount of template DNA available for analysis would increase. In one embodiment, amplification can be performed using PCR, which involves cyclic changes in temperature. In another embodiment, amplification can be performed using isothermal processes. We show in some embodiments that the amplified template DNA decreases the efficiency of achieving mutational load assessment. Clonal expansion steps that occur during the analysis step, e.g. bridge amplification during sequencing-by-synthesis, are not considered as an amplification because it does not result in extra sequence reads or sequence output.

When using PCR, the sequencing depth (i.e. the number of sequence reads covering a particular nucleotide) does not directly reflect how many plasma DNA molecules covering that particular nucleotide are analyzed. This is because one plasma DNA molecule can generate multiple replicates during the PCR process, and multiple sequence reads can originate from a single plasma DNA molecule. This duplication problem would become more important with i) a higher number of PCR cycles for amplifying the sequencing library; ii) an increased sequencing depth, and iii) a smaller number of DNA molecules in the original plasma sample (e.g. a smaller volume of plasma).

In addition, the PCR step introduces further errors (Kinde et al. Proc Natl Acad Sci USA 2011; 108: 9530-9535) because the fidelity of a DNA polymerase is not 100%, and occasionally, an erroneous nucleotide would be incorporated into the PCR daughter strand. If this PCR error occurs during the early PCR cycles, clones of daughter molecules showing the same error would be generated. The fractional concentration of the erroneous base may reach such a high proportion among other DNA molecules from the same locus that the error would be misinterpreted as a fetal-derived or tumor-derived mutation.

Here, we reason that the use of a PCR-free protocol for massively parallel sequencing would allow the more efficient use of sequencing resources, and it can further enhance the obtaining of information from the biological sample. In one embodiment, all the DNA molecules in a plasma sample are to be sequenced in a sequencing analysis using a PCR-free protocol during the massively parallel sequencing analysis. One PCR-free protocol that can be used is that developed by Berry Genomics (investor.illumina.com/mobile.view?c=121127&v=203&d=1&id=1949110). One can also use other PCR-free protocol such as that marketed by Illumina (www.illumina.com/products/truseq-dna-pcr-free-sample-prep-kits.html). Here we use an example to illustrate the principle.

For illustration, we first assume that all plasma DNA fragments are 150 bp in size, which is consistent with plasma DNA fragments generally being less than 200 bp, as mentioned above. Therefore, each diploid human genome would be fragmented to 40 million plasma DNA fragments. As there are about 1,000 diploid human genomes in a milliliter of plasma, there would be 40 billion plasma DNA fragments in 1 mL plasma. If we sequence 40 billion DNA fragments from 1 mL of plasma, we would expect that all the DNA molecules would have been sequenced. For illustration, if one uses an Illumina HiSeq 2000 system that can produce 2 billion reads per run, one would need 20 runs to achieve this amount of sequencing, which may be reduced with higher throughput platforms.

The total DNA concentration in the plasma sample can be determined using, for example but not limited to, digital PCR or real-time PCR before the sequencing analysis. The total DNA concentration can be used to determine the amount of sequencing required to sequence all analyzable or sequenceable DNA molecules in the sample. In other embodiments involving other degrees of exhaustive sequencing, one can sequence more than 20%, 25%, 30%, 40%, 50%, 60%, 75%, 90%, 95%, or 99% of the DNA molecules in a plasma sample, all of which are examples of exhaustive sequencing.

Key determinants for the percentage of DNA molecules to be sequenced include the amount of mutations, tumor fraction in the sample, and DNA library yield. The number of potentially sequenceable molecules in a sequencing library can be determined based on the volume, concentration, and conversion efficiency of the library. The number of DNA fragments required to be sequenced can be determined based on the desired detectable limit of tumor fraction and the expected number of mutations in the tumor. Based on these two numbers, the portion of the library to be sequenced can be determined.

An advantage of using a PCR-free protocol for exhaustive sequencing is that we can directly infer the absolute quantities of any target molecules in the sample rather than determining a relative amount to other reference targets that are sequenced in the same reaction. This is because each sequence read represents the information from one original plasma DNA molecule. In fact, if PCR amplification is used with ultra-deep and broad sequencing, the amount of target molecules relative to each other would drift further apart from the true representation. The reason is due to the generation of PCR duplicates as a result of the PCR amplification as well as due to amplification biases where some genomic regions are better amplified than others.

PCR amplification of sequencing libraries is commonly carried out in most existing protocols for massively parallel sequencing because this step can increase the number of molecules in the sequencing libraries so that the sequencing step can be performed more easily. A PCR duplicate (replicate) is a clonal product of an original template DNA molecule. The presence of PCR duplicates hinders the achievement of ultra-deep and broad sequencing. The proportion of sequence reads coming from PCR replicates would increase with the amounts of sequencing performed (sequencing depth). In other words, there would be diminishing return in unique information content as one performs sequencing more deeply. Hence, sequencing of PCR replicates would, in many scenarios, lead to a waste of sequencing resources. This would ultimately mean that much more sequencing is needed to reach the same breadth and depth of genomic coverage when compared with a PCR-free protocol. Thus, the costs would be much higher. In fact, in some instances, the proportion of PCR duplicates can be so high that a preferred breadth and depth of coverage could never be reached in practice.

This is counter-intuitive to those skilled in the art. Traditionally, PCR amplification, including whole genome amplification, is performed to provide more genetic material from a finite sample for more molecular analyses to be performed. Our data show that such an amplification step can be counter-productive. This is particularly counter-intuitive for plasma DNA analysis.

Plasma DNA is known to contain low abundance of DNA at low concentration, as is also true for other samples comprised of cell-free DNA. Thus, one would not think more information could be obtained without amplification of the scarce amount of DNA. In fact, in our amplification based library preparation protocol, we typically obtain 150 to 200 nM of adaptor ligated DNA library per 4 mL plasma. But as shown for the examples in this application, only 2 nanomoles of adaptor ligated DNA libraries are obtained from an equivalent amount of plasma volume. One would imagine such low amounts would be an obstacle for one to get more genomic information, and hence might be induced to perform an amplification step prior to analysis. Such an amplified library would create significant problems as a significant proportion of such a library would consist of PCR duplicates.

Furthermore, with such an amplified library, one could not practically perform total template sequencing to obtain as much information as possible from the 4 mL plasma sample (because a fixed amount of library is applied per sequencing run and an extreme number of runs would be needed to consume the library). As shown in our data, about 20 Illumina sequencing runs are needed to fully consume the PCR-free libraries of the HCC and pregnant cases that we have studied. If PCR or amplification based library construction protocols were used instead, 100 times the amount of sequencing, meaning some 2000 runs, would need to be performed. In other words, with an amplified library, one is creating duplicated molecules that would consume a significant part of the sequencing power. In contrast, the 2 nanomoles of library from the PCR-free protocol can be readily consumed, which is equivalent to exhausting the analyzable information from the 4 mL plasma sample.

Being able to use up a reasonable proportion of the 4 mL plasma sample is important. As illustrated with some calculations presented earlier, the number of genome-equivalents of cancer DNA in the plasma sample is low during early cancer and one needs to be able to seize the detection of as many of these cancer genome-equivalents in the plasma sample as possible. Assume one is able to achieve cancer classification with performing 10 runs of Illumina sequencing of a plasma DNA sample using a PCR-free library preparation protocol. These 10 runs would have consumed half of the sequencing library. This correlates with having made use of the analyzable content from half the plasma sample, namely 2 mL, to achieve cancer classification. On the other hand, 10 runs performed on a PCR-amplified library of the same sample would be equivalent to just consuming 0.5% of the library (because there is generally a 100 times amplification in the library yield of the PCR-amplified protocol). This correlates with having made use of the analyzable content from just 0.02 mL of the original 4 mL plasma sample, and the amount of data obtained would not be sufficient for achieving cancer classification. Thus, it is counter-intuitive that with the use of less DNA library produced without PCR amplification that more cancer-relevant information could be obtained per fixed amount of sequencing.

Those skilled in the art have shown that PCR duplicates, also known as PCR replicates, could be removed with a bioinformatics procedure that identifies any sequence reads that show identical start and end nucleotide coordinates. However, as will be shown in a later section, we have now identified that the plasma DNA fragment end locations are not random, and thus erroneous filtering would occur. Using a PCR-free protocol without applying a bioinformatics step to filter sequence reads with the same start and end nucleotide coordinates, we identified a small percentage of sequence reads (typically <5%) with identical start or end coordinates or both. This observation is a result of the non-random nature of plasma DNA cutting. Embodiments can incorporate the identification of cancer-specific end locations as a filtering criterion to identify informative cancer DNA fragments. The adoption of a PCR-free protocol would facilitate such analysis and the use of this criterion. Furthermore, this also means that the prior practice of removing sequence reads with identical start and end nucleotide coordinates in fact has removed usable informative cancer DNA fragments resulting in loss of cancer-related information content from the plasma DNA sample.

The sequencing error rate of the Illumina sequencing platforms is about 0.1% to 0.3% of sequenced nucleotides (Loman et al. Nat Biotechnol 2012; 30: 434-439; Kitzman et al. Sci Transl Med 2012; 4: 137ra76). The reported error rates for some other sequencing platforms are even higher. As has been shown that a sequencing error rate of 0.3% is not trivial and has created an obstacle for researchers from identifying fetal de novo mutations (Kitzman et al. Sci Transl Med 2012; 4: 137ra76) or cancer-specific somatic mutations in plasma with very high accuracy. This error rate is even more relevant for ultra-deep and broad sequencing. 0.3% errors in a sequencing data set with a depth of 200× translates to 200 million errors.

A proportion of such sequencing errors are generated by the PCR amplification steps during the pre-sequencing DNA library preparation steps. By using a PCR-free protocol for library preparation, this type of errors could be reduced. This would render the sequencing more cost effective because less reagents could be spent on sequencing these artefacts and less bioinformatics time spent on processing these errors. In addition, the true positive fetal de novo mutations and cancer-derived somatic mutations could be identified more specifically among less false-positives at less sequencing depth than otherwise if PCR amplification was involved. In fact, these advantages have not been apparent to other researchers (see next section).

C. Results of Sequencing with and without Pre-Amplification of Sequencing Libraries We performed a simulation analysis to compare the amount of sequencing required for detecting cancer-associated mutations in plasma for protocols with and without pre-amplification of sequencing libraries with PCR. To determine the proportion of sequence reads from PCR replicates, i.e. sequencing a molecule more than one time, we have used the following assumptions: (1) There are 500 genome-equivalents of DNA in 1 mL of plasma; (2) DNA is extracted from 2 mL of plasma with 50% yield; (3) 40% of the extracted DNA can be successfully converted into a sequencing library; (4) 10 cycles of PCR were performed for the pre-amplification and the PCR efficiency is 100%; (5) The fragmentation pattern for the pre-amplified and non-amplified libraries are identical; (6) The length of plasma DNA is 166 bp.

Figure 3:
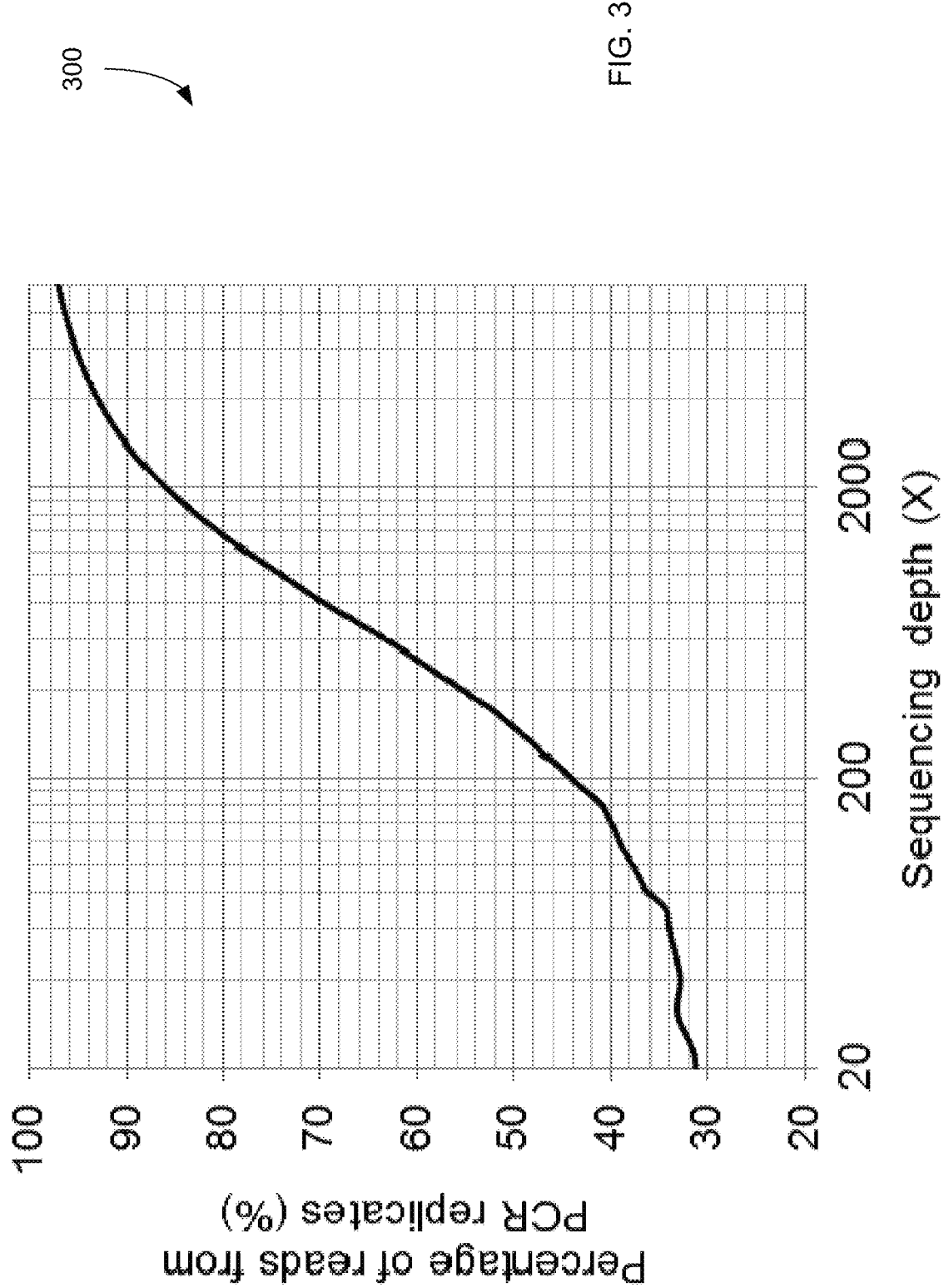
FIG. 3 is a plot 300 showing the relationship between the percentage of sequence reads from PCR replicates and sequencing depth.

FIG. 3 is a plot 300 showing the relationship between the percentage of sequence reads from PCR replicates and sequencing depth. The percentage of sequence reads coming from PCR replicates increases with sequencing depth. At a sequencing depth of 200×, 44% of the sequence reads would be from PCR replicates. Such sequence reads from PCR replicates would not provide additional information.

Figure 4A:
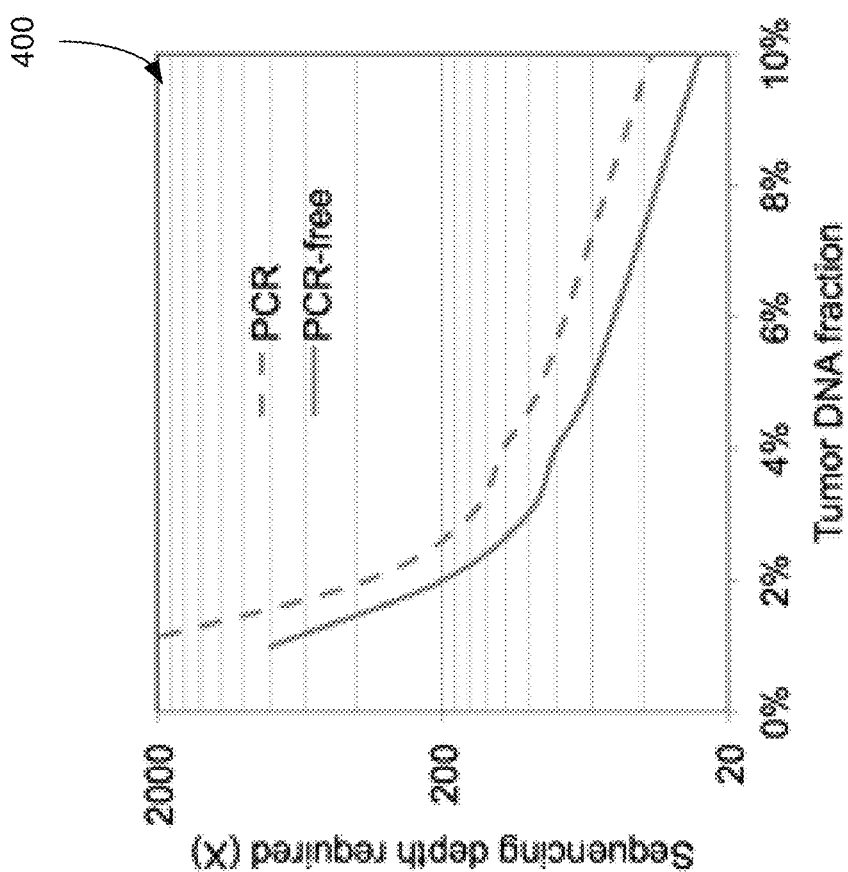

FIGS. 4A and 4B show a comparison between the sequencing depth required for PCR and PCR-free protocols to detect cancer-associated mutations in the plasma of a cancer subject at various tumor DNA fractions according to embodiments of the present invention. Based on the predicted percentage from PCR replicates, we performed a simulation analysis to determine the amount of sequencing required to detect cancer-associated mutations in the plasma of a cancer subject. Simulations were performed to cover tumor DNA fractions in plasma from 1% to 10%. We assumed that 30,000 mutations are present in the genome of a cancer cell in this subject.

The protocol with PCR pre-amplification would require a higher sequencing depth to detect the cancer-associated mutations at any tumor DNA fraction in plasma. The difference in sequencing depth required would increase exponentially with the reduction in tumor DNA fraction. At a tumor DNA fraction in plasma of 10%, protocols with and without PCR pre-amplification require sequencing depths of 37× and 25×, respectively. However, at a tumor DNA fraction in plasma of 2%, the respective sequencing depth required would be 368× and 200×.

Therefore, the use of a PCR-free protocol is highly advantageous for the detection of cancer-associated changes in plasma, in particular when the tumor DNA fraction in plasma is low. If the number of mutations present within the tumor genome of the plasma is lower, higher sequencing depths would be needed. The difference in the depth required for the protocols with or without amplification would be even larger, especially when the tumor DNA fraction in the plasma sample is low.

D. Distinction from Conventional "Deep Sequencing"

There are a number of features that distinguish the use of exhaustive sequencing for achieving ultra-deep and broad sequencing from previous sequencing methods. In one aspect, some of the previous sequencing approaches termed 'deep sequencing' would typically involve the amplification of a target sequence of interest, e.g. by PCR. Then, the amplified DNA, also termed an amplicon, is sequenced multiple times by sequencing. One example of such an approach is tagged-amplicon deep sequencing (Forshew et al. Sci Transl Med 2012; 4: 136ra68). Exhaustive sequencing, on the other hand, is most efficiently implemented without any amplification step, as then all of the detected fragments are original fragments and not replicated data, thereby allowing greater breadth and true depth (as opposed to apparent depth). By apparent depth, we refer to the sequencing of an amplified sequencing library in which a proportion of the sequencing power is consumed in sequencing PCR duplicates, and hence the information yield of the sequencing is not commensurate with its depth.

Since deep sequencing typically use an amplification step, a proportion of the sequencing power is expended on sequencing PCR duplicates. The existence of such PCR duplicates would make it very difficult to exhaustively analyze every template DNA molecule within the sample by deep sequencing of amplified sequencing libraries. A number of groups have described methods for providing information about the duplication rate, e.g. by barcoding the sequencing library (Kinde et al. Proc Natl Acad Sci USA 2011; 108: 9530-9535). For example, in the method described by Kinde et al, one has to perform three steps: (i) assignment of a unique identifier (UID) to each template molecule, (ii) amplification of each uniquely tagged template molecule to create UID families, and (iii) redundant sequencing of the amplification products. In contrast, the use of PCR-free libraries for exhaustive sequencing would avoid the problems caused by PCR duplicates, and the method described by Kinde et al would not be necessary.

In fact, most of the previously practiced deep sequencing approaches cannot achieve the breadth that could be achieved with the use of exhaustive sequencing. For example, amplicon sequencing typically achieves high depth for a narrow genomic region. Even with the use of multiplexing, the total breadth of the genome covered is limited and is far from genomewide. As explained in this application, for the cancer screening test, as close to genomewide coverage is preferred to cover as many putative mutation sites as possible. For example, even if one applies an extreme degree of multiplex amplicon sequencing, e.g. 3 million amplicons, each covering 1,000 bases, the PCR duplicates would become an issue as described earlier.

Similarly, researchers have applied hybridization capture to achieve deep sequencing of selective genomic regions, termed targeted sequencing. However, the capture protocols typically involve amplifications steps. When the size of the targeted region is relatively small, large proportions of PCR duplicates, some 50% even up to 90% (New et al. J Clin Endocrinol Metab 2014; 99: E1022-1030) would be reached when the targeted sequencing is performed in plasma DNA. At such high levels of PCR duplication, the effective depth of the sequencing is reduced. The breadth of the sequencing is limited by the size of the target region.

These observations illustrate that researchers have not been motivated to achieve sequencing that is broad and deep at the same time. However, adopting the principles of exhaustive sequencing described in this application, one may modify targeted sequencing protocols to ensure that the PCR duplication rates are kept to a minimum while needing to capture a large proportion of the human genome. For example, one may use light amplification to prepare the target sequencing library to keep PCR duplicates to a minimum. Then, the breadth of the analysis would need to be achieved by pooling data from multiple target panels. However, when these considerations are taken into account, the targeted approach may not be more cost-effective than the non-targeted exhaustive sequencing approach. Yet, there may be other reasons where target enrichment of a large portion of the genome is preferred. For example, one may justify the need to focus the exhaustive sequencing effort to the repeat or non-repeat regions of the genome if one part shows clustering for the occurrence of de novo or somatic mutations. As an example, one may prefer to focus the efforts on the heterochromatin instead of the euchromatin region of the genome.

E. For Fetal Analysis

Exhaustive sequencing of plasma DNA can be useful for noninvasive prenatal testing. Fetal DNA is present in the plasma of a pregnant woman (Lo et al. Lancet 1997; 350: 485-487) and can be used for the noninvasive prenatal testing of a fetus (e.g. for chromosomal aneuploidies and single gene disorders).

Thus far, the detection of de novo fetal mutations by maternal plasma DNA sequencing is hampered by the sequencing error rate of the current generation of massively parallel sequencers (Kitzman et al. Sci Transl Med 2012; 4: 137ra76 and US Patent Publication US 2015/0105261 A1). Hence, using a previously reported approach, millions of candidate fetal de novo mutations would be identified in maternal plasma but only several tens of these would be true mutations despite the incorporation of bioinformatics steps to filter potential false-positives.

However, using exhaustive sequencing of maternal plasma DNA, one could overcome this problem. Using a PCR-free library preparation process, a candidate fetal de novo mutation that is identified in more than one maternal plasma DNA molecule would have a higher chance of being a true mutation. In other embodiments, one can set a more stringent classification criterion, such as the same mutation being identified more than 2, 3, 4, 5 or more times in the maternal plasma sample.

A number of workers have used single molecule sequencing, e.g. using the Helicos platform, for the noninvasive prenatal testing of maternal plasma for detecting fetal chromosomal aneuploidies (van den Oever et al. Clin Chem 2012; 58: 699-706 and van den Oever et al. Clin Chem 2013; 59: 705-709). However, such work was performed through the sequencing of a small fraction of the molecules in plasma, and thus did not achieve deep and broad sequencing.

F. Further Applications of Exhaustive Sequencing

In another embodiment, one can use exhaustive plasma methylomic sequencing to identify plasma DNA molecules derived from different organs within the body. This is possible because different tissues within the body have different methylation profiles. Through a process of deconvolution, one can identify the relative contributions of different tissues into plasma (Sun et al. Proc Natl Acad Sci USA 2015; 112: E5503-5512).

In another embodiment of exhaustive sequencing of plasma DNA, one can identify mutations in plasma DNA that are associated with multiple physiological or pathological processes. In one embodiment, such processes include those associated with aging. In another embodiment, such processes include those associated with environmental agents, e.g. pollution, radiation, infectious agents, toxic chemicals, etc. In this latter embodiment, different processes might have their own mutational signatures (Alexandrov et al. Nature 2013; 500: 415-421).

Exhaustive sequencing of plasma nucleic acid can also be applied to the sequencing of mRNA and non-coding RNA (e.g. microRNA and long non-coding RNA) in plasma. Previous data have shown that plasma transcriptomic profiling would allow the contributions from various tissues to be deconvoluted from the plasma sample (Koh et al. Proc Natl Acad Sci USA 2014; 111: 7361-7366). Exhaustive transcriptomic sequencing of plasma would further enhance the robustness and usefulness of such an approach.

V. Filtering Criteria for Identifying Mutation

As described above in section III.B, the specificity in identifying mutations and any tests using such mutations (e.g., use of mutational load to determine a level of cancer) can be improved by applying filtering criteria to loci where one or more sequence reads having a mutation have been aligned. As an example for cancer, high specificity can be achieved by scoring a genetic or genomic signature as positive only when there is high confidence that it is cancer associated. This could be achieved by minimizing the number of sequencing and alignment errors that may be misidentified as a mutation, e.g., by comparing to the genomic profile of a group of healthy controls, and/or may be achieved by comparing with the person's own constitutional DNA and/or may be achieved by comparing with the person's genomic profile at an earlier time.

Various criteria could be applied as filtering criteria to assess the likelihood of a DNA fragment carrying a mutation. Each filtering criterion could be used individually, independently, collectively with equal weighting or different weightings, or serially in a specified order, or conditionally depending on the results of the prior filtering steps, as is described above. Examples of filtering criteria are provided below.

A. Dynamic Cutoff

One or more dynamic cutoff filtering criteria can be used to distinguish single nucleotide variants, namely mutations and polymorphisms, from nucleotide changes due to sequencing error. Depending on the context, mutations can be "de novo mutations" (e.g., new mutations in the constitutional genome of a fetus) or "somatic mutations" (e.g., mutations in a tumor). Various parameter values can be determined for each of a plurality of loci, where each parameter value is compared to a respective cutoff value. A locus can be discarded as having a potential mutation if a parameter value does not satisfy a cutoff.

For the identification of somatic mutations in cancer, the high-depth sequencing data from a person's constitutional DNA (e.g., buffy coat) and plasma DNA can be compared to identify sites that are heterozygous in the plasma DNA (AB) and homozygous (AA) in the constitutional DNA. "A" and "B" denote the wildtype and mutant alleles, respectively. Here, we illustrate one embodiment of implementing the dynamic cutoff strategy for mutation detection, where, the binomial and Poisson distribution models were used to calculate three parameters.

Regarding a first parameter, the accuracy of determining the homozygous sites (AA) in the constitutional DNA is affected by sequencing error. The sequencing error can be estimated by a number of methods known to those skills in the art. For example, the sequencing error rate (denoted by "$\varepsilon$") of Illumina HiSeq platforms have been estimated to be 0.003. Assuming the sequenced counts follow a binomial distribution, we calculated the first parameter, Score1, as Score1=1−pbinom(c, D, $\varepsilon$). D represents the sequencing depth, which is equal to the sum of "c" and "a". "c" refers to the number of sequence reads covering the mutant allele B. "a" refers to the number of sequence reads covering the wildtype A allele. "pbinom" is the binomial cumulative distribution function, which can be written as $$\sum_{i=0}^{c}\binom{D}{i}\varepsilon^{i}(1-\varepsilon)^{D-i},$$

where $$\binom{D}{i}$$

represents a mathematical combination function, i.e. the number of combinations selecting i times of the mutant allele from sequencing depth D, which can be further written using factorial as $$\frac{D!}{i!(D-i)!}.$$

The higher the value of Score1, the more confident that the actual genotype is AA. A cut-off greater than 0.01 could be used. This parameter can be used to control the influence of sequencing errors.

Regarding a second parameter, there is a chance that the observed wildtype AA (homozygous) in the constitutional genome would be miscalled from the actual AB (heterozygous) genotype due to insufficient sequencing depth of the SNP loci. To minimize the influence of this type of error, we calculated the second parameter, Score2, as Score2=ppois(b, D/2), where "b" is the number of sequenced counts covering the B allele, and "ppois" is the Poisson cumulative distribution function, which can be written as $$\sum_{i=0}^{b} \frac{\lambda^i e^{-\lambda}}{i!},$$

where λ is the average sequencing depth per strand (i.e. D/2); e is the base of the natural logs (~2.717828). The lower the value of Score2, the more confident that the actual genotype is AA. For example, a cut-off of <0.001, 0.0001, $10^{-10}$, etc. can be used. This parameter can be used to control allele or variant drop out, which refers to heterozygous sites appearing like homozygous sites because one allele or variant could not be amplified, and thus this missing allele or variant has dropped out. Certain data below uses cutoffs of score1>0.01 and score2<0.001, where score1 and score2 can be used to guarantee that the buffy coat is homozygous.

Regarding a third parameter, there is a chance that the observed mutant AB would be miscalled from the actual AA genotype due to sequencing errors. To minimize the influence of this type of error, we calculated the third parameter, Score3, as $$\text{Score3} = \binom{D}{b} \times \varepsilon \times \left(\frac{\varepsilon}{3}\right)^{(b-1)},$$

where $$\binom{D}{b}$$

represents a mathematical combination function, i.e. the number of combinations selecting b times of the mutant allele from sequencing depth D, which can be further written using factorial as $$\frac{D!}{b!(D-b)!};$$

"ε" represents sequencing error rate which was estimated to be 0.003 in this example. The lower the Score3, the more confident that the actual genotype is AB. For example, a cut-off of <0.001, 0.0001, $10^{-10}$, etc., can be used.

Score1 and Score2 can be applied to constitutional tissue, and Score 3 can be applied to mixture (tumor or plasma). Therefore the joint analysis between constitutional tissues and mixture samples by adjusting Score1, Score2, and Score3 can be conducted to determine the potential mutations.

Different thresholds for the calculation of each score can be used in the dynamic cutoff depending on the intended purpose. For example, a lower value for Score3 could be used if one prefers high specificity in the identification of somatic mutations. Similarly, a higher value for Score3 could be used if one prefers to detect a greater total sum of somatic mutations. The specificity of the identified somatic mutations can be improved by using other filtering parameters, e.g., as described below. Other mathematical or statistical models can also be used, for example, Chi square distribution, Gamma distribution, normal distribution, and other types of mixture models. The process could be similarly applied for the identification of fetal de novo mutations.

B. Realignment

One or more realignment filtering criteria can reduce the effects of sequencing and alignment errors in the detection of sequence variants from sequencing data, and therefore also reduce false positives in the identification of mutations. Various embodiments using realignment are now described.

In an initial (first) alignment procedure, the sequencing reads can be aligned (mapped) to a reference genome (e.g., a reference human genome), e.g., by any alignment techniques available to those skilled in the art, e.g., SOAP2 (Li et al. Bioinformatics 2009; 25: 1966-7). After alignment to a locus, a comparison to a genome (e.g., a reference genome, a constitutional genome of the subject or associated with the subject, or genomes of the parents of the subject) can be made to identify whether a sequence variant exists in the reads.

The sequence reads carrying the putative variants can be realigned (mapped again) to the reference human genome through the use of an independent (second) aligner, e.g., Bowtie2 (Langmead et al. Nat Methods 2012; 9: 357-9). The independent aligner would be different from the initial aligner in terms of their use of matching algorithms. Examples of matching algorithms used by the initial aligner and the realigner can include, for example but not limited to, the Smith-Waterman algorithm, Needleman-Wunsch algorithm, Hashing algorithm, and Burrows-Wheeler transformation. The realignment can identify and quantify the quality or certainty of the mutations identified. The independent aligner can differ from the initial aligner in other ways, as well, such as the threshold of reporting a valid alignment, penalties to insertions/deletions and mismatches, the number of mismatches allowed, the number of nucleotides being used as seeds for alignment.

In some embodiments, the following realignment criteria can be used alone or in combination to identify a mapped read as a low-quality sequence read: (1) the sequence read carrying the mutation is not recovered by an independent aligner, which does not align (map) with the sequence read; (2) the sequence read carrying the mutation shows inconsistent mapping results when using an independent aligner to verify the original alignment (e.g., a mapped read is placed to a different chromosome compared to the original alignment result); (3) the sequence read carrying the mutation aligned to the same genomic coordinate exhibits a mapping quality less than a specified threshold using the independent aligner (e.g., mapping quality ≤Q20 (i.e. misalignment probability <1%)—other examples of thresholds can be 0.5%, 2%, and 5% of misalignment probability; (4) the sequence read has the mutation located within 5 bp of either read end (i.e. 5' or 3' ends). This last filtering rule can be important because sequencing errors were more prevalent at both ends of a sequence read. The mapping quality is a metric defined within an aligner and specify a probability that a sequence read is misaligned. Different aligners can use different metrics.

If the proportion of low-quality sequence reads among the sequence reads carrying the mutation is greater than a certain threshold, (e.g., 30%, 35% 40%, 45%, or 50%), the candidate mutant site can be discarded. Thus, if the remaining sequence reads are less than a threshold, then the locus can be discarded from a set of loci identifying as having a mutation in at least some tissue (e.g., tissue of a tumor or tissue of a fetus).

In previous work, including efforts from GATC (www-.gatc-biotech.com) and from the MuTect algorithm (Cibulskis et al. Nat Biotechnol 2013; 31: 213-219), only potential insertion or deletion sites were realigned. Those other schemes do not recalculate the quality score of a sequence read using data from a different aligner. Furthermore, it has not been shown that a recalculated quality score can be used for the purpose of filtering putative variants or mutations. Data is shown below to illustrate the efficacy of using a realignment procedure.

C. Mutation Fraction

Those skilled in the art would recognize that there are methods available to measure the fractional concentration of fetal DNA in maternal plasma or the fractional concentration of tumor DNA in the plasma of a cancer subject. Thus, in one embodiment, to improve the chance of identifying a true informative DNA fragment, only alleles or variants with a fractional count equal to or higher than the fractional concentration measured by another method would be considered as true variants or mutations. The fractional concentration cutoff is termed the mutant fraction threshold (M %), or just fraction threshold. Other implementations can use a threshold lower than the measured fractional concentration, but the selected threshold can depend on the measured value (e.g., within a specified percentage of the measured fractional concentration).

In another embodiment, other values could be adopted as the mutant fraction threshold even without regard to the measured fetal DNA fraction or tumor DNA fraction. Higher M % may be used as a cutoff if higher specificity in mutation identification is preferred. Lower M % may be used as a cutoff if higher sensitivity in mutation identification is preferred. Examples for the fraction threshold include 5%, 10%, 15%, 20%, 25%, and 30%.

In yet another embodiment, the variance in the allelic fraction of putative mutations within contiguous chromosomal regions could provide information regarding the likelihood of DNA fragments from the region as being informative cancer DNA fragments. For example, the contiguous chromosomal regions of interest can be those with copy number aberrations. In regions with copy number gains, there would be an enrichment in tumor-derived DNA. Hence, the allelic fraction of the true somatic mutations would be expected to be higher in such regions with gains, than regions with copy number losses (because of depletion of the tumor-derived DNA at these latter regions).

The range or variance in the allelic ratios of true putative mutations would be larger in the copy number gain regions than the copy number loss regions. Thus, different M % could be set as filtering cutoffs for regions with copy number gains or losses to increase the likelihood of identifying true somatic mutations. Cutoffs specifying the variance in the observed plasma mutant fraction could also be used to identify DNA molecules that have originated from chromosomal regions that are more likely to be enriched with (for regions with copy number gains) or are depleted of (for regions with copy number losses) tumor-derived DNA. A decision could then be made regarding the likelihood of the DNA fragments being informative cancer DNA fragments.

D. Size Filter

While plasma DNA generally circulates as fragments that are <200 bp in length, fetal-derived and tumor-derived plasma DNA molecules are shorter than the background non-fetal and non-tumor DNA molecules, respectively (Chan et al. Clin Chem 2004; 50: 88-92 and Jiang et al. Proc Natl Acad Sci USA 2015; 112: E1317-1325). Therefore, short size can be used as another feature that increases the likelihood that a plasma DNA fragment is fetal or tumor-derived. Thus, in some embodiments, a DNA size filtering criterion could be applied.

Various size criteria can be used. For example, a threshold difference in the median sizes between DNA fragments carrying mutant alleles and wildtype alleles can be required to be at least a certain number of bases, which may be denoted as $\Delta S$. Thus, $\Delta S \geq 10$ bp can be used as a size filter criterion. Examples of other size thresholds include 0 bp, 1 bp, 2 bp, 3 bp, 4 bp, 5 bp, 6 bp, 7 bp, 8 bp, 9 bp, 11 bp, 12 bp, 13 bp, 14 bp, 15 bp, 16 bp, 17 bp, 18 bp, 19 bp and 20 bp. Other statistical tests can be also used, for example, t-test, Mann-Whitney U test, Kolmogorov-Smirnov test etc. A p-value can be determined using these statistical tests and compared to a threshold to determine if the DNA fragments carrying the sequence variant would be significantly shorter than those carrying the wildtype alleles. Examples of the threshold for the p-value can include, but not limited to, 0.05, 0.01, 0.005, 0.001, 0.0005, and 0.0001.

Accordingly, in one embodiment, one can obtain the size information on sequenced plasma DNA molecules. One can do this either using paired-end sequencing, which includes sequencing the entire DNA molecule. For the latter, as plasma DNA molecules are generally below 166 bp, sequencing the entire DNA molecule could be readily performed using many short-read massively parallel sequencing platforms. As plasma DNA derived from cancer cells are generally short while those from the peritumoral or non-tumoral tissues are generally long (Jiang et al. Proc Natl Acad Sci 2015; 112: E1317-1325), having the size information of plasma DNA would further assist the classification of the sequenced fragments as being likely derived from the cancer or non-cancer cells. This information would further assist the screening, detection, prognostication, and monitoring of cancer.

And, as fetal DNA in maternal plasma is shorter than maternal DNA (Chan et al. Clin Chem 2004; 50: 88-92 and Yu et al. Proc Natl Acad Sci USA 2014; 111: 8583-8588), one can also utilize the size information of the plasma DNA when interpreting the results from the exhaustive plasma DNA sequencing. Hence, a shorter fragment in maternal plasma has a higher chance of being fetal-derived.

E. Methylation Status

DNA methylation profile is different between different tissues. Some methylation signatures are relatively tissue-specific. For example, the promoter of SERPINB5 is hypomethylated in the placenta (Chim et al. Proc Natl Acad Sci USA 2005; 102: 14753-14758) and the promoter of RASSFIA is hypermethylated in the placenta (Chiu et al. Am J Pathol 2007; 170: 941-950). The promoters of certain tumor suppressor genes, including RASSFIA, are hypermethylated in cancers. However, the placenta (Lun et al. Clin Chem 2013; 59: 1583-1594) and cancer tissues (Chan et al. Proc Natl Acad Sci 2013; 110: 18761-18768) are shown to be globally hypomethylated, especially in the non-promoter regions.

As fetal DNA in maternal plasma has been shown to have different DNA methylation patterns from maternal-derived DNA, DNA methylation information can help one to predict the probability that a sequenced molecule is maternally or fetally derived. In one embodiment, as the placenta is a major source of fetal DNA in maternal plasma and placental DNA is more hypomethylated than maternal blood cell DNA (Lun et al. Clin Chem 2013; 59: 1583-1594), a hypomethylated DNA fragment sequenced from maternal plasma is more likely to be a fetally-derived one. Similarly, in one embodiment, as tumor DNA is more hypomethylated than blood cell DNA (Chan et al. Proc Natl Acad Sci 2013; 110: 18761-18768), a hypomethylated DNA fragment containing a putative (candidate) mutation sequenced from the plasma of an individual tested for cancer is more likely to be a cancer-associated or cancer-specific one than one that does not have hypomethylation.

The methylation status can be used in various ways for determining whether a locus exhibits a mutation. For example, a threshold amount of methylation density may be required of DNA fragments aligning to the locus with the mutation before the locus is considered a mutation. As another example, a binary scoring of a CpG site can be used, e.g., where there is only one CpG site per DNA fragment. A CpG site can be discarded if the one DNA fragment does not have the expected methylation status. Whether to discard a DNA fragment can be dependent on other filtering criteria. For example, if the DNA fragment is sufficiently short, then the DNA fragment can be kept. This is an example of using various filtering criteria in combination with different weights or in combination as part of a decision tree.

Methylation analysis of plasma DNA could be achieved by methylation-aware approaches, including bisulfite conversion, methylation-sensitive restriction enzyme digestion or methyl-binding protein treatment. All of these methylation-aware processes could be followed by massively parallel sequencing, single molecule sequencing, microarray, digital PCR or PCR analysis. In addition, some single molecule sequencing protocols could directly read the methylations status of a DNA molecule without prior treatment by other methylation-aware processes (Ahmed et al. J Phys Chem Lett 2014; 5: 2601-2607).

Besides cytosine methylation, there are other forms of DNA methylation, such as but not limited to hydroxymethycytosine (Udali et al. Hepatology 2015; 62: 496-504). Brain tissues (Sherwani and Khan. Gene 2015; 570: 17-24) and melanoma (Lee et al. Lab Invest 2014; 94: 822-838) show higher proportion of hydroxymethylcytosines.

F. Plasma DNA End Location

Filtering of potential cancer-specific or cancer-associated or fetal mutations based on the coordinate of the terminal nucleotide or end location can also be performed. We have identified terminal locations of DNA fragments that are not random and that vary based on a tissue of origin. Thus, the terminal location can be used to determine a likelihood that a sequence read with a putative mutation is actually from fetal tissue or tumor tissue.

Recently, it has been shown that the fragmentation pattern of plasma DNA is non-random (Snyder et al. Cell 2016; 164: 57-68 and PCT WO 2016/015058 A2). The plasma DNA fragmentation pattern is influenced by nucleosomal positioning, transcription factor binding sites, DNase cutting or hypersensitive sites, expression profiles (Snyder et al. Cell 2016; 164: 57-68 and PCT WO 2016/015058; Ivanov et al. BMC Genomics 2015; 16 Suppl 13:S1) and DNA methylation profiles (Lun et al. Clin Chem 2013; 59: 1583-1594) in the genome of the cells that have contributed the plasma DNA molecules. Thus, the fragmentation patterns are different for cells of different tissue origins. While there are genomic regions that show more frequent fragments, the actual plasma DNA cutting sites within the region could still be random.

We hypothesized that different tissues are associated with the release of plasma DNA fragments that have different cutting sites, or end locations. In other words, even the specific cutting sites are non-random. Indeed, we show that plasma DNA molecules in cancer patients show different end locations than patients without cancer. Some embodiments can use plasma DNA molecules with such cancer-associated end locations as informative cancer DNA fragments, or use such end location information as a filtering criterion, e.g., along with one or more other filtering criteria. Thus, with the identification of such cancer-associated plasma DNA end locations, one could score the plasma DNA fragment as an informative cancer DNA fragment or attribute a differential weighting based on the nature of the end location of such a fragment. Such criteria can be used to assess the likelihood of the fragments originating from cancer, certain organs, or cancer of certain organs.

Accordingly, the chance that a plasma DNA fragment is an informative cancer DNA fragment would be much higher if it shows a putative mutation as well as end locations that are cancer-associated. Various embodiments can also take into consideration the status of such a fragment and its length, or any combination of such and other parameters. As a plasma DNA fragment has two ends, one can further modify the weighting for identifying it as a cancer-derived fragment by considering if one or both of its ends are associated with cancer or from a tissue type associated with cancer. The use of a library preparation process that increases the likelihood of a single stranded DNA fragment being converted into the sequencing library would enhance the efficiency of this latter embodiment (for an example of such a library preparation process, see Snyder et al. Cell 2016; 164: 57-68), as is discussed in the next section. In one embodiment, a similar approach based on end locations can also be used for detection mutations associated with other pathologies or biological processes (e.g. mutations due to the ageing process or mutations due to environmental mutagenic factors).

A similar approach can also be used for identifying de novo mutation of a fetus by sequencing the DNA in the plasma of a pregnant woman carrying the fetus. Hence, following the identification of end locations that are specific or relatively specific for the placenta, one can attribute a higher weighting to a putative fetal de novo mutation being a true one if such a DNA fragment in maternal plasma also carries a placental-specific or placental-enriched end location. As a plasma DNA fragment has two ends, one can further modify the weighting for identifying it as a fetal-derived fragment by considering if one or both of its ends are associated with the placenta.

To illustrate the feasibility of this approach, the sequencing data of the plasma DNA for an HCC patient and a pregnant woman were analyzed. For illustration purposes, the analysis was focused on chromosome 8. The same approach can be applied to the whole genome or any other chromosomes or any genomic region or combinations thereof.

The coordinates of the terminal nucleotides at both ends of each sequenced plasma DNA fragment were determined. Then, the number of fragments ending on each nucleotide on chromosome 8 was counted. The top 1 million nucleotides that had the highest number of DNA fragments ending on them were determined for each of the plasma samples from the HCC case and the pregnant woman.

Figure 5:
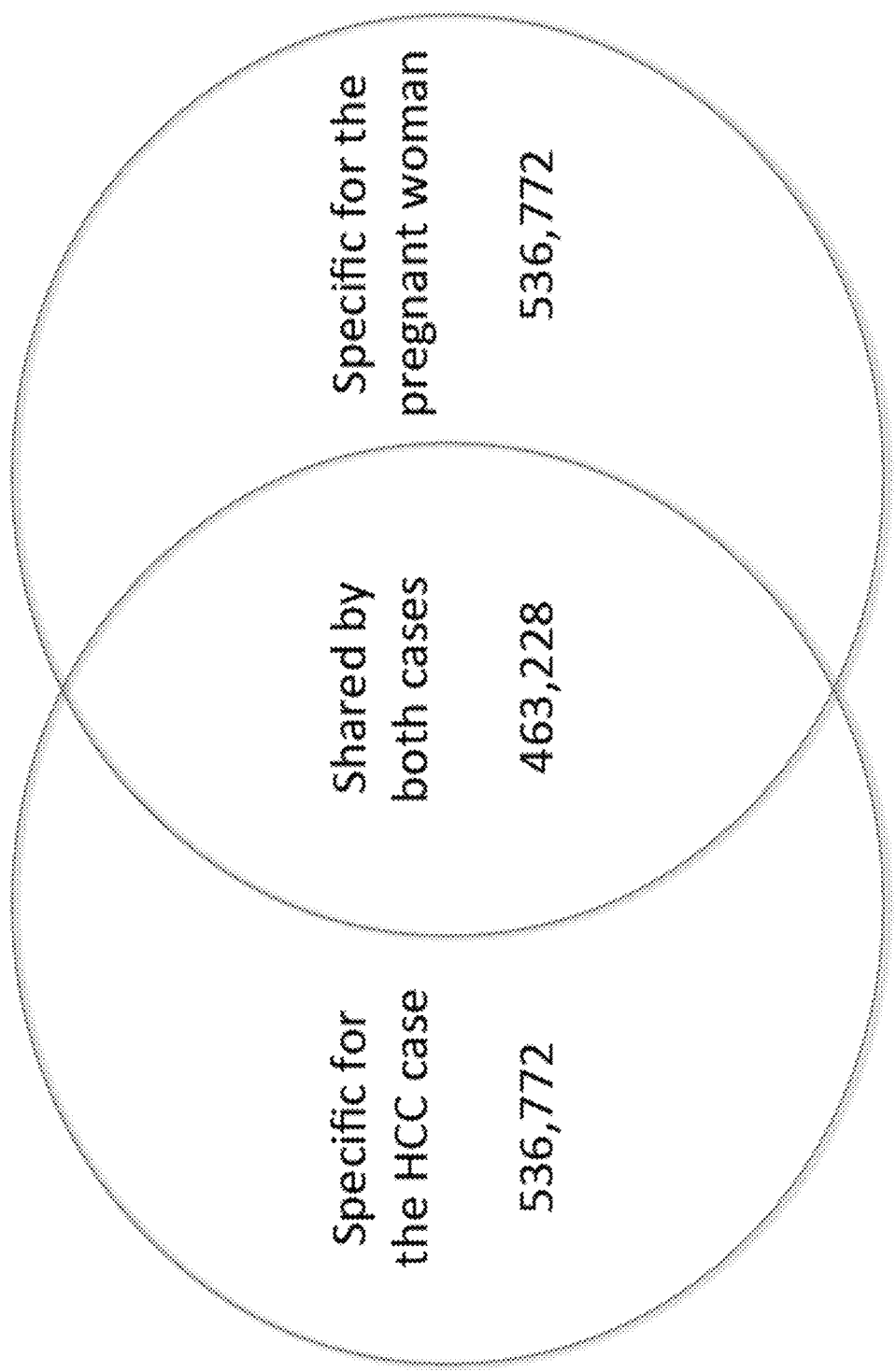
FIG. 5 is a Venn diagram showing the number of frequent end locations that are specific for the HCC case, specific for the pregnant woman, or shared by both cases according to embodiments of the present invention.

FIG. 5 is a Venn diagram showing the number of frequent end locations that are specific for the HCC case, specific for the pregnant woman, or shared by both cases according to embodiments of the present invention. The coordinates of the 463,228 nucleotides that were the frequent ending positions shared by the two cases were then identified. For the HCC case, the shared 463,228 nucleotides were subtracted from the top one million to obtain the coordinates of the 536,772 nucleotides that were the frequent ending positions specific for the HCC case were identified. Similarly, the shared 463,228 nucleotides were subtracted from the 1 million most common ending positions for the pregnancy case to obtain the coordinates of the 536,772 nucleotides that were the frequent ending positions specific for the pregnant woman were also identified.

Plasma DNA fragments with terminal nucleotides ending exactly at the 536,772 HCC-specific ending positions would be more likely to be derived from the tumor. In contrast, plasma DNA fragments with terminal nucleotide ending exactly at the pregnancy-specific ending positions or the positions shared by the two cases would be less likely to be derived from the tumor, with pregnancy-specific ending positions potentially being less likely and given a lower weighting in any embodiment using weights.

Therefore, the list of top ending positions that are specific for the HCC case can be used to select the cancer-associated mutations, and the list of top ending positions that are specific for the pregnant case or shared by both cases can be used to filter out false-positive mutations. A similar procedure can be used for identifying fetal mutations and filtering out false-positive mutations for noninvasive prenatal testing.

In general, to identify such biologically-relevant plasma DNA end locations, plasma DNA samples from groups of individuals with different diseases or epidemiological backgrounds or physiological profiles could be compared with samples from another group of individuals without such diseases or backgrounds or profiles. In one embodiment, each of these samples could be sequenced deeply so that the common end positions of plasma DNA fragments could be identified within each sample. In another embodiment, the sequence data from the group of persons with complimentary profile could be pooled together for the identification of common end locations representative of the disease or physiological profile.

A goal of this analysis is to identify plasma DNA end locations that are common to individuals with the disease or biologically relevant profile, but not in individuals without the disease or biologically relevant profile. For example, the comparisons could involve individuals with and without cancer, individuals with and without cancer of particular organs or tissues, pregnant and non-pregnant individuals, pregnant individuals with and without certain pregnancy-associated or fetal disease, and individuals of different ages. The tissue-specific or disease-relevant plasma DNA end locations after having been identified in a group of reference samples become the reference set for interpretation of test samples.

Each plasma DNA fragment in a sample could be interrogated individually and a likelihood score be assigned based on the end location. The likelihood score for a certain end location can be dependent on the separation in an amount of sequence reads (e.g., a percentage of sequence reads or other value normalized by sequencing depth across the samples) ending at the end location for the target individuals (e.g., cancer) relative to the amount of sequence reads ending for the control group. A larger separation would lead to a higher specificity, and thus a higher likelihood score can be applied. Therefore, classification of plasma DNA fragments with specific end locations into likely disease-associated or not, fetal or maternal, etc., could be performed.

Alternatively, plasma DNA fragments originating from the same region could be interpreted collectively, namely the frequency of ending at a particular nucleotide can be calculated by normalizing to the sequencing depth. In this manner, certain nucleotides can be identified as being common end locations relative to other locations in the genome, e.g., just based on the analysis of one sample of a particular type, although more samples can be used. Therefore, classification of plasma DNA fragments with specific end locations into likely disease-associated or not, fetal, or maternal, etc., could be performed. For loci that show high frequencies of plasma DNA fragments with such biologically-relevant plasma DNA end locations, a determination could be made that such loci are enriched with the biologically-relevant DNA and this be included as a group of plasma DNA fragments being of high likelihood as cancer-associated or fetus-specific or associated with other diseases or biological processes. The level of likelihood can be based on how high the frequency is for a given nucleotide relative to other nucleotides, in a similar manner as comparisons across different groups, as described above.

To illustrate the efficacy of this approach, potential cancer-associated mutations were identified directly from the plasma DNA sequencing data of the HCC patient. Single nucleotide changes that were present in the sequence reads of at least two plasma DNA fragments were considered as potential cancer-associated mutations. The tumor tissue was also sequenced and the mutations that were present in the tumor tissue were considered as true cancer-associated mutations.

On chromosome 8, a total of 20,065 potential mutations were identified from the plasma DNA sequencing data of the HCC patient without using the dynamic cutoff analysis. A sequence variant would be regarded as a potential mutation if the sequence variant was present in at least two sequenced DNA fragments. 884 true somatic mutations were identified from the sequencing result of the tumor tissue. The 20,065 putative mutations included 802 (91%) of the 884 real mutations. Thus, only 4% of the putative mutations were true somatic mutations in the tumor tissue giving a PPV of 4%.

To enhance the accuracy of detecting the somatic mutations, we used the following filtering algorithms based on the terminal nucleotide positions of the sequence reads carrying the putative mutations. (1). For any putative mutation, if there is at least one sequence read carrying the mutation and ending on HCC-specific ending positions, the mutation would be qualified for downstream mutational analysis. (2). A sequence read that carried a putative mutation but ended on any pregnancy-specific ending positions or the positions shared by both cases would be removed. A mutation would be qualified for downstream mutational analysis only if there were two or more sequence reads showing the same mutation after the removal of the reads based on this algorithm.

Applying both 1 and 2 filtering algorithms stated above, the results in table 1 were obtained. The effects of applying different filtering algorithms based on the position of the terminal nucleotides, or end locations, of the DNA fragments carrying the putative mutations.

TABLE 1

|  | No filter | Inclusion of mutations with HCC-specific ends (filter 1) | Removal of reads with shared or pregnancy-specific ends (filter 2) | Applying both filtering algorithms |
|---|---|---|---|---|
| No. of putative mutations identified | 20,065 | 1,526 | 2,823 | 484 |
| Percentage of true mutations detected | 91% | 29% | 88% | 40% |
| PPV | 4% | 17% | 28% | 71% |

There was a substantial improvement in the PPV by adopting any one of the three algorithms requiring the end locations being HCC-specific or the algorithm filtering out the pregnancy-specific or the shared positions. By applying both algorithms, the PPV increased to 71%.

Other number of HCC- and pregnancy-associated end locations can be identified for each chromosome, or indeed for another genomic region, or indeed for the entire genome, for example, but not limited to, 0.5 million, 2 million, 3 million, 4 million, 5 million, 6 million, 7 million, 8 million, 9 million or 10 million. In various embodiments, the most frequently seen end locations in plasma DNA molecules can be determined in one or more cohorts of cancer patients, each cohort being of one cancer type. In addition, the most frequently end locations in plasma DNA molecules can be determined for subjects without cancer. In one embodiment, such patients with cancer and subjects without cancer can be further subdivided into groups with different clinical parameters, e.g. sex, smoking status, previous health (e.g. hepatitis status, diabetes, weight), etc.

As part of using such filtering criteria, statistical analysis can be used to identify the positions that have higher probability of being terminal nucleotides or end locations for circulating DNA for different physiological and pathological conditions. Examples of the statistical analyses include but not limited to the Student t-test, Chi-square test, and tests based on binomial distribution or Poisson distribution. For these statistical analyses, different p-value cutoffs can be used, for example but not limited to 0.05, 0.01, 0.005, 0.001, and 0.0001. The p-value cutoffs can also be adjusted for multiple comparisons.

G. Single-Stranded Sequencing

In one embodiment, sequencing can be performed on the two complementary strands of each template molecule termed single strand sequencing (Snyder et al. Cell 2016; 164: 57-68). Variations that are present in the sequencing reads of both strands are used for downstream analysis, whereas variations that only appear in the sequencing read for one strand are discarded, or at least the data for the one DNA fragment can be discarded. This can further exponentially reduce sequencing errors for the plasma DNA molecules.

Because each strand of the plasma DNA fragments could be analyzed independently, the end locations or terminal nucleotide coordinates of plasma DNA fragments could be determined with higher precision and accuracy. Single strand sequencing also allows the detection of plasma DNA fragments that circulate in a single-stranded form as opposed to a double-stranded form. By including the single-stranded plasma DNA molecules in the analysis (e.g. through the use of a library preparation protocol that would facilitate single-stranded DNA analysis (Snyder et al. Cell 2016; 164: 57-68)), an additional population of potentially informative cancer DNA fragments become amenable to detection.

Furthermore, the use of library preparation protocols that favor single-stranded DNA (for example, see Snyder et al. Cell 2016; 164: 57-68), would also allow one to identify additional locations that can be used for the end location-based filtering criterion. For example, if after alignments of the two sequence reads for the two strands, the two strands do not align to the same tissue-specific end location, then the sequence read can be given a lower weight as having a mutation.

VI. Somatic Mutation Detection in Plasma of Cancer Patients

Various examples for the detection of somatic mutations in subjects being tested for cancer are now described. Data is shown for various filtering criteria. And, the efficiency of PCR-free is illustrated.

A. Specimen Preparation

Clinical specimens were obtained from an HCC patient. A blood sample was collected before operation. A HCC tumor biopsy and a biopsy of the adjacent normal liver tissue were collected at the time of tumor resection. DNA libraries were prepared from the specimens using PCR-free library preparation protocols and sequenced using the Illumina HiSeq series of massively parallel sequencers. The sequencing depths achieved for the buffy coat, tumor biopsy, biopsy of the adjacent normal liver tissue and plasma were 45×, 45×, 40×, and 220× of the human haploid genome, respectively.

1. Patient Information

The HCC patient was a 58-year-old Chinese male, who was a HBV carrier without cirrhosis. The tumor size was 18 cm. He was admitted to the Department of Surgery, Prince of Wales Hospital for tumor resection, and was recruited with informed consent. The study was approved by the Joint Chinese University of Hong Kong and New Territories East Cluster Clinical Research Ethics Committee. 9 mL of peripheral blood was collected in EDTA tubes prior to surgery. Tumor tissue and the adjacent normal tissue were collected after tumor resection.

2. Sample Processing

All blood samples were processed by a double centrifugation protocol (Chiu et al Clin Chem 2001; 37: 1607-1613). Briefly, after centrifugation at 1,600 g for 10 min at 4° C., the plasma portion was recentrifuged at 16,000 g for 10 min at 4° C. to remove the blood cells. The blood cell portion was recentrifuged at 2,500 g, and any residual plasma was removed. DNA from the blood cells and that from plasma was extracted with the blood and body fluid protocol of the QIAamp DNA Blood Mini Kit and the QIAamp DSP DNA Blood Mini Kit, respectively (Qiagen). DNA from the tumor and adjacent normal tissues were extracted with the QIAamp DNA Mini Kit (Qiagen) according to the manufacturer's tissue protocol.

3. Quantification of Plasma DNA

DNA was extracted from 3.7 mL of plasma and was eluted in 110 microliters of water. The DNA concentration was 0.629 nanograms per microliter (Qubit fluorometer, Thermo Fisher Scientific), yielding 69 ng DNA. We then used 30 ng DNA for library construction. Since each 3 Mb genome is broken into 166 base pair (bp) fragments, there should be about $1.81 \times 10^7$ plasma DNA fragments per genome. The 30 ng DNA should contain $[(30 \times 1,000)/3.3] \times 1.81 \times 10^7$ fragments=$1.64 \times 10^{11}$ total fragments.

4. DNA Library Construction

DNA libraries for the genomic DNA samples and the maternal plasma sample were constructed with the TruSeq DNA PCR-free Library Preparation kit (Illumina) according to the manufacturer's protocol except that one-fifth of the indexed adapter was used for plasma DNA library construction. There were three genomic DNA samples, namely the patient's buffy coat DNA, the tumor tissue DNA, and the adjacent normal tissue DNA. For each genomic DNA sample, one microgram DNA was sonicated to 200 bp fragments (Covaris) for library construction. The library concentrations ranged from 17 to 51 nM in 20 μL library.

For the 30 ng plasma DNA sample ($1.64 \times 10^{11}$ fragments), the library yield was 2,242 pM in 20 μL library, which equaled 44,854 attomoles, i.e., $2.70 \times 10^{10}$ 166-bp plasma DNA fragments. The conversion from DNA to library was 16.4%. This level of conversion is much higher than our previous experience of other DNA library preparation kits in which only some 1% of the input DNA could be converted to library.

5. Sequencing of DNA Libraries

All DNA libraries were sequenced on the HiSeq 1500, HiSeq 2000 or HiSeq 2500 sequencing platforms (Illumina) for 75 bp×2 (paired-end). We sequenced multiple lanes for each genomic DNA library. The sequencing depths of the buffy coat, tumor tissue and adjacent normal tissue DNA libraries were 45×, 45× and 40×, respectively. We sequenced 30.7 lanes for the plasma DNA library and obtained approximately 4.4 billion non-duplicated mapped paired-end reads. The sequencing depth was 220×.

To calculate the recovery of plasma DNA library after sequencing, we sequenced 120 μl DNA library at 10 pM per lane as input. The total number of fragments input were $120 \times 10 \times 30.7 \times 6.02 \times 10^{23}/10^{18} = 2.22 \times 10^{10}$ fragments. After sequencing, we obtained $4.40 \times 10^9$ fragments. The recovery of DNA library after sequencing was 19.9%.

The plasma DNA sequences were aligned or mapped to the reference human genome. The number of reads mapped to each 1-Mb segment (bin) as a proportion of all sequence reads were determined across the genome. The proportions or genomic representations per 1-Mb segments were compared with plasma DNA sequencing data obtained from a group of healthy control to identify genomic regions with statistically significant increase or statistically significant decrease in genomic representations as previously described in U.S. Patent Publication 2009/0029377.

Figure 6:
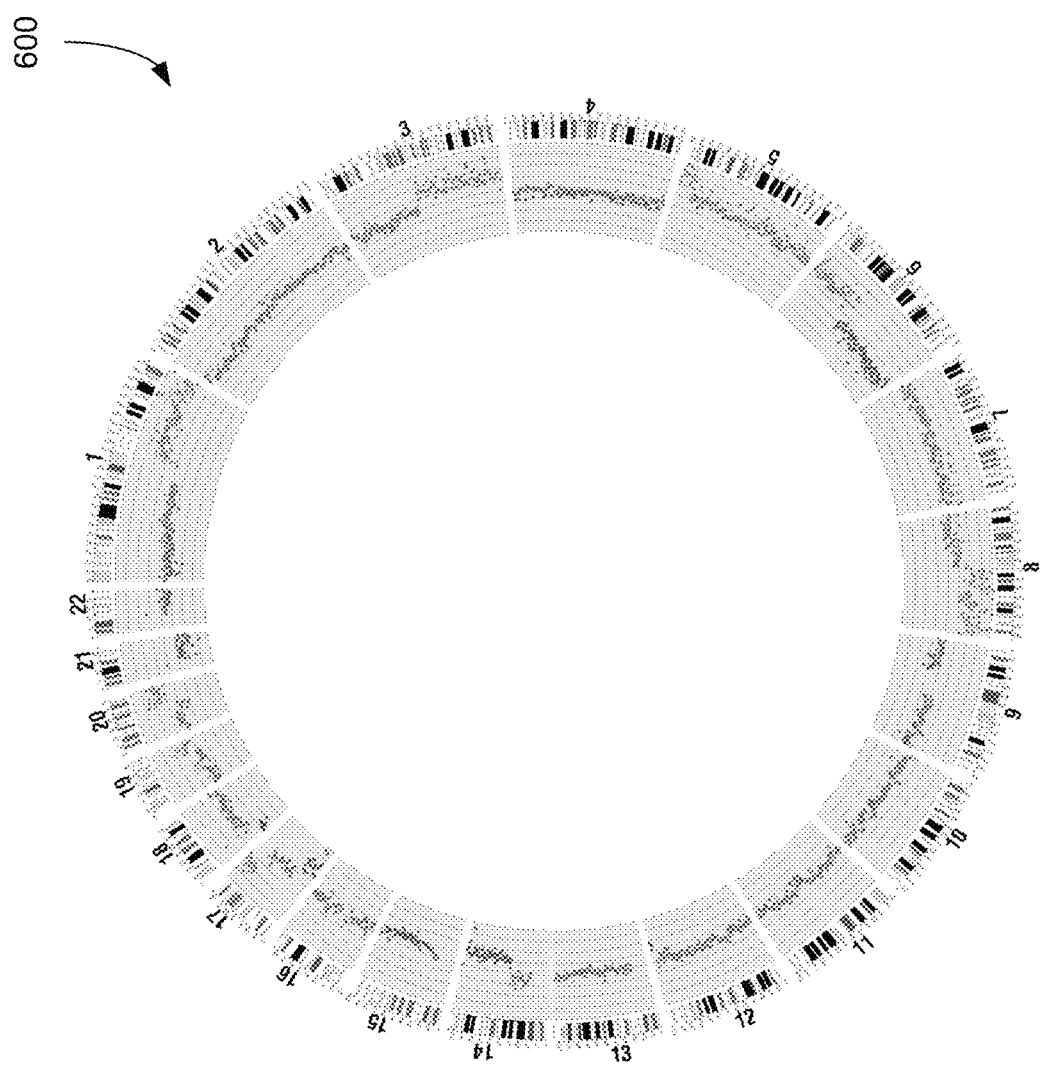
FIG. 6 is a plot 600 showing increases, decreases, or no changes in 1-Mb segments for the HCC patient.

FIG. 6 is a plot 600 showing increases, decreases, or no changes in 1-Mb segments for the HCC patient. Regions with statistically significant increase in genomic representation indicate the presence of copy number gain while regions with statistically significant decrease in genomic representation indicate the presence of copy number loss. Bins with statistically significant increase, decrease, or no significant change in genomic representations are shown as green, red and grey dots, respectively. By quantifying the extent of copy number loss across consecutive genomic segments that showed such losses (e.g., as described in U.S. patent application Ser. No. 14/994,023), the factional concentration of tumor-derived DNA in plasma was determined to be 15%.

B. Mutations Present in Tumor Biopsy and Adjacent Tissue

Next, we identified somatic mutations present in the tumor biopsy by comparing with the buffy coat sequencing data of the patient. This analysis was performed to determine how many somatic mutations that this particular tumor carried and served as the gold standard set of mutations that we aimed to detect in plasma DNA. For any allele detected in the tumor biopsy but not in the buffy coat DNA, we applied a series of filtering criteria to identify the somatic mutations. The initial analysis was performed in half of the sequence data, namely 110×.

Figure 7:
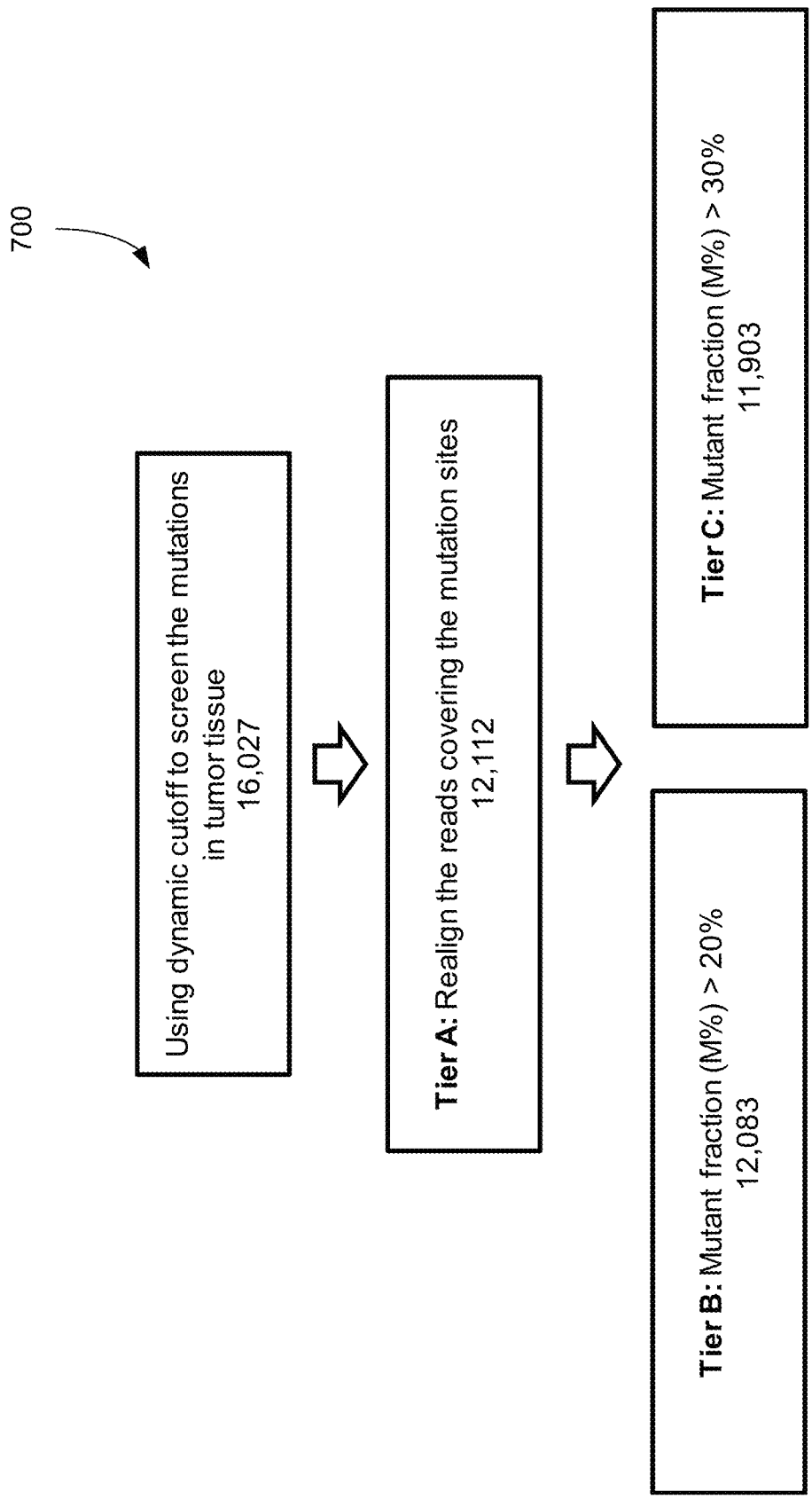
FIG. 7 shows a filtering process 700, which uses dynamic cutoff, realignment, and mutation fraction, and the resulting data for mutations identified from a tumor biopsy according to embodiments of the present invention.

FIG. 7 shows a filtering process 700, which uses dynamic cutoff, realignment, and mutation fraction, and the resulting data for mutations identified from a tumor biopsy according to embodiments of the present invention. As shown in FIG. 7, we first applied the dynamic cutoff strategy to minimize the detection of the false-positive single nucleotide variants, which are mostly a result of sequencing errors. The numbers shown in each box represent the number of putative mutations identified at each step.

The realignment strategy was then applied as a Tier A filtering criterion to the 16,027 putative mutations identified using the dynamic cutoff strategy to further remove variants due to sequencing errors and alignment errors. Next, two different fractional concentration cutoffs were applied independently. Using at least 20% tumor DNA fraction (M %) as a cutoff (Tier B criterion), 12,083 somatic mutations were identified. Using at least 30% tumor DNA fraction as a cutoff (Tier C criterion), 11,903 somatic mutations were identified. We deemed these 11,903 variants as the true somatic mutations present in this tumor. The number is compatible with the reported average number of mutations present per tumor.

Tumor-derived plasma DNA molecules are expected to be shorter than the non-tumor derived molecules. As a means to assess if these variants are true tumor-derived somatic mutations, we searched for plasma DNA fragments that covered these 11,903 loci and assessed the size profile of these fragments.

Figure 8:
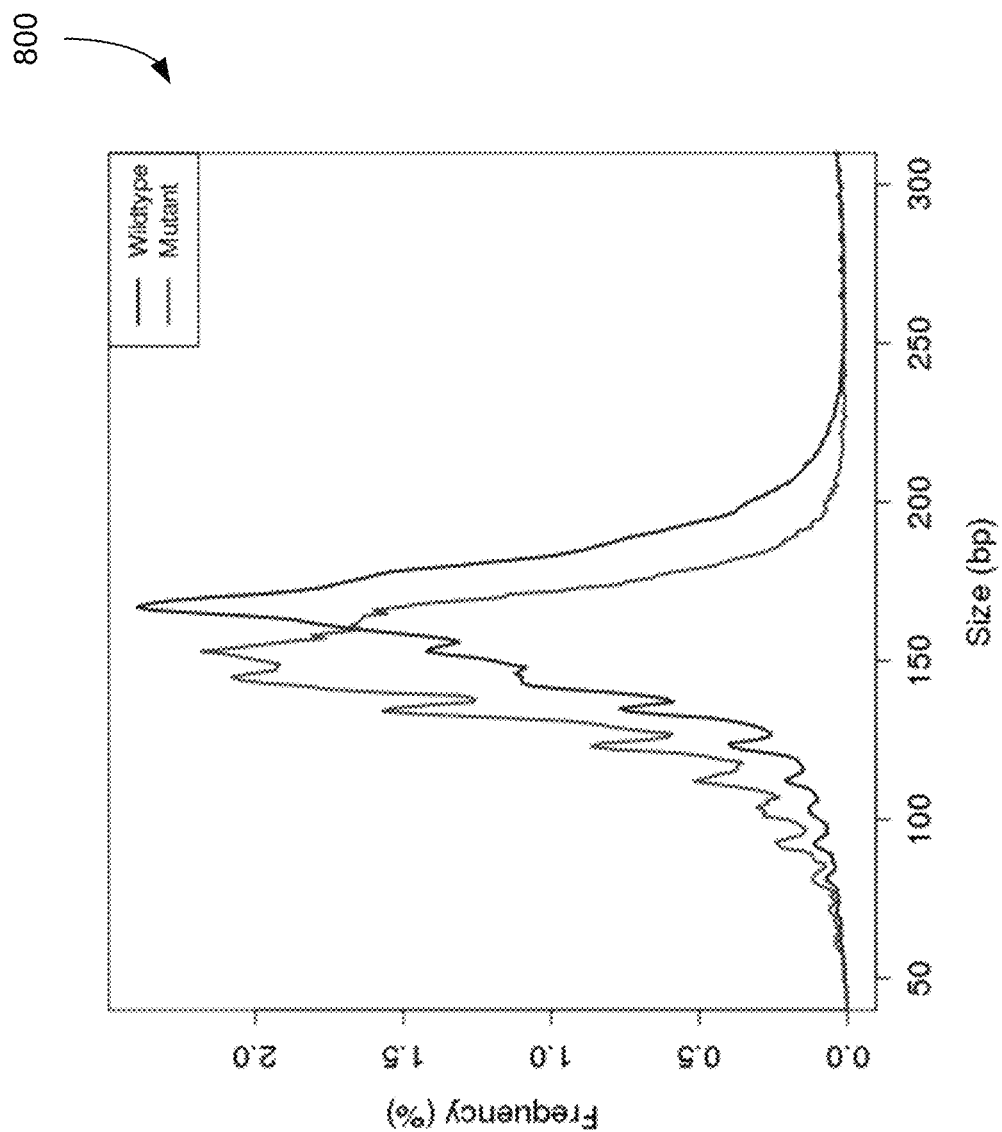
FIG. 8 shows a plot 800 of sizes of plasma DNA fragments identified as having a mutant allele for the HCC patient compared to the sizes of plasma DNA fragments identified as having the wildtype allele.

FIG. 8 shows a plot 800 of sizes of plasma DNA fragments identified as having a mutant allele for the HCC patient compared to the sizes of plasma DNA fragments identified as having the wildtype allele. These plasma DNA fragments identified as having a mutation are indeed shorter than those other plasma DNA fragments that were non-informative for these somatic mutations. Such a size analysis confirms an efficacy of the identification of the mutations, and also confirms the ability to use size as a filtering criterion.

Figure 9:
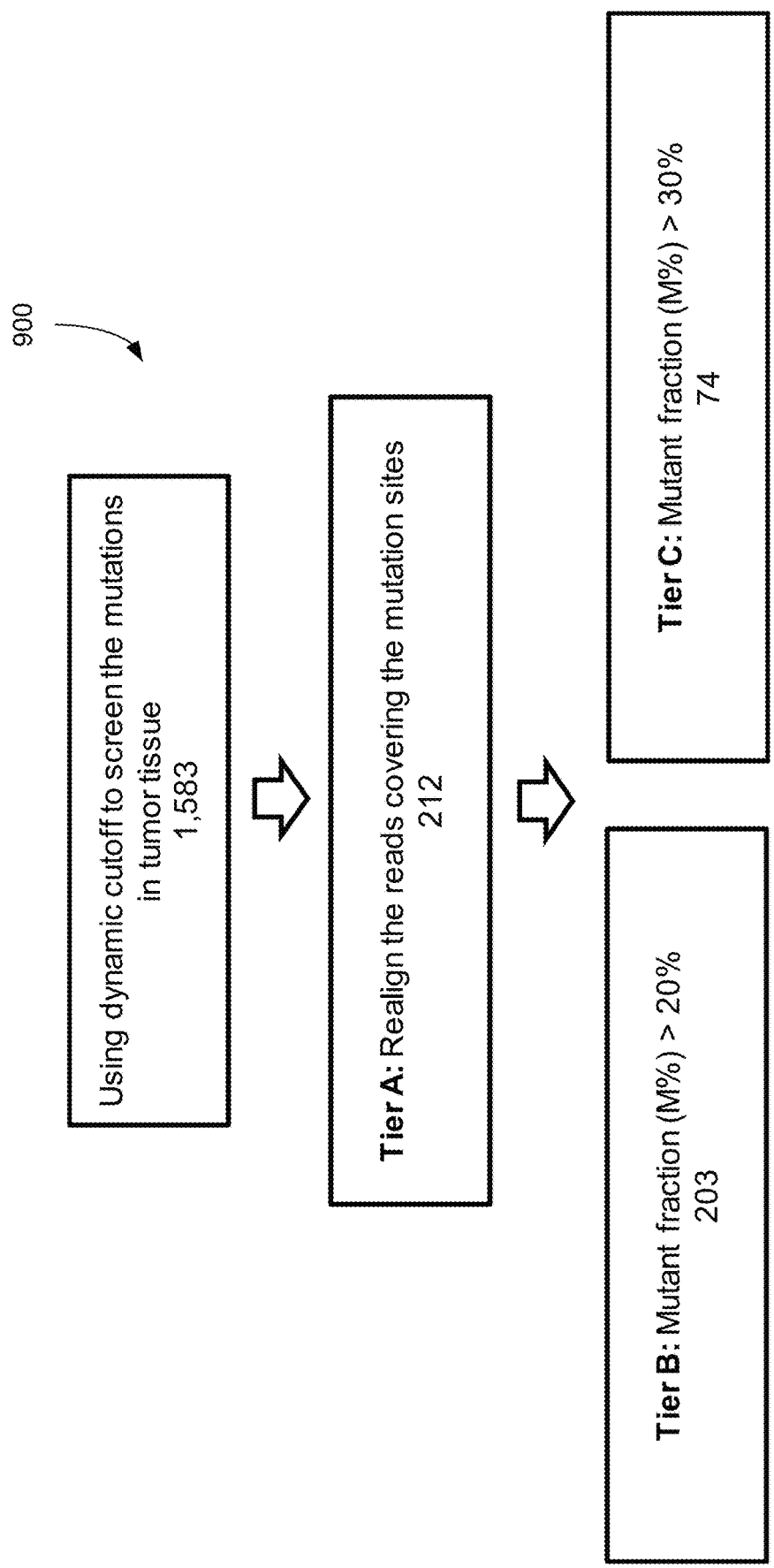
FIG. 9 shows a filtering process 900, which uses dynamic cutoff, realignment, and mutation fraction, and the resulting data for mutations identified from an adjacent normal liver biopsy according to embodiments of the present invention.

FIG. 9 shows a filtering process 900, which uses dynamic cutoff, realignment, and mutation fraction, and the resulting data for mutations identified from an adjacent normal liver biopsy according to embodiments of the present invention. The same set of criteria were applied to screen for mutations in the biopsy of the adjacent normal liver biopsy, as used for the tumor biopsy. As shown in FIG. 9, only 203 mutations were identified when the final filter was based on requiring at least 20% tumor DNA fraction (Tier B criterion). Only 74 mutations were identified when the final filter was based on requiring at least 30% tumor DNA fraction (Tier C criterion).

Figure 10A:
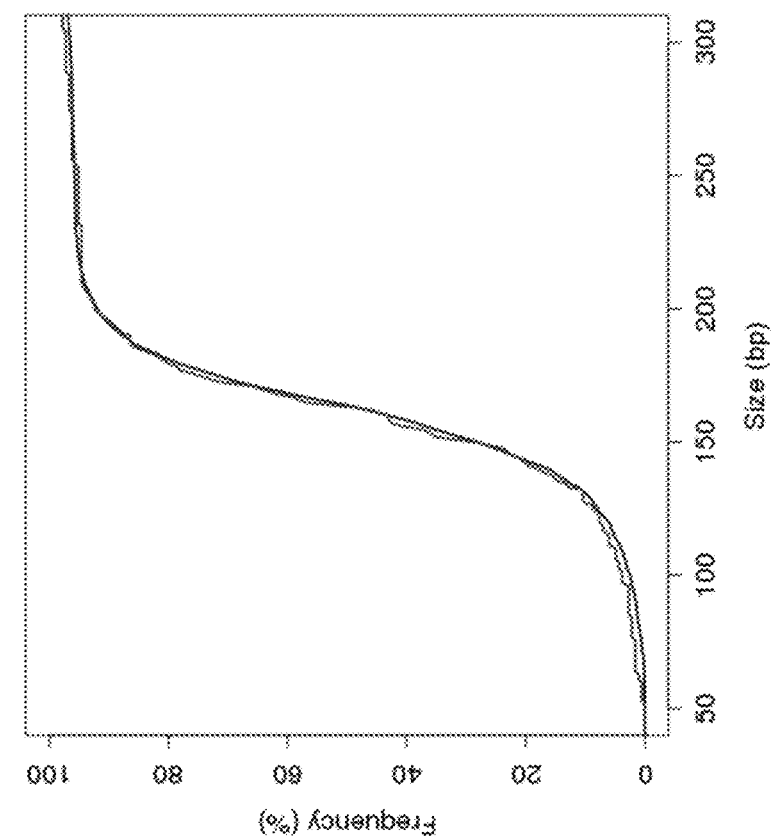
FIGS. 10A and 10B show a comparison of the assessed size profile of plasma DNA fragments carrying the 203 putative mutations identified from the adjacent normal liver biopsy with the size provide of other non-informative plasma DNA molecules.
Figure 10B:
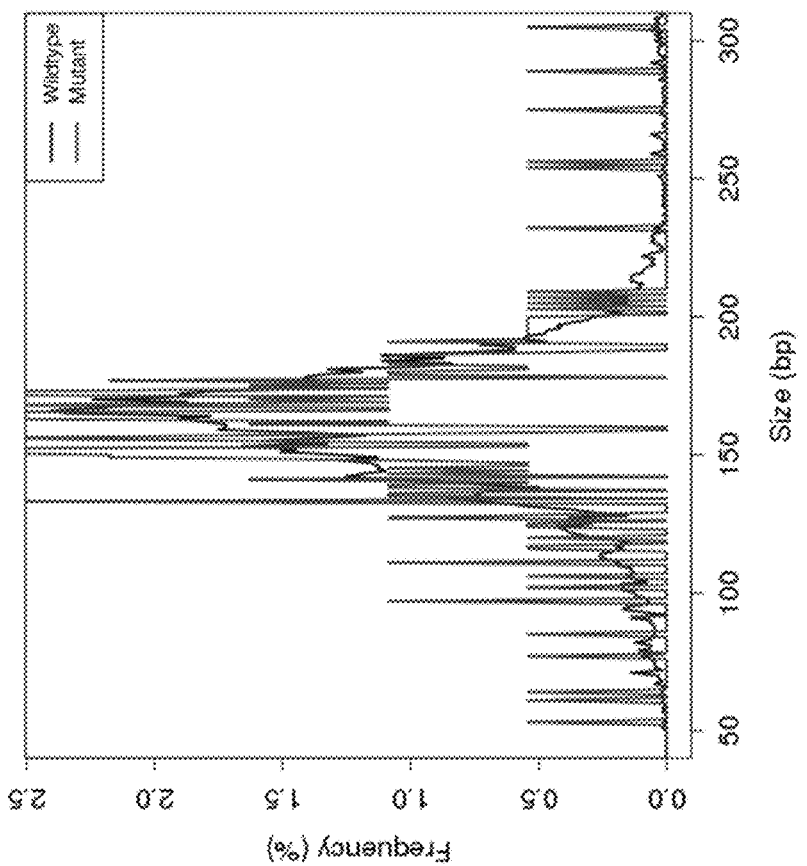

FIGS. 10A and 10B show a comparison of the assessed size profile of plasma DNA fragments carrying the 203 putative mutations identified from the adjacent normal liver biopsy with the size profile of other non-informative plasma DNA molecules. FIG. 10A shows a frequency of plasma DNA fragments over a range of size for the putative mutant allele and the wildtype allele. FIG. 10B shows a cumulative frequency of the plasma DNA fragments as a function of size for the putative mutant allele and the wildtype allele. As shown in FIGS. 10A and 10B, there is no difference in the size profiles of the two groups of DNA expressed in the form of a size frequency distribution curve as well as the cumulative size difference plots. The size profile of these molecules suggests that the variants are likely to be false positives.

C. Mutational Analysis of Plasma

Next, we aimed to apply various filtering criteria to identify somatic mutations or informative cancer DNA fragments in plasma.

Figure 11:
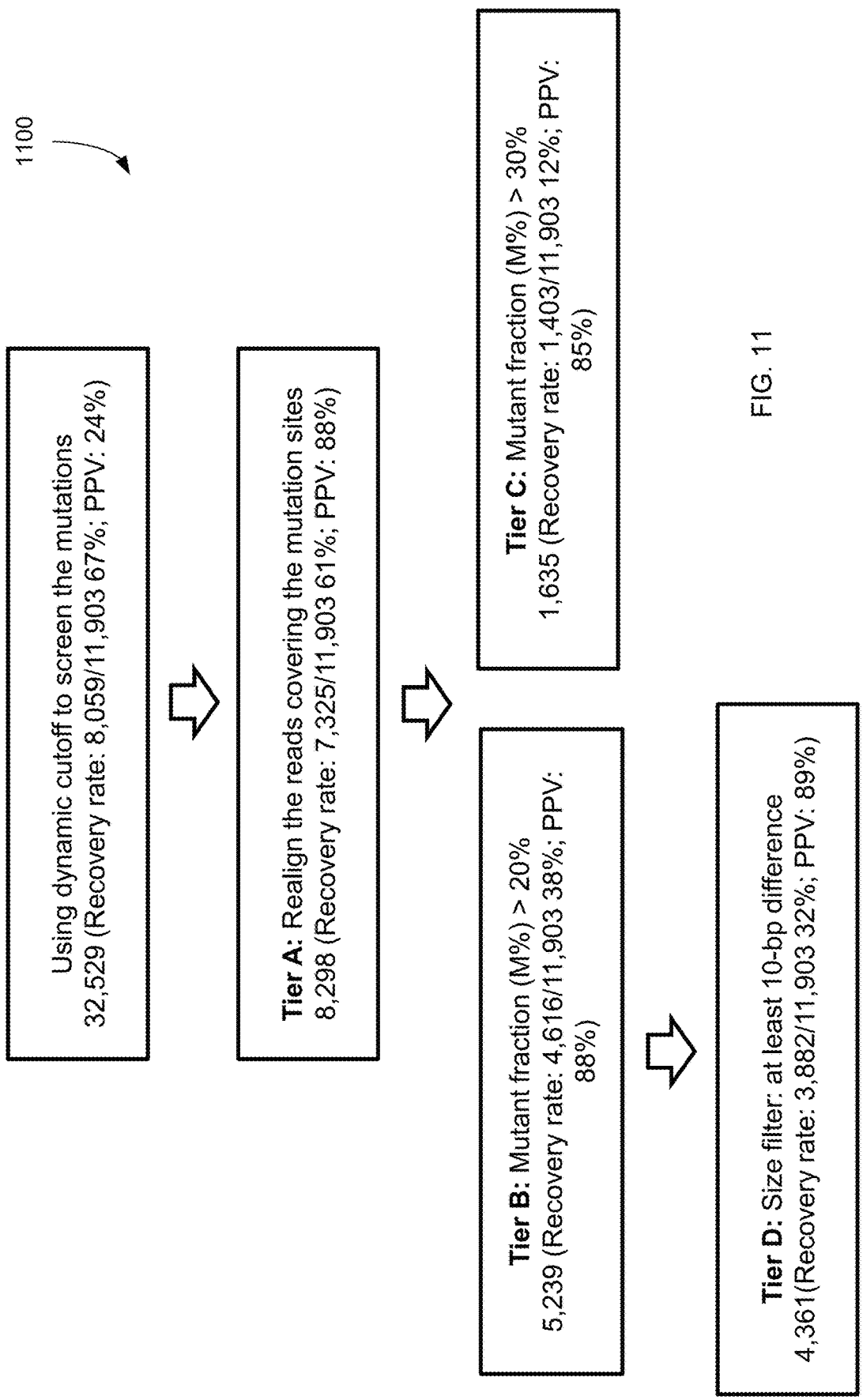
FIG. 11 shows a filtering process 1100 (which uses dynamic cutoff, realignment, mutation fraction, and size), and the resulting data for mutations identified from plasma according to embodiments of the present invention.

FIG. 11 shows a filtering process 1100 (which uses dynamic cutoff, realignment, mutation fraction, and size), and the resulting data for mutations identified from plasma according to embodiments of the present invention. In FIG. 11, the number of putative somatic mutations is shown in each box for each filtering step. The number of true somatic mutations recovered at each filtering step, among the 11,903 identified from the tumor biopsy, is shown as an absolute number as well as a percentage. The PPV for each filtering step are calculated and are also shown. PPVs of over 85% could be achieved when the Tier B, C or D criterion were used in combination with the dynamic cutoff and Tier A filtering.

Figure 12:
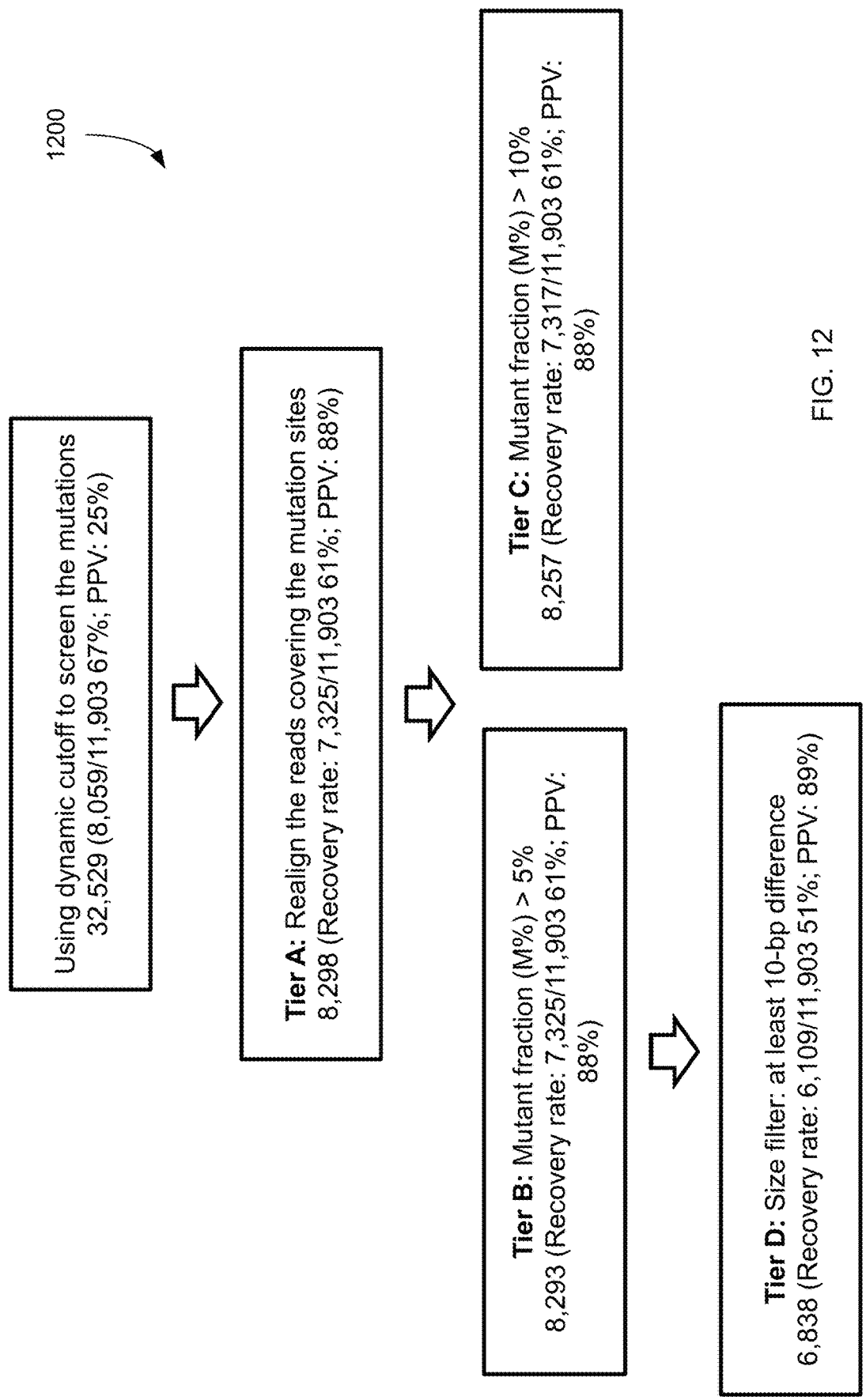
FIG. 12 shows a filtering process 1200 and the resulting data for mutations identified from plasma using lower mutant fraction cutoffs according to embodiments of the present invention.

FIG. 12 shows a filtering process 1200 and the resulting data for mutations identified from plasma using lower mutant fraction cutoffs according to embodiments of the present invention. The data in FIG. 12 shows that the PPV could be maintained while the number of true somatic mutations recovered was much higher when lower fractional concentration cutoffs were applied at Tier B or Tier C.

D. Size

We then explored the effect of omitting the fractional concentration cutoffs (Tiers B and C).

FIG. 13 shows a filtering process 1300 (which uses dynamic cutoff, realignment, and size), and the resulting data for mutations identified from plasma according to embodiments of the present invention. The data shown in FIG. 13 indicate that the same recovery and PPV could be achieved with the use of dynamic cutoff, realignment and the size requirement (namely with a preference for short DNA molecules), as was achieved with also using the mutant fraction filtering criterion.

Figure 14:
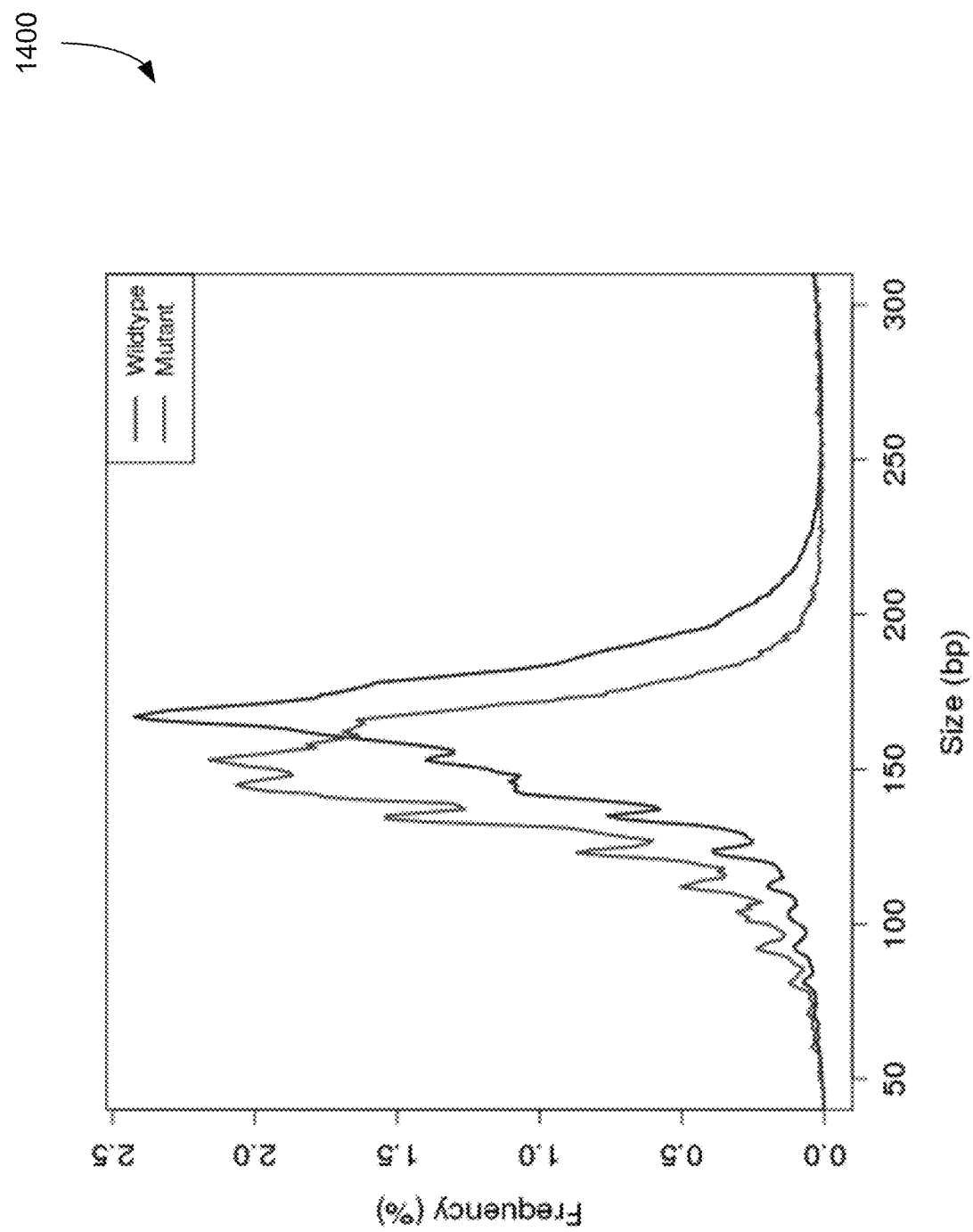
FIG. 14 shows a plot 1400 of sizes of plasma DNA fragments identified as having a mutant allele using plasma compared to the sizes of plasma DNA fragments identified as having the wildtype allele.

FIG. 14 shows a plot 1400 of sizes of plasma DNA fragments identified as having a mutant allele using plasma compared to the sizes of plasma DNA fragments identified as having the wildtype allele. The size profiles show that the mutations identified using the filtering steps exhibited short DNA size as expected for tumor-derived DNA.

E. Increased the Sequencing Depth

We further increased the sequencing depth of the plasma sample from 110× to 220×.

Figure 15:
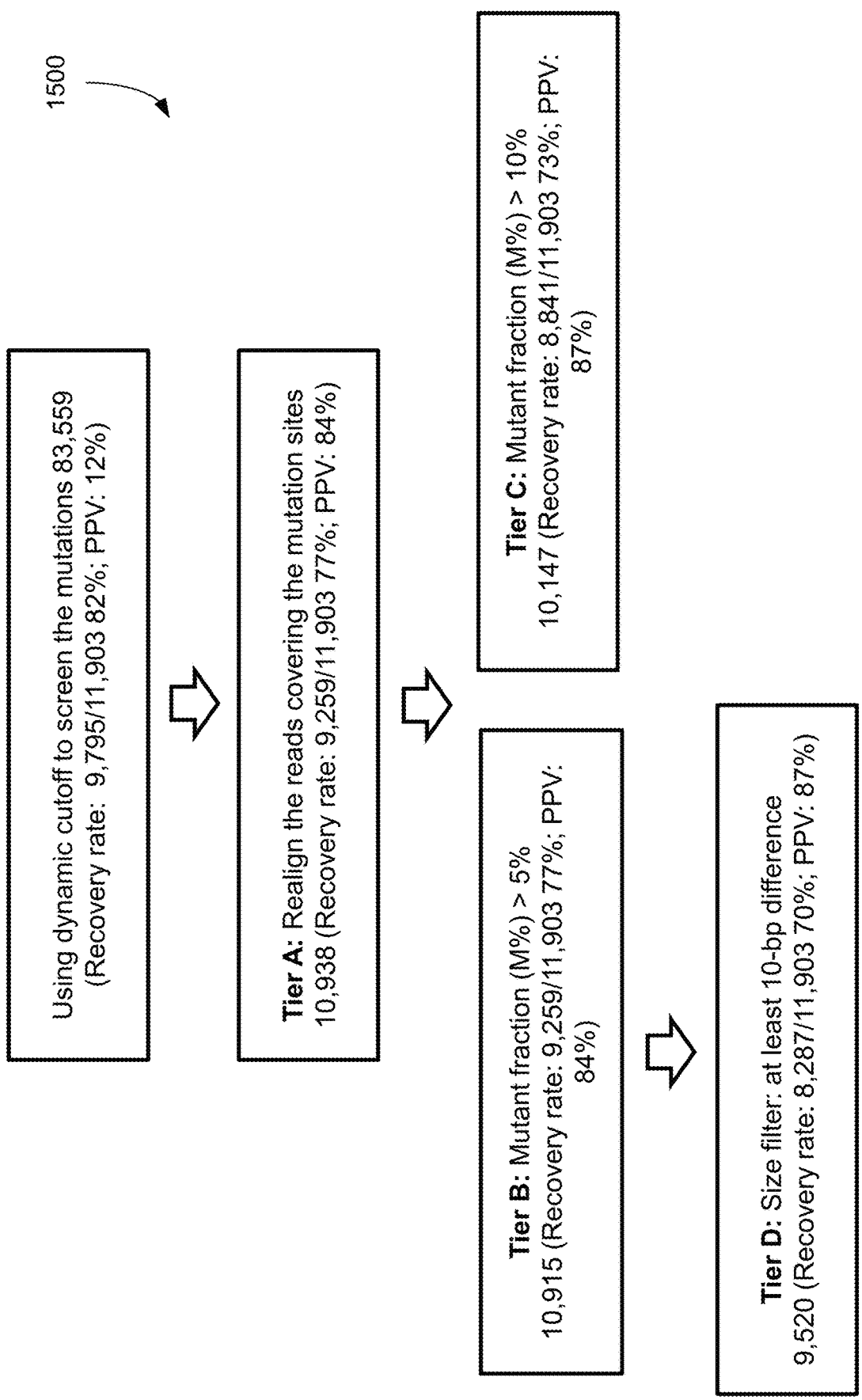
FIG. 15 shows a filtering process 1500 and the resulting data for mutations identified from plasma using increased sequencing depth according to embodiments of the present invention.

FIG. 15 shows a filtering process 1500 and the resulting data for mutations identified from plasma using increased sequencing depth according to embodiments of the present invention. Process 1500 uses the same set of filtering criteria as that shown in FIG. 12. With the increased sequencing depth (220×), the proportion of true somatic mutations recovered was much higher. Of the 10,915 mutations detected at the Tier B filtering step, 93 mutations were located within exons. Only one mutation, namely a non-synonymous change in exon 3 of CTNNB1 (c.C98G, P.S33C), was reported as one of the top 28 prevalent cancer mutations in the COSMIC database.

F. Mutant Fraction

FIG. 11 showed the effects on PPV and recovery rate when the Tier B and Tier C cutoffs were 20% and 30%, respectively. A lower M % may be used as a cutoff if higher sensitivity in mutation identification is preferred. FIG. 12 shows the effects on PPV and recovery rate when the Tier B cutoff was 5% and Tier C cutoff was 10%.

As described above, a variance in mutant fraction can also be used as a filtering criterion. We studied the plasma allelic fraction of somatic mutant fraction, originating from different chromosomal regions. As shown in FIG. 6, the tumor of the HCC patient demonstrated copy number loss in chromosome 1p and copy number gain in chromosome 1q. We plotted the frequency distribution of the mutant fractions across chromosome 1p and chromosome 1q.

Figure 16:
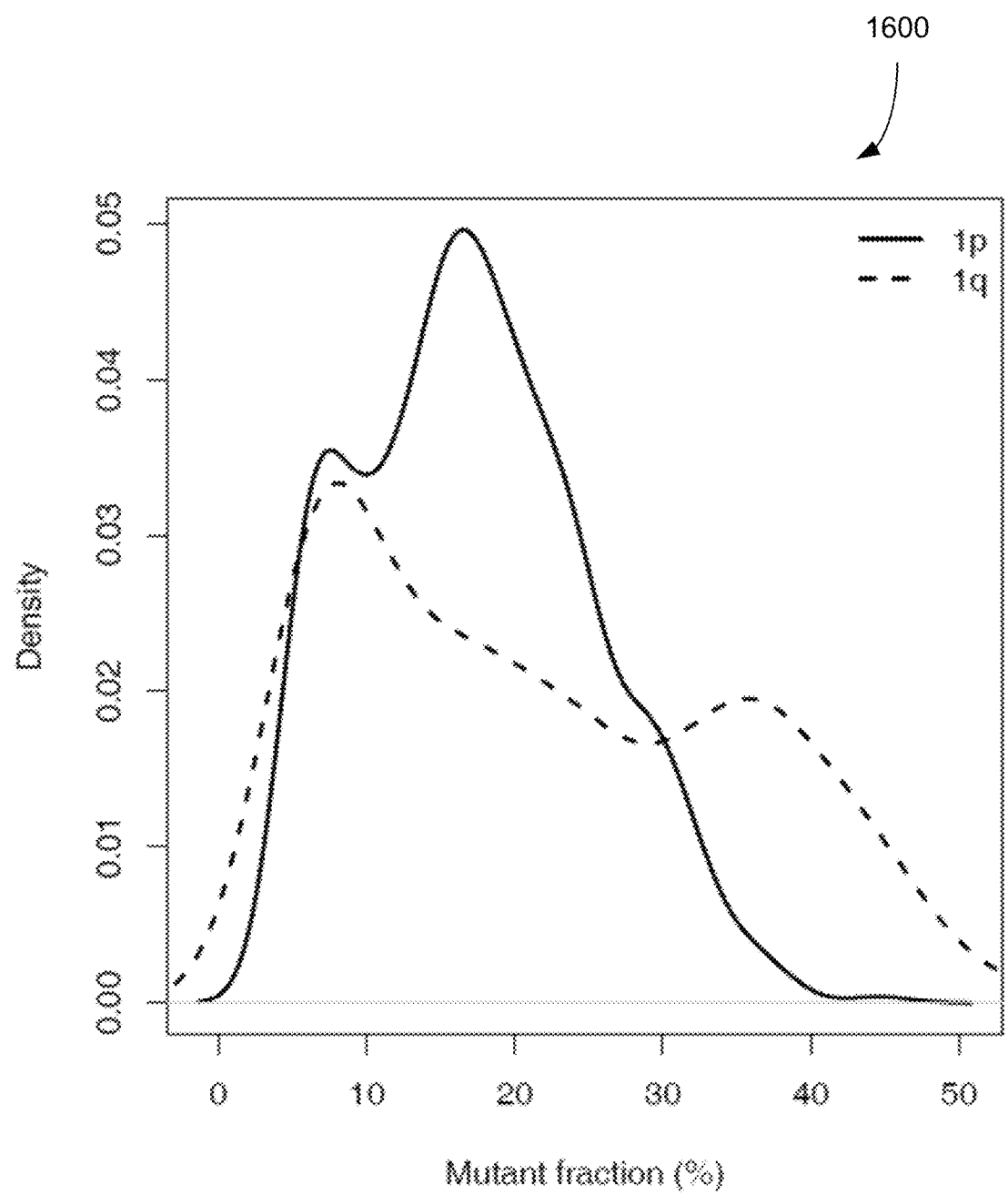
FIG. 16 is a plot 1600 showing the number (density) of loci having various values of mutant fraction.

FIG. 16 is a plot 1600 showing the number (density) of loci having various values of mutant fraction. As seen in plot 1600, higher values of mutant fractions were observed for the copy number gain region (chromosome 1q) and lower mutant fraction values were observed for the copy number loss region (chromosome 1p).

We also studied the range of values and variance of the mutant fraction values in the two regions.

Figure 17A:
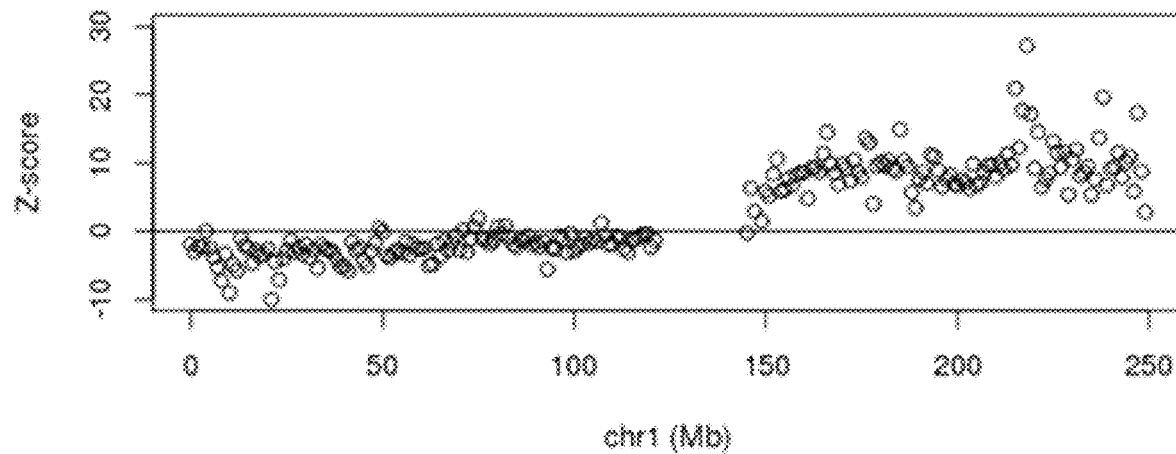
FIG. 17A shows z-scores for the distribution over chromosome arms 1p and 1q.
Figure 17B:
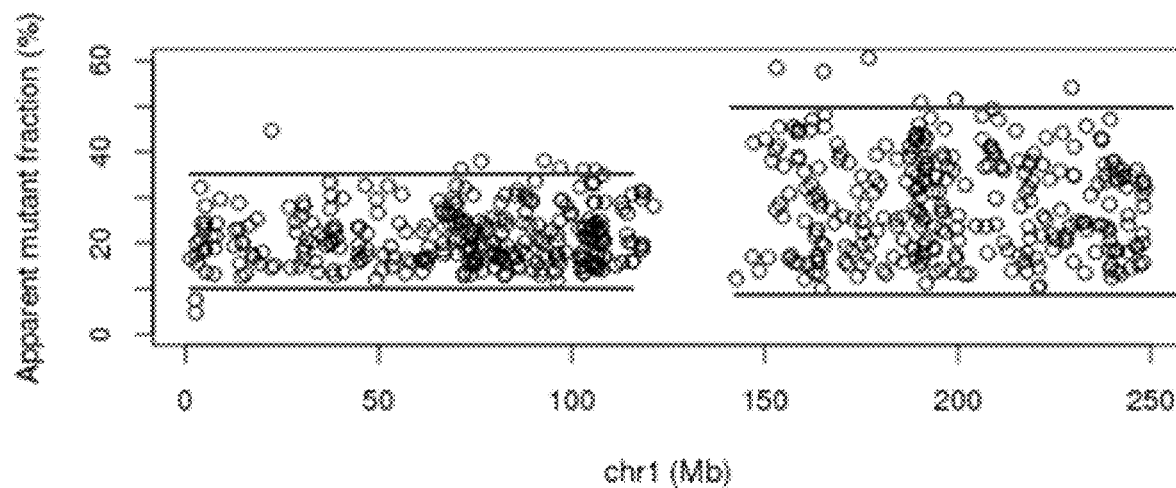
FIG. 17B shows the apparent mutant fraction over chromosome arms 1p and 1q.

FIG. 17A shows z-scores for the distribution over chromosome arms 1p and 1q. FIG. 17B shows the apparent mutant fraction over chromosome arms 1p and 1q. The z-scores of the distribution of values were higher (FIG. 17A) and the actual values were more variable (FIG. 17B) in the copy number gain region (chromosome 1q) than the copy number loss region (chromosome 1p).

These data suggest that different M % could be set as filtering cutoffs for regions with copy number gains or losses to increase the likelihood of identifying true somatic mutations. Cutoffs specifying the variance in the observed plasma mutant fraction could also be used to identify plasma DNA molecules that have originated from chromosomal regions that are more likely to be enriched with (as for regions with copy number gains) or are depleted of (as for regions with copy number losses) tumor-derived DNA. A decision could then be made regarding the likelihood of the DNA fragment being an informative cancer DNA fragment.

G. Less Stringent Criteria

We explored if less stringent criteria could be used in the dynamic cutoff. In the examples shown earlier, dynamic cutoff threshold (Score3) used was to minimize the change of false-positive identification of somatic mutation. For the dynamic cutoff analysis, a sequence variant would be qualified as a candidate mutation when the sequence variant is present in a number (N) of sequenced DNA fragments, where the number (N) is dependent on the number of loci sequenced, the number of nucleotides in the search space, and the probability of having the predicted false-positive rate. In the previous example, the predicted false-positive rate was set as $<10^{-10}$, and the search space is the whole genome ($3 \times 10^9$ nucleotides).

FIG. 18 is a table 1800 showing predicted sensitivities of mutation detection for various mutation fractions and sequencing depths for certain allelic count cutoffs according to embodiments of the present invention. Each row corresponds to a different sequencing depth. The cutoff in plasma is used for determining whether the number of DNA fragments with the mutation in plasma is sufficient to be considered as a mutation. Using these values the remaining columns provide the predicted sensitivity, TP/(TP+FN), of mutation detection in plasma for various tumor percentages. The buffy coat is also subjected to a cutoff to filter sequencing errors in the buffy coat. Without such a filter, embodiments might miss including the locus as a homozygous site for variant detection in plasma, since some embodiments only detect variants that fall on locations where the buffy coat is homozygous. The data in table 1800 serves as baseline data to interpret the next graph when less stringent dynamic cutoffs are used.

We explored the effects of loosening the threshold to allow for a false-positive detection rate of 0.1%.

FIG. 19 is a table 1900 showing predicted sensitivities of mutation detection for various mutation fractions and sequencing depths for certain allelic count cutoffs for a false-positive detection rate of 0.1% according to embodiments of the present invention. This data shows data for a less stringent dynamic cutoff.

Figure 20:
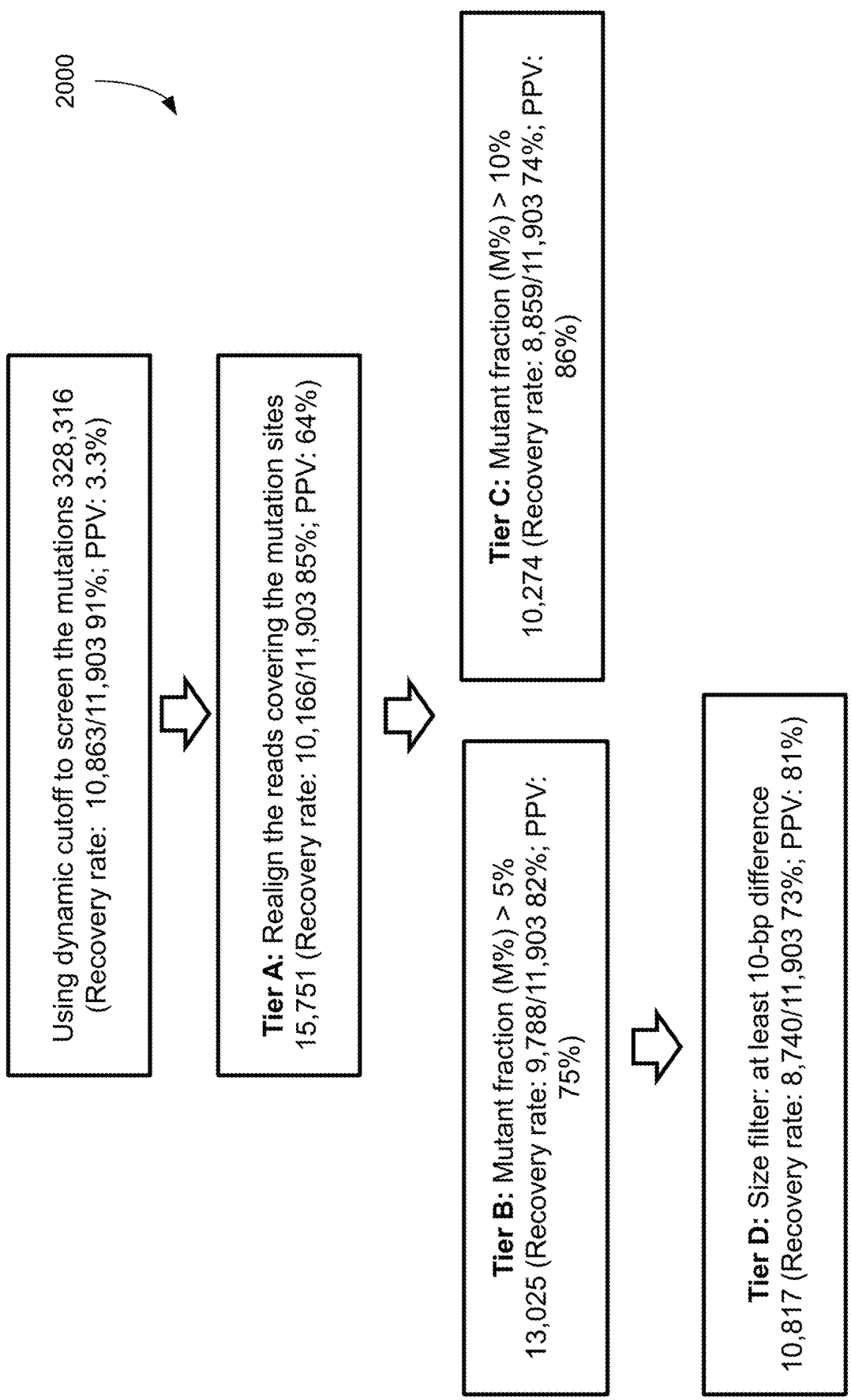
FIG. 20 shows a filtering process 2000 and the resulting data for mutations identified from plasma using a less stringent dynamic cutoff according to embodiments of the present invention.

FIG. 20 shows a filtering process 2000 and the resulting data for mutations identified from plasma using a less stringent dynamic cutoff according to embodiments of the present invention. A sequencing depth of 220× was used. When the less stringent dynamic cutoff was used, the PPV at the first step dropped from 12% to 3.3%. When combined with the other filtering steps, namely Tiers A, B, C and D, higher recovery of the true somatic mutations could be achieved with PPVs similar to algorithms based on stringent dynamic cutoffs.

These data suggest that each filtering criterion play a different role. The utility of each criterion could be changed by altering the stringency of the thresholds used. In this example, the less stringent dynamic cutoff allowed the more sensitive identification of somatic mutations. The specificity of the overall scheme was maintained due to the effectiveness of the other criteria in filtering out the false-positives.

Next, we further assessed the complete removal of the dynamic cutoff step. Instead, fixed cutoffs were applied. For example, we determined the number of putative mutations identified if a heterozygous allele not present in the buffy coat DNA is seen at least a specific number of times (e.g., 1, 2, 3, etc.) in plasma. We applied this analysis to analyze the plasma DNA data of the HCC patient as well as a maternal plasma sample sequenced to over 200×. The mother who contributed the maternal plasma sample was not known to have cancer and therefore most of the putative mutations identified in this sample are likely to be paternally-inherited fetal specific alleles or false-positives.

Figure 21:
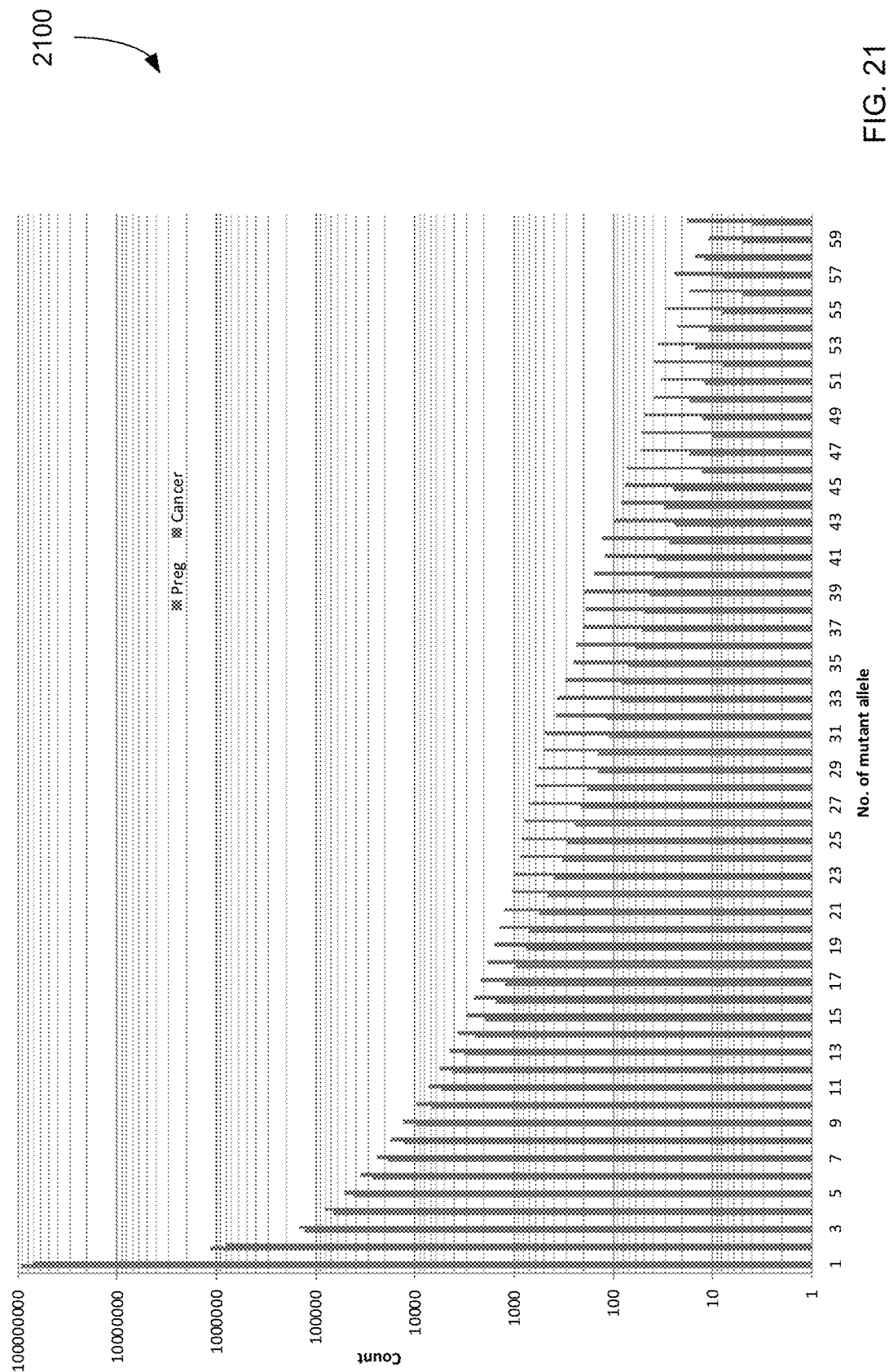
FIG. 21 is a plot 2100 showing the distributions of the number of putative mutations for fetal and cancer scenarios.

FIG. 21 is a plot 2100 showing the distributions of the number of putative mutations for fetal and cancer scenarios. The vertical axis corresponds to a count of the number of loci with a putative mutation (mutant allele). The horizontal axis corresponds to the number of DNA fragments required for a locus to be identified as having a mutation.

Both samples have been sequenced to similar depth using PCR-free library preparation protocols. Thus, the false-positive mutations contributed by the sequencing errors and alignment errors should be similar in both samples. It is noted that the number of putative mutations decreased as the number of sequence reads used as a cutoff for the scoring of a mutation increased. Because the false-positive mutations tend to occur randomly and are therefore present at lower allelic ratios, it is likely that the false-positives are being filtered out with the progressive increase in the number of reads required as a cutoff.

On the other hand, one could observe that the number of putative mutations identified in the cancer patient started to demarcate and was higher than that detected in the plasma of the pregnant woman from a cutoff of around 18 sequence reads and onwards. This means that the mutational load in the HCC patient is higher than the number of paternally inherited fetal alleles in the maternal plasma sample.

We then applied the realignment (Tier A) filtering criteria to the same dataset.

Figure 22:
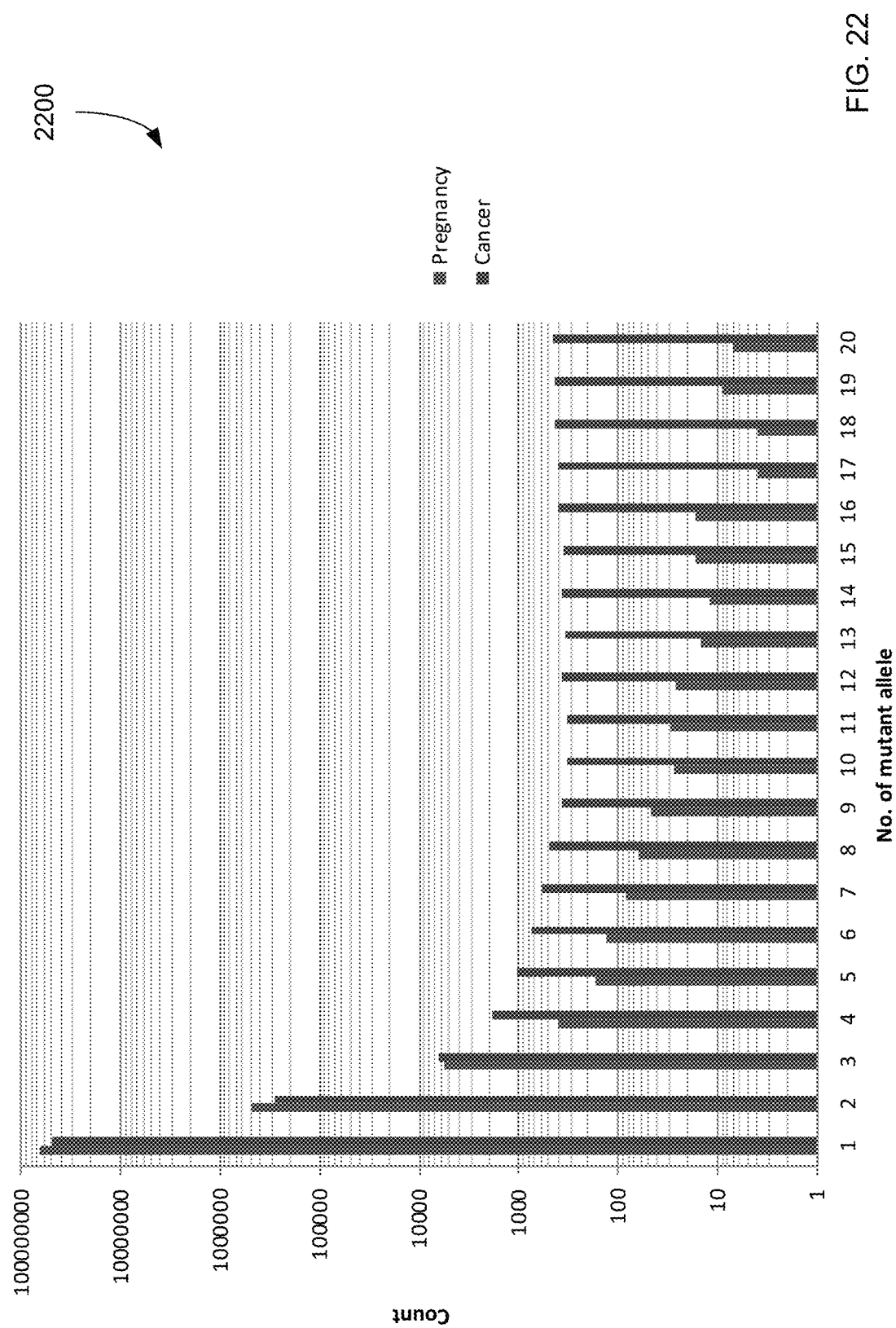
FIG. 22 is a plot 2200 showing the distributions of the number of putative mutations for fetal and cancer scenarios when realignment is used.

FIG. 22 is a plot 2200 showing the distributions of the number of putative mutations for fetal and cancer scenarios when realignment is used. The overall numbers of putative mutations decreased substantially even at corresponding fixed sequence read cutoff numbers when compared with the data shown in FIG. 21 when realignment was not applied. The demarcation in the number of putative mutations between the HCC plasma and the maternal plasma was even more obvious. These data suggest that the realignment step is a powerful process for removing false-positives.

We further assessed the value of size filtering. Again, the dynamic cutoff strategy is not used in this analysis. Instead, a fixed minimum number of sequence reads showing the same minor allele was used as the first step to identify putative mutations.

FIG. 23 is a table 2300 showing PPVs and recovery rates for various size cutoffs without realignment according to embodiments of the present invention. As shown in FIG. 23, the PPVs for somatic mutation identification using the fixed cutoffs alone were suboptimal. When different size cutoffs were used at each fixed cutoff level, the PPVs improved.

FIG. 24 is a table 2400 showing PPVs and recovery rates for various size cutoffs with realignment according to embodiments of the present invention. For the data shown in FIG. 24, realignment was applied after the initial identification of putative mutations by the fixed cutoffs. The PPVs improved substantially. Then different size cutoffs were applied for further filtering, some improvement in the PPV was observed.

H. Detection of Elevated Mutational Load in Cancer

We performed mutational load assessment using the filtering criterion described for the plasma sample from the HCC patient and the plasma of a cord blood sample of a neonate. The constitutional genome for the cord blood sample was the cord blood buffy coat. The cord blood plasma works well as a control since most babies are born without cancer and they have not yet acquired somatic mutations or been exposed to carcinogens.

The cord blood plasma was sequenced to 75× using a PCR-free library preparation protocol.

Figure 25:
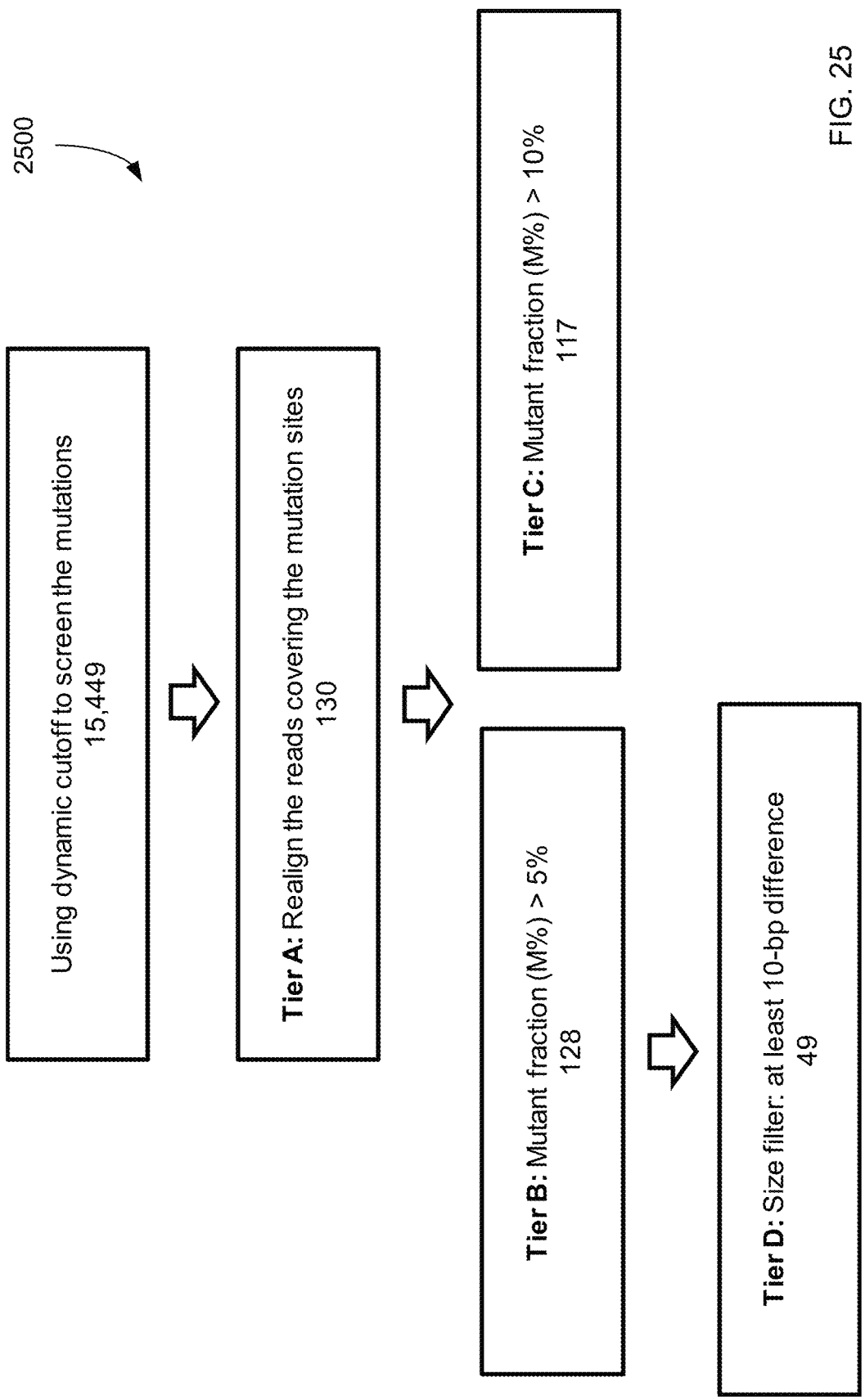
FIG. 25 shows a filtering process 2500 (which uses dynamic cutoff, realignment, and size), and the resulting data for mutations identified from cord blood plasma according to embodiments of the present invention.

FIG. 25 shows a filtering process 2500 (which uses dynamic cutoff, realignment, and size), and the resulting data for mutations identified from cord blood plasma according to embodiments of the present invention. FIG. 25 shows the number of putative mutations detected in the cord blood plasma when a stringent dynamic cutoff was used followed by the Tiers A to D criteria shown in the figure. A small number of putative mutations were identified.

Figure 26:
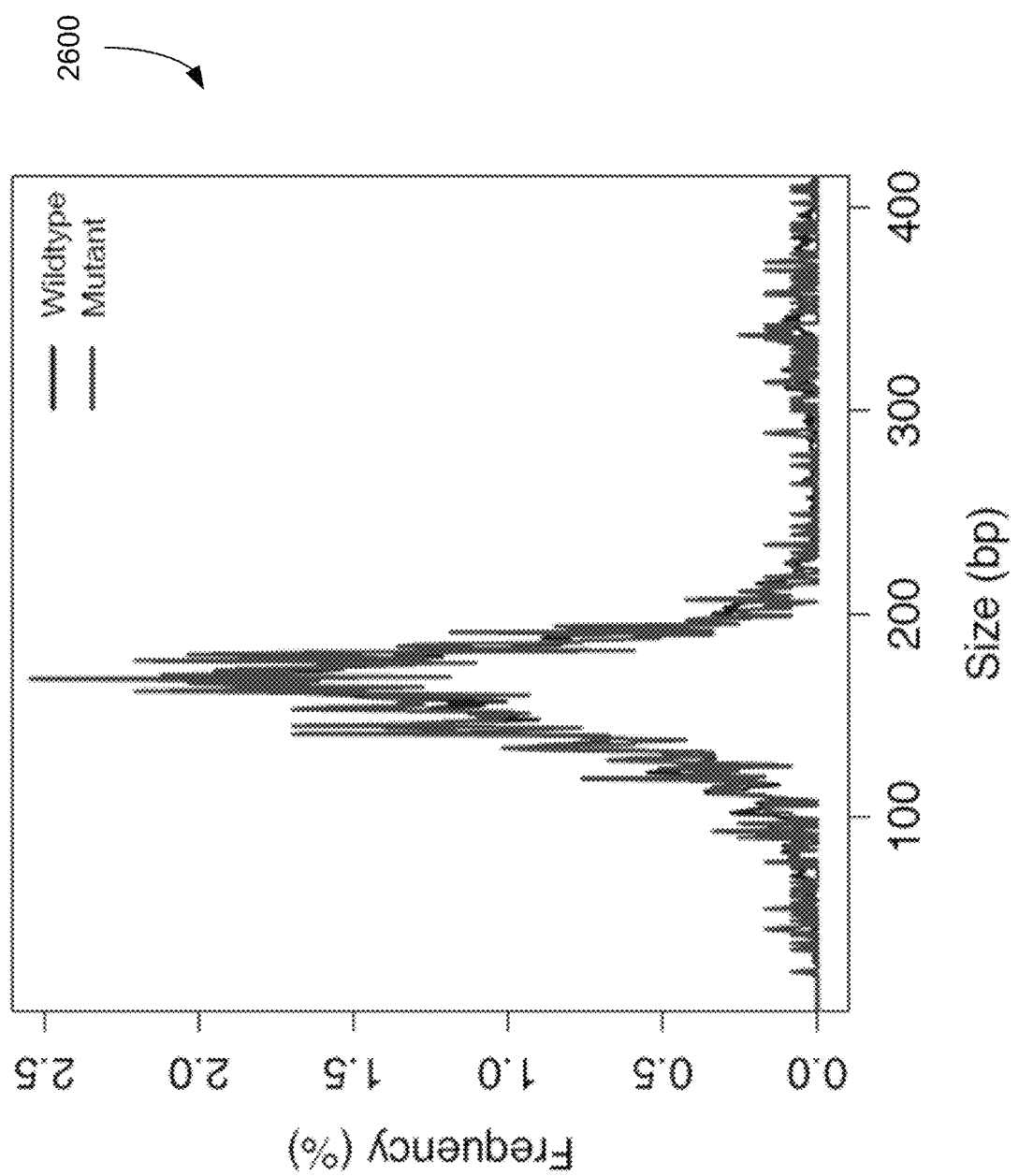
FIG. 26 is a plot 2600 of size distributions for mutant DNA fragments determined from process 2500 and wildtype alleles according to embodiments of the present invention.

FIG. 26 is a plot 2600 of size distributions for mutant DNA fragments determined from process 2500 and wildtype alleles according to embodiments of the present invention. When we assessed the size profile of these mutations, they were not particularly short which is unlike cancer derived DNA.

Figure 27:
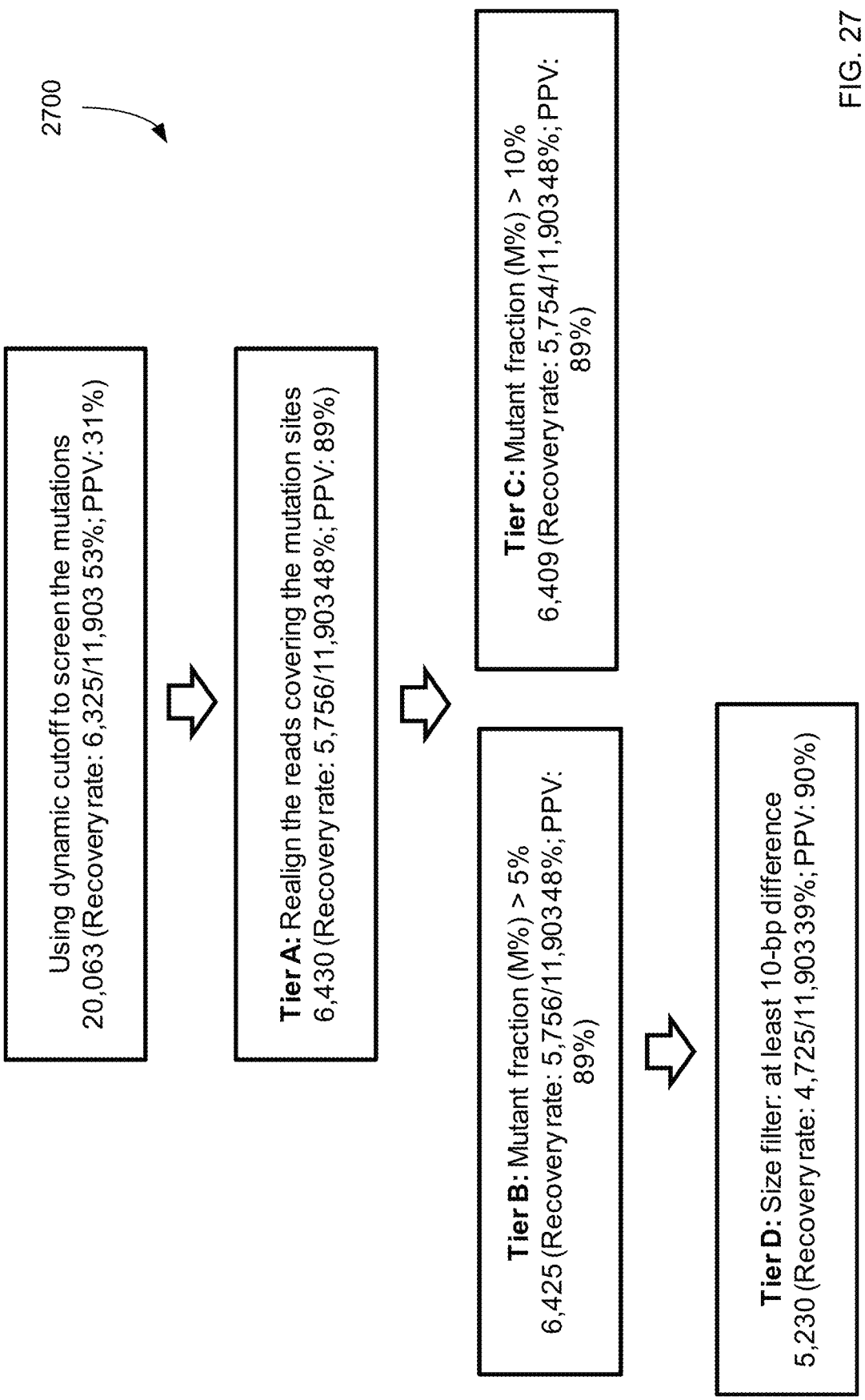
FIG. 27 shows a filtering process 2700 (which uses dynamic cutoff, realignment, and size), and the resulting data for mutations identified from plasma of an HCC sample according to embodiments of the present invention.

Next, we randomly picked 75× of plasma DNA sequence data from the HCC sample so that a comparable assessment could be made. The same set of filtering criteria was applied. About 5,000 to 6,000 of the tumor-derived mutations were recovered at PPVs 89% or above FIG. 27 shows a filtering process 2700 (which uses dynamic cutoff, realignment, and size), and the resulting data for mutations identified from plasma of an HCC sample according to embodiments of the present invention. A sequencing depth of 75× was used.

Figure 28:
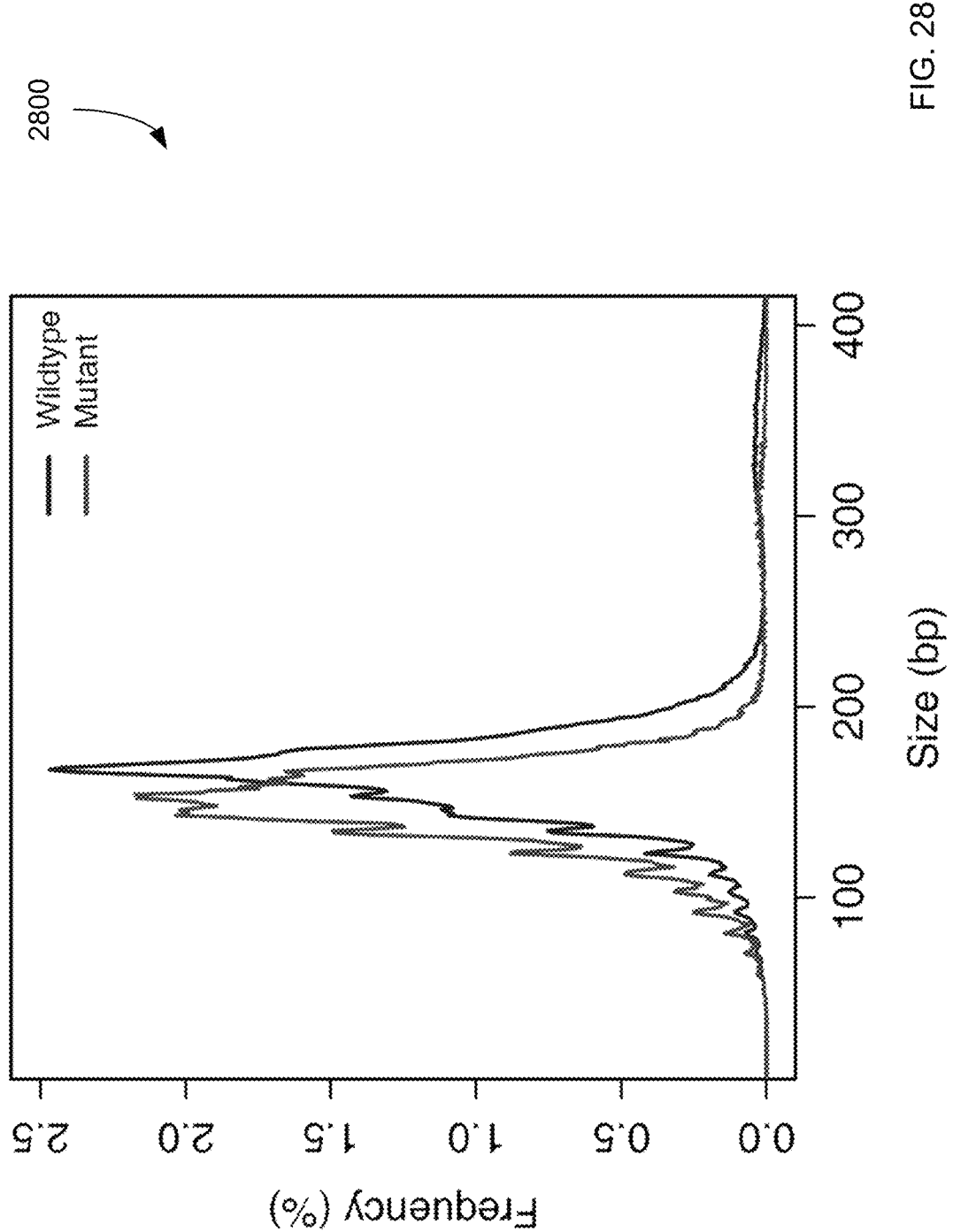
FIG. 28 is a plot 2800 of size distributions for mutant DNA fragments determined from process 2700 and wildtype alleles according to embodiments of the present invention.

FIG. 28 is a plot 2800 of size distributions for mutant DNA fragments determined from process 2700 and wildtype alleles according to embodiments of the present invention. Plasma DNA fragments with these mutations were indeed shorter than the non-informative DNA fragments.

However, it was noted that 84% of the putative mutations identified in the cord blood plasma occurred on publicly-reported single nucleotide polymorphism sites while this proportion was only 3% in the HCC plasma sample. We therefore hypothesized that the publicly-reported alleles in the cord blood plasma may be maternal DNA molecules that have trafficked into the fetal circulation and remained detectable in the neonatal blood (Lo et al. Clin Chem 2000; 46:1301-1309). After removing any sites from known single nucleotide polymorphism sites, the number of putative mutations in the cord blood plasma decreased to just 8 (FIG. 29) while the data for the HCC plasma remained largely unchanged (FIG. 30).

Figure 29:
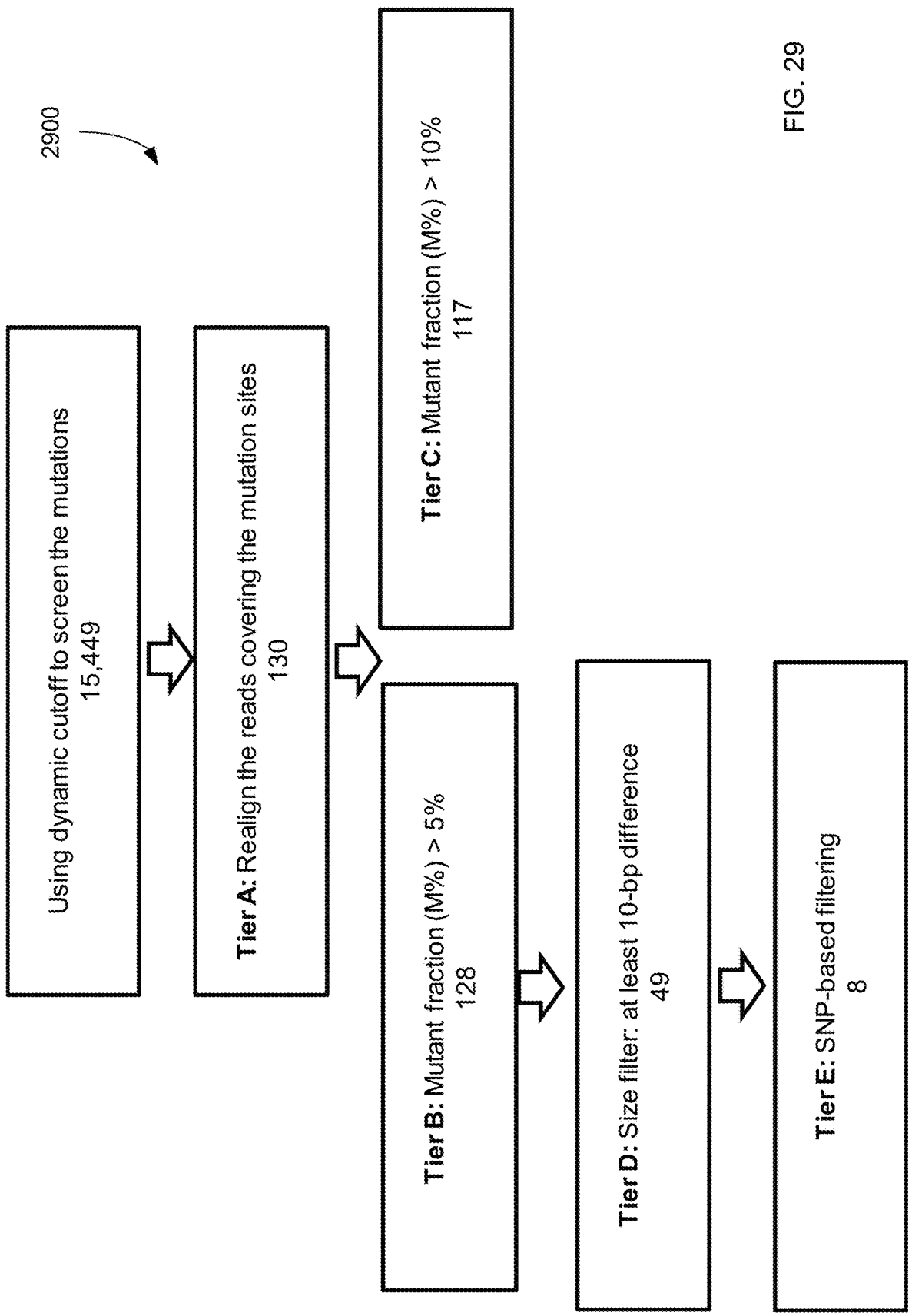
FIG. 29 shows a filtering process 2900 that uses SNP-based filtering for mutations identified from cord blood plasma according to embodiments of the present invention.
Figure 30:
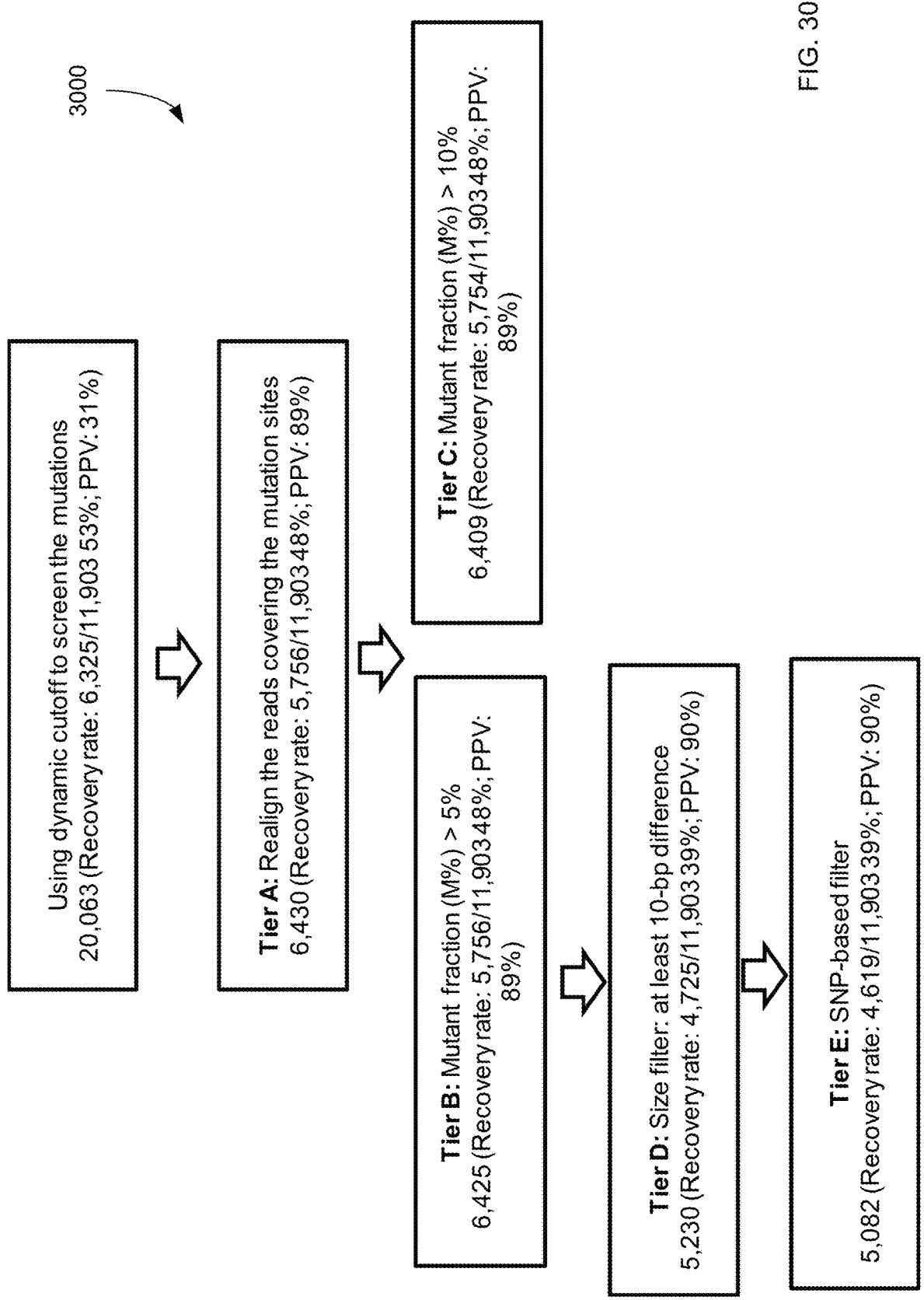
FIG. 30 shows a filtering process 3000 that uses SNP-based filtering for mutations identified from HCC plasma according to embodiments of the present invention.

FIG. 29 shows a filtering process 2900 that uses SNP-based filtering for mutations identified from cord blood plasma according to embodiments of the present invention. FIG. 30 shows a filtering process 3000 that uses SNP-based filtering for mutations identified from HCC plasma according to embodiments of the present invention. Incorporation of a filtering step to remove single nucleotide polymorphisms corresponds to Tier E filtering. Consequently, the number of putative mutations (which are mostly false-positives) detected in the cord blood plasma was reduced by 84% (8 out of 49). On the other hand, the number of putative mutations in the HCC sample has only been reduced by 3%.

Our data show that using the PCR-free library preparation protocol followed by ultra-deep and broad sequencing with the incorporation of the described set of filtering criteria, we were able to sensitively and specifically identify tumor-derived mutations in the plasma of a cancer patient based on the number of putative mutations identified. The mutational load identified in the plasma of the cancer patient exceeded that observed in the control non-cancer cord blood plasma by 3 orders of magnitude. Thus, the classification between cancer and non-cancer could be made.

We further showed that a subsample (75×) of the total sequenced data (220×) was already adequate for the purpose of achieving discrimination between cancer and non-cancer. As shown in simulation data below (FIGS. 44, 45A-45C, and 46A-46C of section VIII), while ultra-deep and broad sequence data are needed in these embodiments, the extent of the breadth and depth is dependent on the tumor DNA fraction in the plasma sample and the number of mutations harbored by the tumor that are amenable to plasma DNA detection.

I. Tissue of Origin

There are now data (Snyder et al. Cell 2016; 164: 57-68; PCT WO 2016/015058 A2; Ivanov et al. BMC Genomics 2015; 16 Suppl 13:S1) to suggest that the genomic location of such somatic mutations may show patterns of clustering depending on the tissue of origin of the tumor. The literature suggested that somatic mutations tended to be co-localized with genomic locations with specific histone modifications. The tissue-specific locations of histone modifications could be obtained through public databases such as the Epigenomics Roadmap database (www.roadmapepigenomics.org).

We obtained the tissue-specific locations of histone modifications through Epigenomics Roadmap database (www.roadmapepigenomics.org). In healthy tissues, H3K4me1 are reported to be associated with active/poised enhancer regions. H3K27ac is associated with active enhancer regions. H3K9me3 is highly correlated with constitutive heterochromatin. In other words, in healthy tissues, H3K4me1 and H3K27ac are associated with genomic regions with active gene expression in the tissue while H3K9me3 is associated with the repressed regions of the genome. However, it has been reported in cancer that the number of somatic mutations are more highly represented in the repressed genomic regions. No data to date has reported the existence of such a correlation in plasma DNA.

We performed Spearman correlation analysis between the number of each one of the three histone modifications per 1-Mb bin and the number of somatic mutations in the same 10 Mb bin.

Figure 31:
FIG. 31 is a table 3100 showing correlations of tissue with histone modifications.

FIG. 31 is a table 3100 showing correlations of tissue with histone modifications. FIG. 31 uses SNVs to determine tissue of origin of tumor prediction. The strongest correlation coefficient was obtained for the liver tissue histone modification pattern. This is consistent with the fact that the plasma DNA data were obtained from a HCC patient. Thus, if one analyzes another test sample, plasma DNA fragments originating from loci that are associated with histone modifications that are known to be associated with cancer could be identified. Such loci would be enriched with cancer-derived plasma DNA fragments. Thus, plasma DNA fragments of these loci could be classified as informative cancer DNA fragments. A similar approach can also be performed for identifying fetal mutations using histone modifications that are known to be associated with fetal tissues (e.g. the placenta).

Spearman correlation is calculated between SNV density per megabase in plasma and histone marker density per megabase in various organs or tissues. The highest correlation would suggest the tissue of origin of tumor.

VII. Detection of De Novo Mutation in Fetuses

Most of the discussion above has been related to cancer, but embodiments can also be used to identify de novo mutations in fetuses.

Congenital mutations can result in diseases that may manifest during the prenatal period, during childhood or later in life. Congenital mutations refer to mutations that are present in the fetal genome. Some diseases are amenable to early treatment while others may be associated with significant impairment in function. Thus, prenatal diagnosis of some of these diseases are warranted. Prenatal diagnosis of diseases associated with genetic, genomic or chromosomal abnormalities could be performed by analyzing fetal genetic material before birth. Fetal genetic material could be obtained by invasive procedures, such as amniocentesis or chorionic villus sampling. These procedures are associated with risks of fetal miscarriage. Thus, it is preferable to perform prenatal assessment by noninvasive approaches, including through the analysis of cell-free fetal nucleic acids that are present in maternal plasma.

Most congenital mutations are inherited from the parents and result in inherited diseases. Approaches for the noninvasive detection of inherited mutations by circulating cell-free fetal DNA analysis in maternal plasma have previously been reported (U.S. Patent Publications 2009/0087847 and 2011/0105353). The putative fetal mutations could be confirmed by knowing or testing the maternal and/or paternal mutations.

However, diseases are also caused by de novo mutations. De novo mutations are mutations present in the constitutional genome of a fetus that are not inherited from the father or mother. De novo mutations account for a significant proportion of disease burden for certain diseases, e.g. achondroplasia, multiple endocrine neoplasia. It has been estimated that each person has some 20 to 30 de novo mutations in the constitutional genome (Kong et al. Nature 2012; 488: 471-475). Such mutations may cause disease if they occur at regions of the genome that would impair genetic, epigenetic or regulatory function of the genome. There are currently no effective method for the prenatal detection of de novo mutations unless there is known a priori risk. A priori suspicion for a de novo mutation could be developed if for e.g. an ultrasonography of the fetus reveal features suspicious of achondroplasia. If both parents do not carry mutations for achondroplasia, then a de novo mutation will be searched for in the fibroblast growth factor receptor 3 gene.

For most other diseases that are caused by de novo mutations, there are typically no structural or physical signs that could be detected prenatally to suggest which gene to investigate. There are currently no effective method to detect de novo mutations prenatally because the search for 30 of such changes within the 3 billion nucleotides of the haplotype genome is like looking for a needle in the haystack. To achieve de novo mutation detection by circulating cell-free fetal DNA analysis is associated with much greater difficulty because of the background plasma DNA of the mother which further dilutes the fetal de novo mutations by 5- to 10-fold. Here we describe embodiments that would allow the effective detection of fetal de novo mutations through the analysis of circulating cell-free fetal DNA in maternal plasma.

A. Example for Detection of De Novo Mutation in Fetus

1. Family Information

A singleton pregnancy with a male fetus was scheduled for cesarean section at the $38^{th}$ week of pregnancy. The family was recruited at the Department of Obstetrics and Gynaecology, Prince of Wales Hospital with informed consent. The study was approved by the Joint Chinese University of Hong Kong and New Territories East Cluster Clinical Research Ethics Committee. 20 mL of maternal blood and 10 mL of paternal blood were collected during admission. Placental tissue sample and 3 mL of cord blood were collected after delivery.

2. Sample Processing

All blood samples were processed by a double centrifugation protocol as described previously (Chiu et al Clin Chem 2001; 37: 1607-1613). Briefly, after centrifugation at 1,600 g for 10 min at 4° C., the plasma portion was recentrifuged at 16,000 g for 10 min at 4° C. to remove the blood cells. The blood cell portion was recentrifuged at 2,500 g, and any residual plasma was removed. DNA from the blood cells and that from maternal plasma was extracted with the blood and body fluid protocol of the QIAamp DNA Blood Mini Kit and the QIAamp DSP DNA Blood Mini Kit, respectively (Qiagen). DNA from the placenta was extracted with the QIAamp DNA Mini Kit (Qiagen) according to the manufacturer's tissue protocol.

3. Quantification of Plasma DNA

DNA was extracted from 5 mL of maternal plasma. Using the ZFX/Y digital PCR assay (Lun et al Clin Chem 2008; 54: 1664-1672), the concentration of ZFX and ZFY was 1,038 copies/mL plasma and 103 copies/mL plasma, respectively.

We then used 4.5 mL-equivalent of plasma DNA for library construction. Assume that each genome is broken into 166 base pair (bp) fragments, there should be about $1.81 \times 10^7$ plasma DNA fragments per genome. The 4.5 mL plasma DNA should contain $(1038+103) \times 4.5 \times 1.81 \times 10^7$ fragments=$9.28 \times 10^{10}$ total fragments.

4. DNA Library Construction

DNA libraries for the genomic DNA samples and the maternal plasma sample were constructed with the TruSeq DNA PCR-free Library Preparation kit (Illumina) according to the manufacturer's protocol except that one-fifth of the indexed adapter was used for plasma DNA library construction. There were four genomic DNA samples, namely the mother's buffy coat DNA, the father's buffy coat DNA, the cord blood buffy coat DNA and the placenta DNA. For each genomic DNA samples, one microgram DNA was sonicated to 200 bp fragments (Covaris) for library construction. The library concentrations ranged from 34 to 58 nM in 20 µL library. For the maternal plasma DNA sample from 4.5 mL plasma ($9.28 \times 10^{10}$ fragments), the library yield was 2995 pM in 20 µL library, which equaled 59,910 amoles, i.e., $3.61 \times 10^{10}$ 166-bp plasma DNA fragments. The conversion from DNA to library was 38.9%.

5. Sequencing of DNA Libraries

All DNA libraries were sequenced on the HiSeq 1500, HiSeq 2000 or HiSeq 2500 sequencing platforms (Illumina) for 75 bp×2 (paired-end). We sequenced multiple lanes for each genomic DNA library. The sequencing depths of the mother's, father's, cord's and placental DNA libraries were 40×, 45×, 50× and 30×, respectively. All of the maternal plasma DNA library was used for sequencing. We exhausted the library with 45 lanes, and obtained approximately 5.74 billion non-duplicated mapped paired-end reads. The sequencing depth was ~255×.

To calculate the recovery of the plasma DNA library, we used 16 µl DNA library at 2,995 nM as input (4 µL from the 20 µL DNA library were used for library validation and quantification). The total number of fragments input were $2,995 \times 16 \times 6.02 \times 10^{23}/10^9 = 2.89 \times 10^{10}$ fragments. After sequencing, we obtained $5.74 \times 10^9$ reads (fragments). The recovery of DNA library after sequencing was 19.9%. 80% of the input library was lost during cluster generation and/or sequencing. We suspected that a 5-times excess of library would be required as input to achieve a high efficiency of cluster generation on the sequencing flow cell. The excess library fragments would then be washed away, and only those formed a cluster would be sequenced.

Following the above estimation, the DNA to library conversion rate was 38.9%, and the recovery of DNA library after sequencing was 19.9%. It was estimated that from plasma DNA fragments to sequencing output fragments, the recovery was 7.7%.

B. Discussion 298,364 informative SNP sites were identified where the father and mother were both homozygous, but with a different allele. Thus, the fetus was an obligate heterozygote at these sites. 99.8% of these SNP sites were confirmed to be heterozygous in the placenta tissue. We then determined the fetal DNA fraction in the maternal plasma. Combining the counts of the paternal alleles and expressing this as a proportion of the combined counts of the maternal alleles across these 298,364 informative SNP sites, the fetal DNA fraction was estimated to be 31.8%. We then determined the fetal fraction at each of these informative SNP sites.

Figure 32:
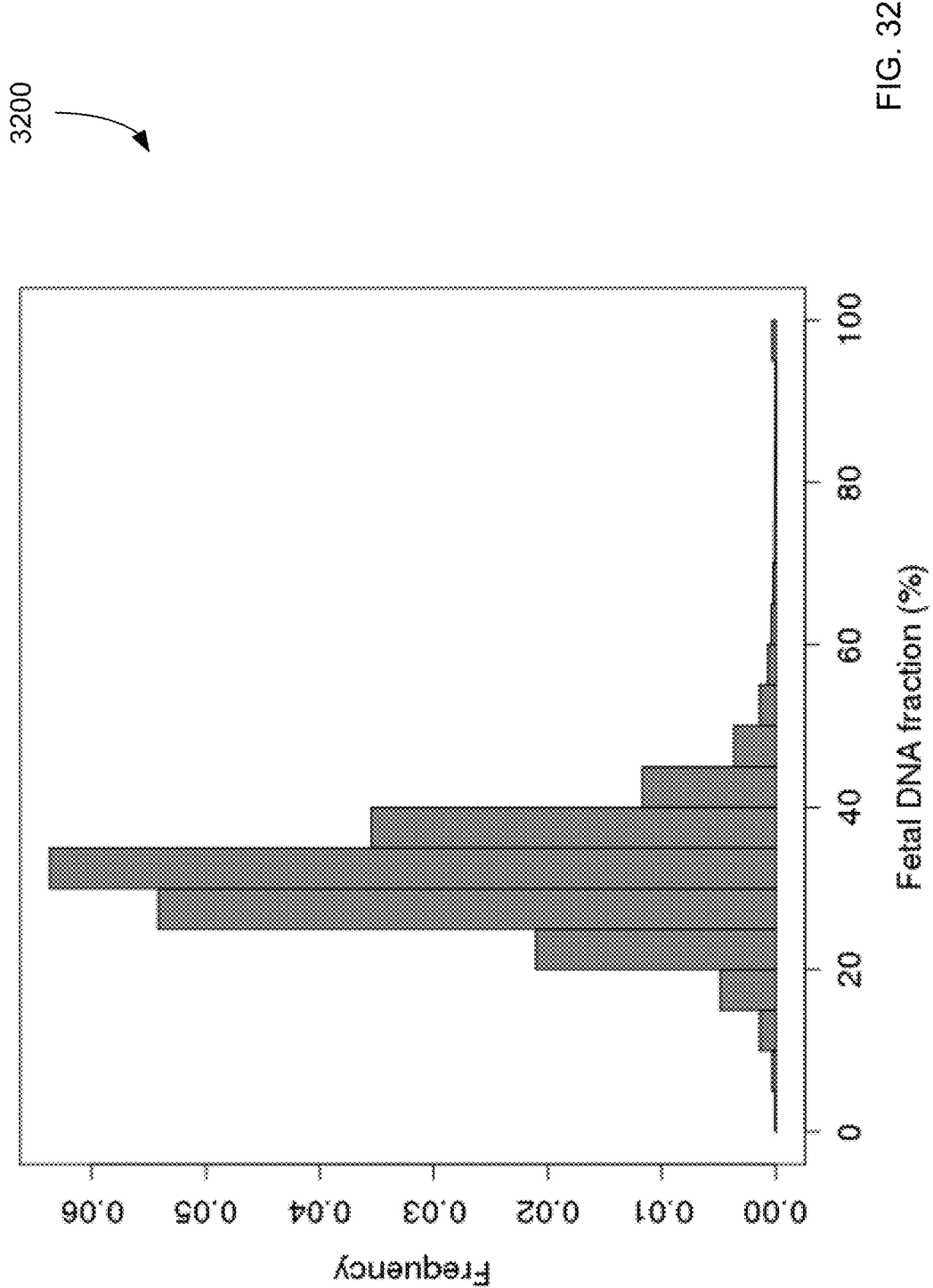
FIG. 32 shows the frequency distribution of the fetal fractions measured at individual SNP sites.

FIG. 32 shows the frequency distribution of the fetal fractions measured at such individual SNP sites. 95% of sites exhibit a fetal DNA fraction of higher than 20%.

Figure 33A:
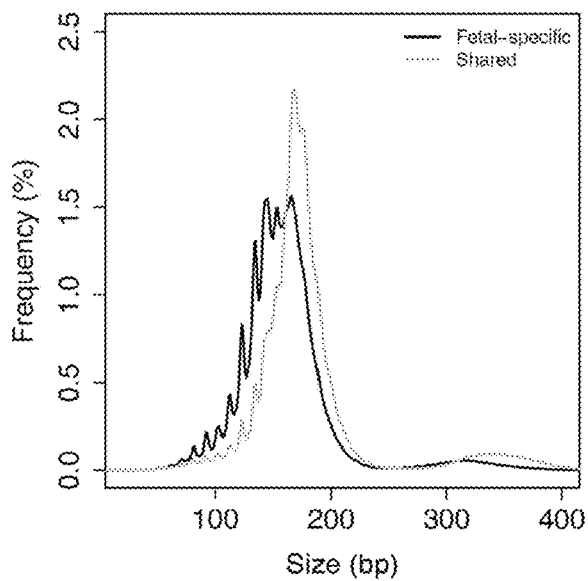
FIG. 33A shows a size distribution of fetal-specific DNA and shared DNA in maternal plasma.
Figure 33B:
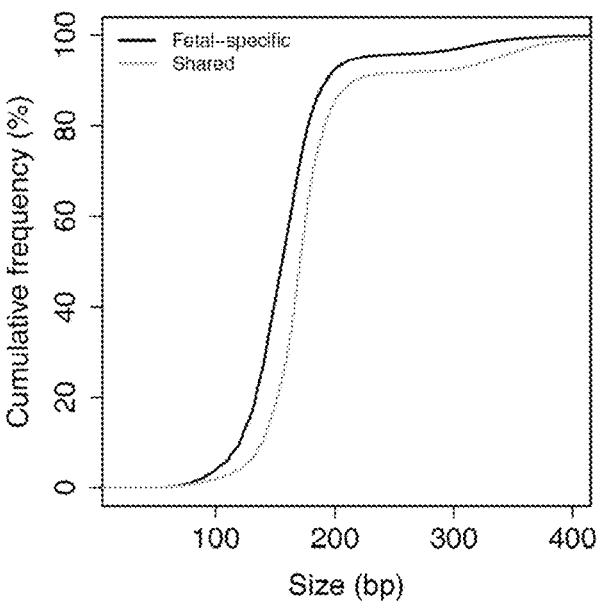
FIG. 33B shows a plot of cumulative frequencies for plasma DNA size for fetal specific and shared DNA fragment.
Figure 33C:
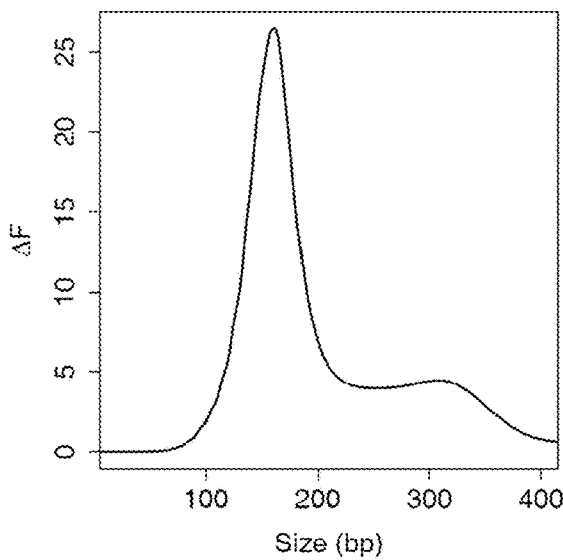
FIG. 33C shows the difference in cumulative frequencies, denoted as ΔF.

FIG. 33A shows a size distribution of fetal-specific DNA and shared DNA in maternal plasma. FIG. 33B shows a plot of cumulative frequencies for plasma DNA size for fetal specific and shared DNA fragment. FIG. 33C shows the difference in cumulative frequencies, denoted as $\Delta F$. Similar to previously reported observations (Lo et al. Sci Transl Med 2010; 2: 61ra91), the fetal DNA molecules in maternal plasma exhibit a shorter size than the non-fetal specific plasma DNA molecules.

To determine the de novo mutations present in the genome of this fetus, we looked for DNA variants, mostly point mutations or single nucleotide variants, that were present in both the placental DNA and cord blood DNA but not in the maternal genomic DNA and not in the paternal genomic DNA. Forty-seven such de novo mutant sites were identified. We then searched for DNA molecules that exhibited the de novo mutant allele in maternal plasma. We then studied the size distribution of the DNA molecules in maternal plasma.

Figure 34A:
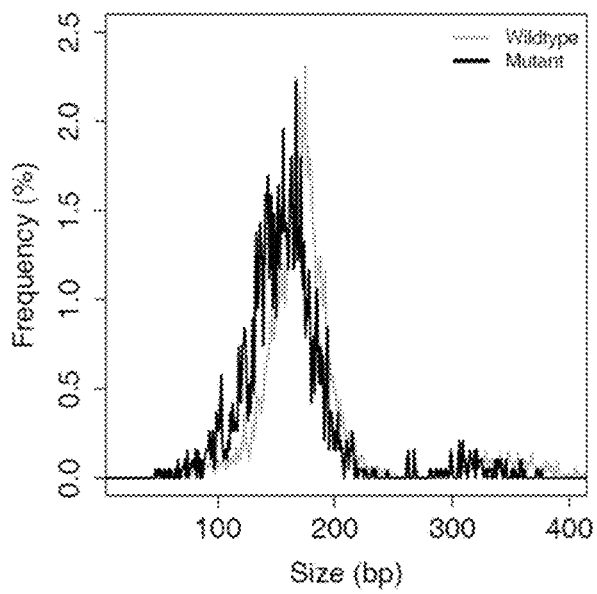
FIG. 34A shows the size distribution of plasma DNA fragments with the mutant allele.
Figure 34B:
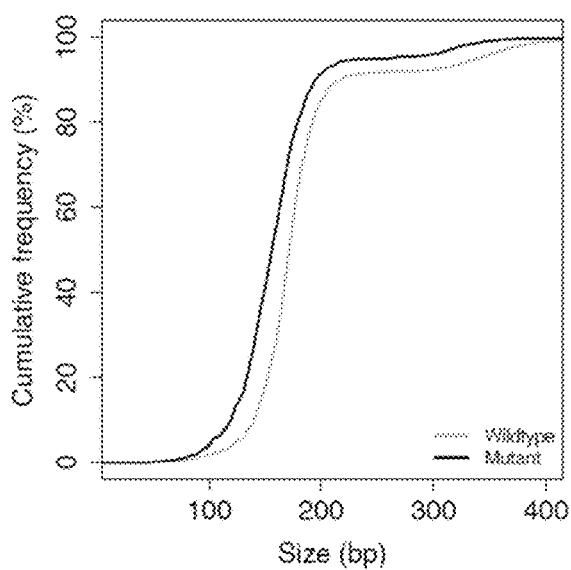
FIG. 34B shows a plot of cumulative frequencies for plasma DNA size for mutant allele and the wildtype allele.
Figure 34C:
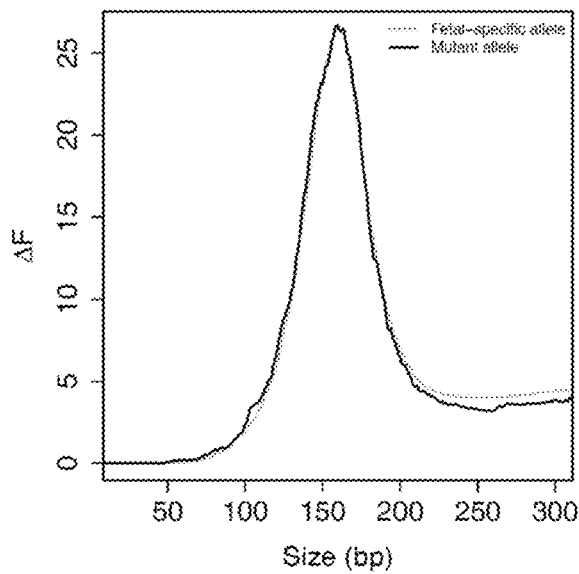
FIG. 34C shows the difference in cumulative frequencies, denoted as ΔF.

FIG. 34A shows the size distribution of plasma DNA fragments with the mutant allele. FIG. 34B shows a plot of cumulative frequencies for plasma DNA size for mutant allele and the wildtype allele. FIG. 34C shows the difference in cumulative frequencies, denoted as $\Delta F$. The size profiles and $\Delta F$ values of the mutant alleles showed a close resemblance to those values derived from fetal-specific alleles (FIGS. 33A-33C). Their relative short size in maternal plasma provides supportive evidence that those DNA molecules with the mutant allele are of fetal origin.

Next, we studied the effectiveness of our approach for identifying de novo mutations from maternal plasma DNA data. In this approach, we would need to obtain the maternal and paternal genomic sequence information. We then search for variants present among the maternal plasma DNA molecules but not in the maternal and paternal genomic DNA sequences.

FIG. 35 shows a filtering process 3500 (which uses dynamic cutoff, realignment, and mutation fraction, and size cutoff) and the resulting data for de novo mutations identified from plasma according to embodiments of the present invention. Filtering process 3500 can be used to identify the de novo mutations from maternal plasma cell-free DNA data. In this study, we used whole genome plasma DNA sequencing data generated using a PCR-free library preparation protocol.

First, we used a dynamic cutoff to screen the putative mutations in plasma. The dynamic cutoffs were used to control the theoretical occurrences of false positive in the human genome below a certain level, for example, once per genome. Two types of sources attributed to false positives can be taken into account in this dynamic cutoff model. One source would be the sequencing errors which by chance would cause some sites to show the same nucleotide change at the same position. The probability of this type of false positive can be estimated according to the multiplication rule of probability for a given sequencing error rate. The sequencing error can be deduced from sites where both the mother and father were homozygous and possessed the identical allele information. In this case, the sequencing error was estimated to be 0.3%. Another source would be heterozygous SNPs in the mother or the father which were miscalled as homozygous due to the under-sampling of alternative alleles.

Second, in order to further minimize the sequencing and alignment errors in the actual sequencing data, we applied an additional filtering algorithm. The sequencing reads carrying the mutations would be realigned (mapped) to human reference genome through the use of an independent aligner, for example Bowtie2 (Langmead et al. Nat Methods 2012; 9: 357-9). In some embodiments, the following realignment criteria can be used to identify a mapped read as a low-quality sequence read: (1) the sequence read carrying the mutation cannot be recovered by an independent aligner; (2) the sequence read carrying the mutation shows inconsistent mapping results when using an independent aligner to verify the original alignment (e.g., a mapped read is placed to a different chromosome compared to the original alignment result). (3) the sequence read carrying the mutation aligned to the same genomic coordinate exhibits a mapping quality $\leq Q20$ (i.e. misalignment probability <1%); (4) the sequence read has the mutation located within 5 bp of either read end (i.e. 5' or 3' ends). This last filtering rule can be important because sequencing errors are more prevalent occurring at both ends of a sequence read. If the proportion of low-quality sequence reads among the sequence reads carrying the mutation is greater than a certain threshold, for example, 40%, the candidate mutant sites will be discarded. This step of realignment of sequencing reads carrying the mutation is referred as Tier A filtering criteria.

Third, only the mutant fraction (M %) exceeding a certain threshold would be considered as a more likely true mutation, for example, 20% (tier B filtering criteria) and 30% (Tier C filtering criteria). The fetal DNA fraction estimated from informative SNPs can be used as a reference to set an appropriate threshold of mutant fraction.

Fourth, because the fetal-derived DNA molecules are shorter than those maternal-derived DNA molecules, we have further developed a size associated filtering parameter in the Tier D filtering criteria. A minimal difference in the median sizes between DNA fragments carrying mutant alleles and wildtype alleles is required to be at least a certain base pairs, denoted as $\Delta S$, for example, $\Delta S \geq 10$ bp. Other statistical tests can be also used, for example, the t-test, Mann-Whitney U test, Kolmogorov-Smirnov test, etc. We determined the recovery rates and positive predictive values (PPV) when applying each successive tiers of filtering. The recovery rate is based on the proportion of the 47 known de novo mutants detected after the filtering. The PPVs refer to the number of true de novo mutants detected as a proportion of all non-maternal and non-paternal variants detected in the maternal plasma cell-free DNA sequencing data. The fewer the false-positive de novo variants, the higher the PPV. The false-positives could occur as a result of, and not limited to, sequencing errors and alignment errors. The PPVs achieved by this approach is substantially better than that previously reported by Kitzman et al (Sci Transl Med 2012; 137: 137ra76). Sequencing a maternal plasma DNA library prepared using a non-PCR free protocol to 78× coverage has led to the identification of $2.5 \times 10^7$ false-positives while the true de novo mutations were only 44. The PPV of this study was only 0.000176%.

As a corroborative piece of evidence to show that the presumptive de novo variants or mutants detected are of fetal origin, we compared the size profiles of the de novo variants or mutants identified using the different tiers of filtering.

FIG. 36A shows size profiles of DNA fragments with the putative mutations identified in plasma using Tier A filtering criterion compared to wildtype allele. FIG. 36B shows size profiles of DNA fragments with the putative mutations identified in plasma using Tier B filtering criteria. FIG. 36C shows size profiles of DNA fragments with the putative mutations identified in plasma using Tier C filtering criteria. FIG. 36D shows size profiles of DNA fragments with the putative mutations identified in plasma using Tier D filtering criteria. As seen in FIGS. 36A-36D, the variants identified by the Tier D algorithm show the shortest size distribution.

Figure 37:
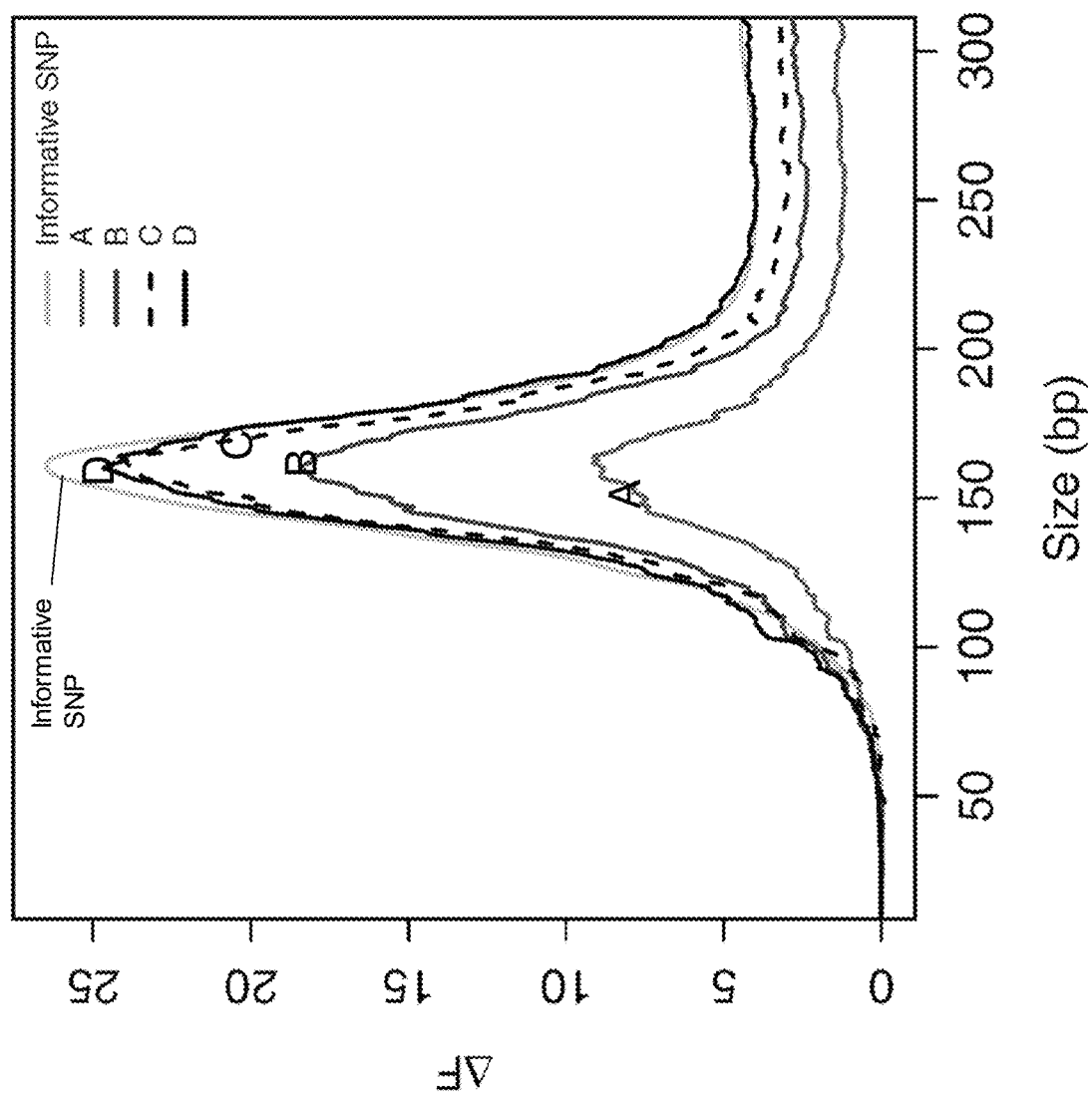
FIG. 37 shows the profiles of ΔF values corresponding to putative mutations identified using different tiers of filtering criteria, namely, A, B, C, and D.

FIG. 37 shows the profiles of ΔF values corresponding to putative mutations identified using different tiers of filtering criteria, namely, A, B, C, and D. ΔF values derived from 298,364 informative SNPs where both the mother and father were homozygous but with different alleles were used as a reference representing the difference in cumulative frequencies between fetal-derived and maternal-derived DNA fragments. The size profile deduced from Tier D filtering criteria turned out to most resemble the ΔF values deduced from informative SNP sites, suggesting that the putative de novo mutations identified in the criteria D had been enriched with more true mutations which were presented in the placenta/fetus.

Figure 38:
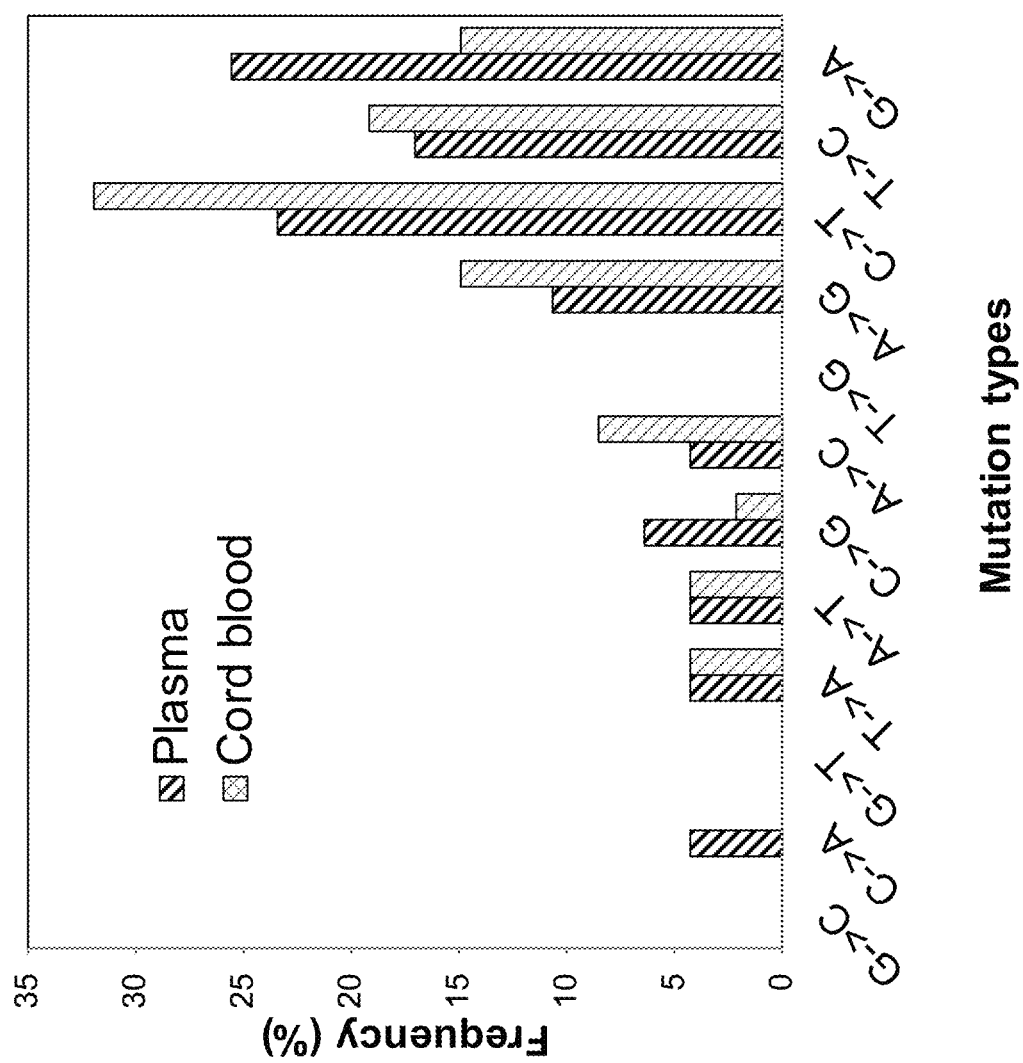
FIG. 38 shows a frequency count of various mutation types in a maternal plasma sample and cord blood.

FIG. 38 shows a frequency count of various mutation types in a maternal plasma sample and cord blood. In FIG. 38, the mutations identified in plasma are similar to those mutations mined in cord blood. These data suggest that the mutations detected in maternal plasma are present in the fetal genome as shown by the cord blood data.

Figure 39A:
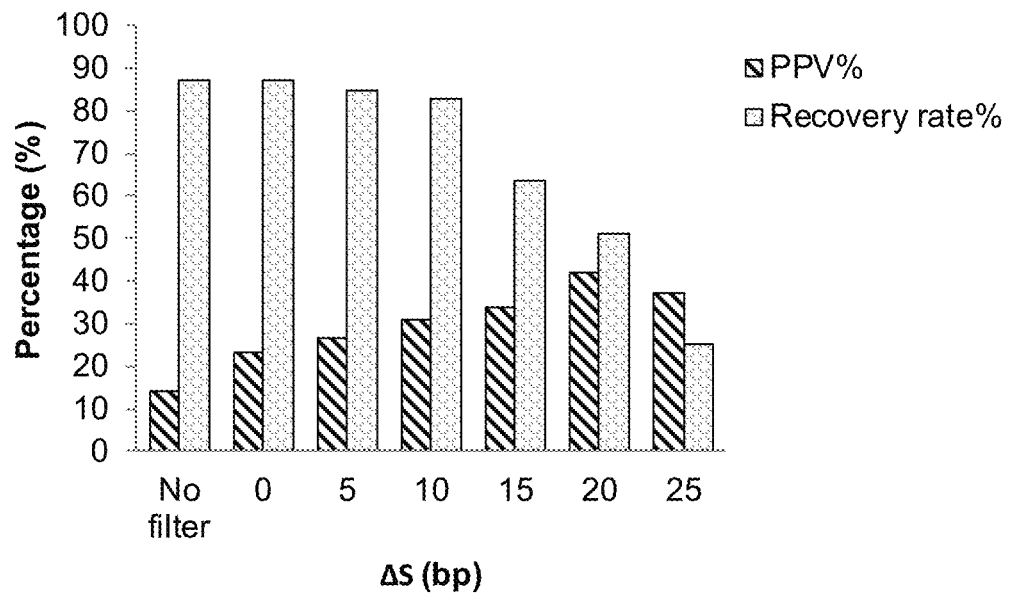
FIG. 39A shows a graph of PPV % and recovery rates for different size filters according to embodiments of the present invention.
Figure 39B:
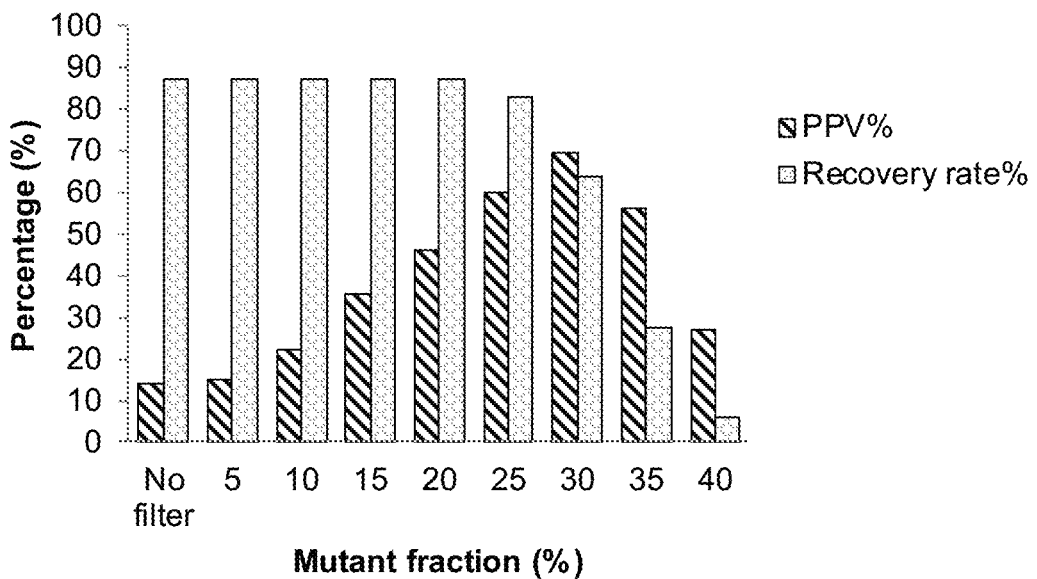
FIG. 39B shows a graph of PPV % and recovery rates for different mutant fraction cutoffs.

FIG. 39A shows a graph of PPV % and recovery rates for different size filters according to embodiments of the present invention. FIG. 39A shows how varying the size filtering parameter significantly affects the PPV % and recovery rate when no extra mutant fraction (M %) filtering was applied. FIG. 39B shows a graph of PPV % and recovery rates for different mutant fraction cutoffs. FIG. 39B shows that varying the mutant fraction parameter significantly affects the PPV % and recovery rate when no extra ΔS filtering is performed.

FIGS. 40A-40D show graphs of PPV % and recovery rates for various size filters at different mutant fraction cutoffs. Varying the size filtering parameter ΔS at different criteria of M % synergistically affects the PPV % and recovery rates.

Figure 41:
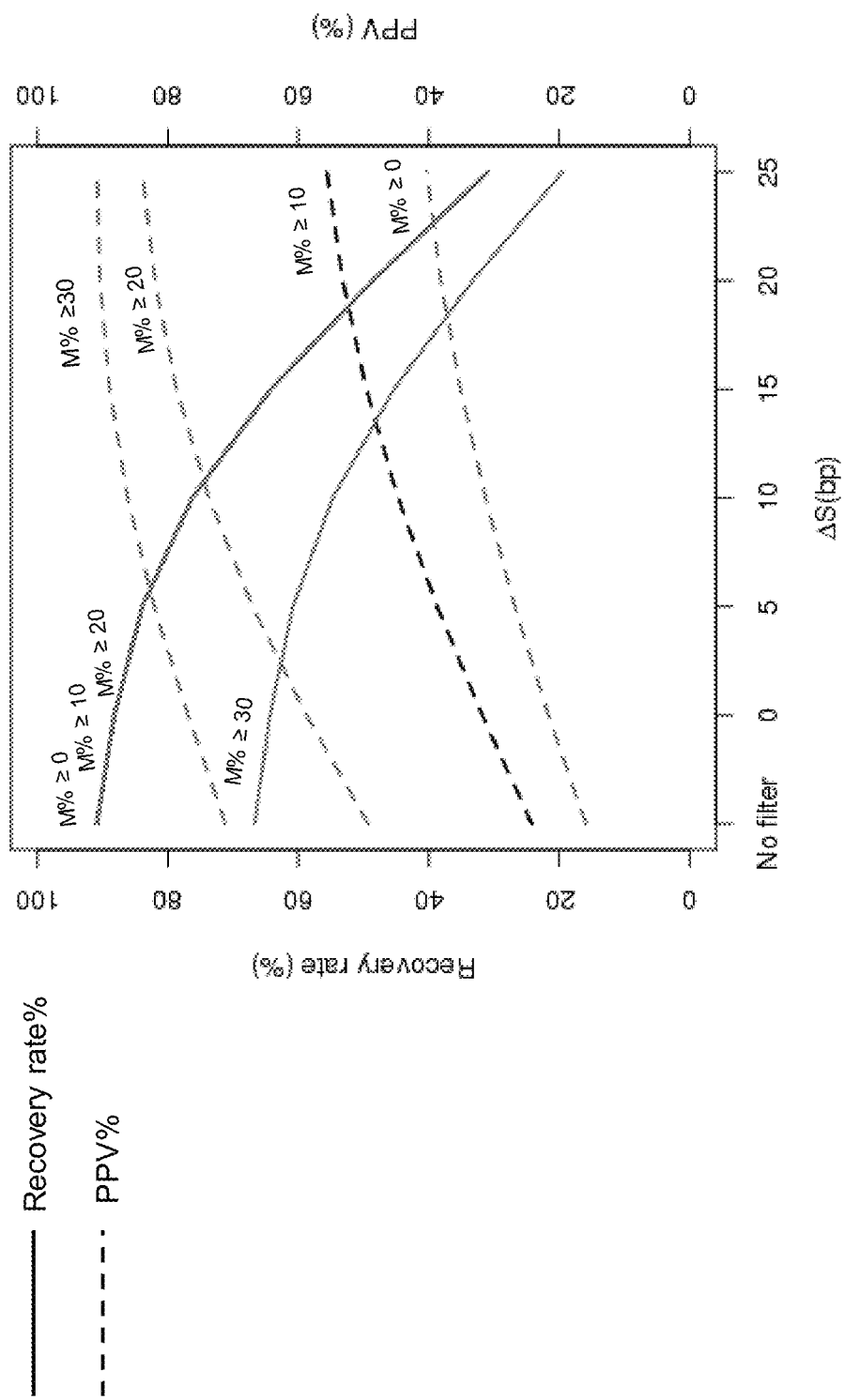
FIG. 41 is a plot showing curves of recovery rates and PPV % at different mutant fraction cutoffs as a function of size cutoffs.

FIG. 41 is a plot showing curves of recovery rates and PPV % at different mutant fraction cutoffs as a function of size cutoffs. Systematic plot revealing the interactions between ΔS, M % and PPV %, recovery rate.

C. Confirmation of the Putative De Novo Mutations

We aimed to confirm and validate the 47 de novo mutations. Primers were designed to specifically amplify each of the putative de novo mutations followed by Sanger sequencing of the paternal, maternal, placental and cord blood genomic DNA. The results are shown in Figure I, which shows next-generation sequencing (NGS) and Sanger sequencing analysis of the 48 putative de novo mutations. NGS refers to the massively parallel sequencing referred to above, and "Sanger seq" refers to Sanger sequencing. Allelic counts are shown in parentheses for clarification. One of these mutations (TP5) was detected in cord blood but not the placenta. Because fetal DNA molecules in maternal plasma mostly originate from placenta, the cord blood specific mutation would not be detectable in maternal plasma. Thus, only the remaining 47 placenta-derived mutations are relevant for the validation.

FIGS. 42 and 43 show a table of the 47 de novo mutations. In FIGS. 42 and 43, the chromosomal locations of the target mutation are shown in column 2. In column 3, the genotypes detected in maternal plasma are shown. The major allele is placed before the minor allele. In column 4, the ratios of reads showing the major allele to that of the minor allele at each of the mutation site are shown. In the subsequent columns, the results based on massively parallel sequencing or next-generation sequencing (NGS) are shown alongside the Sanger sequencing results. 43 of the 47 mutations were only detected in the placenta DNA but not in the paternal and maternal DNA. This meant that 91% of the mutations identified by maternal plasma DNA sequencing were indeed true de novo mutations, and thus the Sanger sequencing confirmed the NGS data for the plasma, maternal DNA, paternal DNA, placental DNA. The Sanger sequencing reactions for the detection of the mutation TP45 failed. Assays for the mutations TP21, TP30 and TP44 showed inconsistent results between NGS and Sanger sequencing.

VIII. Simulation Analysis for Cancer Mutation Detection from Cell-Free DNA in Human Plasma Using the sequencing data generated from the pregnant case, we selected 3,000 single nucleotide variants that the fetus had inherited from its father and assumed that they were somatic mutations developed by a cancer in a cancer patient. In other words, we analyzed the maternal plasma DNA sequencing data as if they were cell-free DNA sequencing from a plasma sample of a cancer patient. We then determined how many of the variants and false-positives would be detected if the plasma samples was only sequenced to 25×, 50× and 100× human genome coverage when the Tier D filtering algorithm was applied. 25×, 50× and 100×, respectively, of sequencing data were randomly selected among the 255× of plasma DNA sequencing data.

FIG. 44 shows the recovery rates and PPVs for the detection of the 47 de novo mutations and the 3,000 presumed somatic mutations. Tier D filtering algorithms for the numbers in Table 1 including: dynamic cutoffs, realignment, mutant fraction >20%, and size filter 10 bp.

We then performed more extensive analysis by computer simulation.

FIGS. 45A-45C and 46A-46C show simulations at varying amount of mutations for various sequencing depths and tumor fractions. In this set of analysis, we simulated the situations when we had plasma DNA sequencing depth ranging from 25× to 800×, with tumoral fraction concentrations ranging from 1% to 40% and when the number of somatic mutations developed by the tumor ranged from 3,000 to 30,000. All of the analyses are based on the Tier D filtering algorithm.

For each of these simulations, the number of somatic mutations detected as well as the number of false-positives are shown in FIGS. 45A-45C and 46A-46C. As shown in FIGS. 45A-45C and 46A-46C, many conditions would allow more somatic mutations detected than false-positives. These conditions would be clinically useful as a "mutation load test" to assess the burden of mutations present among the plasma DNA molecules. When this level is greater than a reference range, e.g. compared with age-matched and/or sex-matched controls, or compared with one's own blood cell DNA, cancer would be suspected. This approach would be using as a screening tool for the detection of cancer.

IX. Methods for Cancer

As described above, embodiments can provide methods for accurately identifying somatic mutations in a subject being tested. Various embodiments can use amplification-free sequencing, sequencing with minimal amplification (e.g., less than 2% duplication), and various filtering criteria. The identification mutations can be used to determine a level of cancer, as well as other purposes.

A. Identifying Mutations

Figure 47:
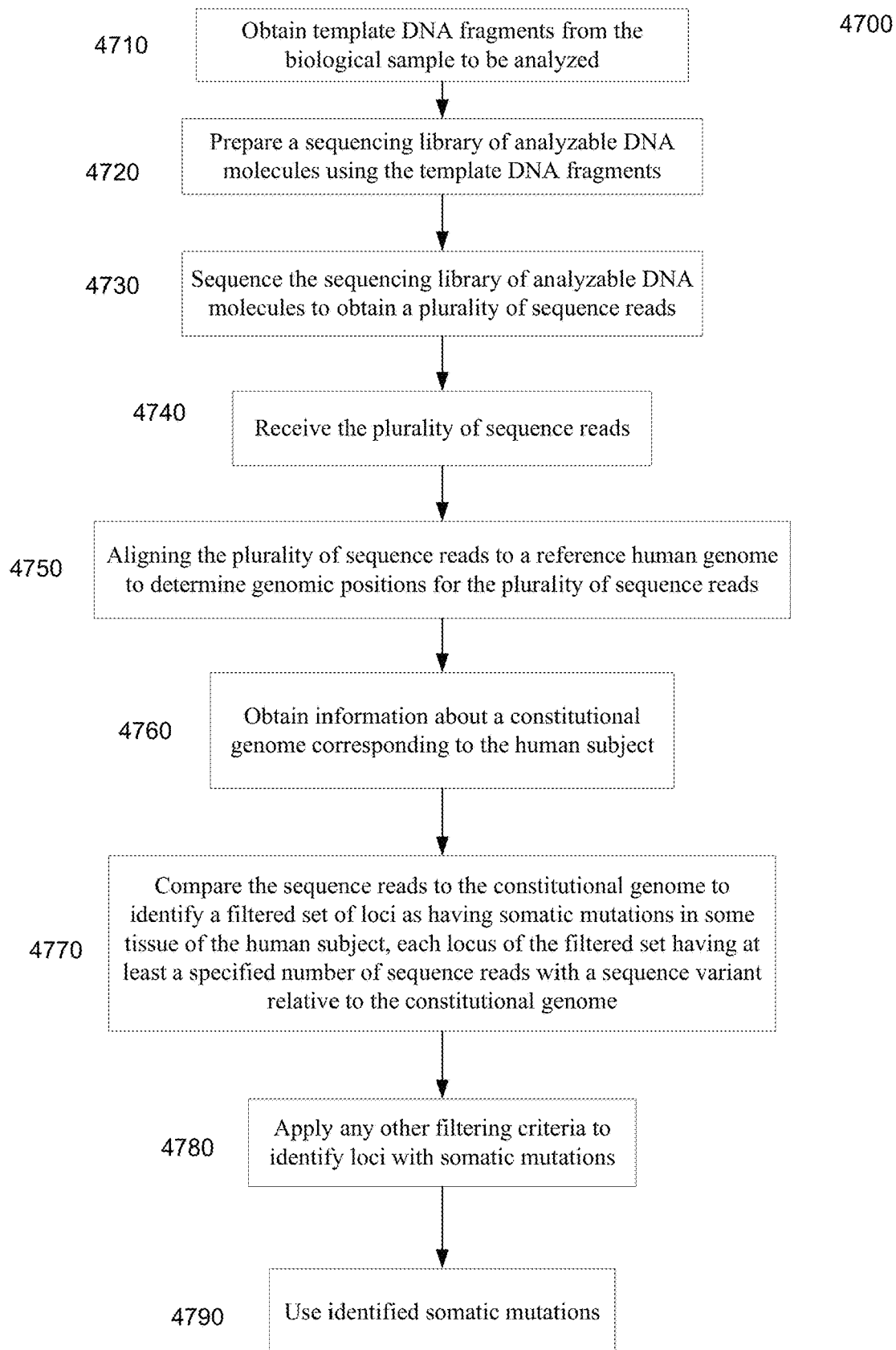
FIG. 47 is a flowchart illustrating a method 4700 for identifying somatic mutations in a human subject by analyzing a biological sample of the human subject according to embodiments of the present invention.

FIG. 47 is a flowchart illustrating a method 4700 for identifying somatic mutations in a human subject by analyzing a biological sample of the human subject according to embodiments of the present invention. The biological sample includes DNA fragments originating from normal cells and potentially from tumor cells or cells associated with cancer, and the biological sample includes cell-free DNA fragments. Method 4700 can be performed at least partially by a computer system, as can other methods described herein.

At block 4710, template DNA fragments are obtained from the biological sample to be analyzed. The template DNA fragments including cell-free DNA fragments. In various embodiments, cell-free DNA fragments from tumor cells or cells associated with cancer comprise less than 50%, 40%, 30%, 20%, 15%, 10%, 5%, or 1% of the cell-free DNA fragments in the biological sample. The biological sample can be plasma or serum, or other types of samples mentioned herein or that otherwise include cell-free DNA.

At block 4720, a sequencing library of analyzable DNA molecules is prepared using the template DNA fragments. In one embodiment, the preparation of the sequencing library of analyzable DNA molecules does not include a step of DNA amplification of the template DNA fragments. In another embodiment, some amplification can be performed such that some level of duplication does occur. But, the level of duplication can be minimal. In various implementations, a duplication rate of the sequencing library from the template DNA fragments is less than 5%, less than 2%, or less than 1%. The number of analyzable DNA molecules in the sequencing library can be less than the number of template DNA fragments originally present in the biological sample before library preparation.

At block 4730, the sequencing library of analyzable DNA molecules is sequenced to obtain a plurality of sequence reads. Various types of sequencing procedures can be used, as is described herein. Various depths and breadths can be used. As another example, single molecule sequencing may be performed. And, the sequencing can be methylation-aware sequencing.

At block 4740, the plurality of sequence reads are received at a computer system. The sequence reads can be received in any suitable manner or format, e.g., over a network from a sequencing machine or on a storage device. The data received from the sequencing machine may be raw intensity values that are used to determine base calls.

At block 4750, the computer can align the plurality of sequence reads to a reference human genome to determine genomic positions for the plurality of sequence reads. In various embodiments, sequencing depths of at least 30×, 35×, 40×, 50×, 75×, 100×, 150×, or 200× may be used. The aligned sequence reads may comprise various portions of the reference human genome, such as at least 0.1%, 1%, 5%, 10%, and 15% of the reference human genome.

At block 4760, the computer system can obtain information about a constitutional genome corresponding to the human subject. The constitutional genome can be that of the human subject or a reference genome that corresponds to the human subject. For example, the constitutional genome can be a reference genome for a specified population of human subjects.

At block 4770, the computer system can compare the sequence reads to the constitutional genome to identify a filtered set of loci as having somatic mutations in some tissue of the human subject. In one aspect, at each locus of the filtered set, a number of the sequence reads having a sequence variant relative to the constitutional genome is above a cutoff value, where the cutoff value is greater than one. The cutoff value can be a dynamic cutoff value as described herein. The cutoff value may be one filter criterion and others can be applied. The filtered set can be the final output after all of the filtering steps, potentially using various filtering criteria.

At block 4780, other filtering criteria can be used to identify the filtered set of loci as having somatic mutations in some tissue of the human subject. Such filtering criteria are described elsewhere and below.

At block 4790, the identified somatic mutations can be used for various purposes. Various examples of purposes are provided below. For example, a mutational load can be determined, and used to determine a level of cancer. The mutations can be used for designing further tests, potentially for further evaluation of a patient, and for determining treatment of a patient.

Examples of applying other filtering criteria are described below, as well as in other sections herein. The other filtering criteria can be used to identify the filtered set of loci as having somatic mutations in some tissue of the human subject. For some of the filtering criteria, a set of candidate loci identified as potentially having a somatic mutation can be analyzed. The candidate loci can have been identified using any suitable criteria, e.g., a fixed cutoff, a dynamic cutoff, or other previously-used filtering criteria. Thus, the resultant set of candidate loci can be the output of applying another filtering criterion.

1. Realignment

For realignment, each of a first set of candidate loci identified as potentially having a somatic mutation can be analyzed. Each of the sequence reads aligning to the candidate locus using a first alignment procedure and having the sequence variant can be further analyzed in a realignment procedure. It can be determined whether the sequence read aligns to the candidate locus using a second alignment procedure that uses a different matching algorithm than used for the first alignment procedure, e.g., as described in section V.B. When the sequence read realigns to the candidate locus using the second alignment procedure, a mapping quality of the realignment for the second alignment procedure can be determined.

Once the mapping quality for the second alignment is determined, the mapping quality can be compared to a quality threshold, so as to determine whether the sequence read is low quality. It can then be determined whether to discard the sequence read based on the comparing of the mapping quality to the quality threshold. The determination can be that reads below the threshold can be discarded. In other embodiments, a score (e.g., a weight) can be determined based on the comparison, where comparisons to multiple quality thresholds may be performed to determine the score, e.g., each threshold corresponding to a different realignment score. The score can then be used in a collective manner with scores from one or more other filtering criteria to determine whether to discard the read. Regardless of the specific manner (and inclusive of the examples provided above), the mapping quality being less than the quality threshold provides a higher likelihood of discarding the sequence read than the mapping quality being greater than the quality threshold.

As part of this filtering process, a number of remaining sequence reads are obtained. The number of remaining sequence reads can be compared to a candidate threshold, which can be the same threshold value originally used to identify candidate loci. In a similar likelihood analysis as for the sequence read, it can be determined whether to discard the candidate locus based on the comparing of the number of remaining sequence reads to the candidate threshold. The analysis can be strict based on the comparison to the threshold, or use a scoring (weighting) system as mentioned above. Regardless, the number of remaining sequence reads being less than the candidate threshold provides a higher likelihood of discarding the candidate locus than the number of remaining sequence reads being greater than the candidate threshold. The filtered set of loci can be identified as having somatic mutations using the remaining candidate loci.

2. Size

For a size analysis, each of a set of candidate loci can be analyzed. A size difference can be determined between a first group of DNA fragments having the sequence variant and a second group of DNA fragments having a wildtype allele. Such size analyses have been described herein. The size difference can be between any statistical value of size distributions for the two groups. For example, a difference in a median size of the first group of DNA fragments and the second group of DNA fragments can be used. As another example, a maximum in a cumulative frequency by size between the first group and the second group. Any size value described in U.S. Patent publications 2011/0276277 and 2013/0237431.

The size difference can be compared to a size threshold, which can be determined from samples known to have cancer or other status that is being classified. It can then be determined whether to discard the candidate locus as a potential mutation based on the comparison. As for other filtering criteria, the comparison can be used strictly or as a score. Regardless, the size difference being less than the size threshold provides a higher likelihood of discarding the candidate locus than the size difference being greater than the size threshold. The filtered set of loci can be identified as having somatic mutations in the human subject using the remaining candidate loci.

3. Histone Modifications

For histone modification, a group of regions known to be associated with histone modifications that are associated with cancer can be identified. Each of a set of candidate loci can be analyzed by determining whether to discard the candidate locus based on whether the candidate locus is in one of the group of regions. As for other filtering criteria, the comparison can be used strictly or as a score. Regardless, the candidate locus not being in one of the group of regions provides a higher likelihood of discarding the candidate locus than when the candidate locus is in one of the group of regions. The filtered set of loci can be identified as having somatic mutations in the human subject using the remaining candidate loci.

4. Mutant Fraction

For the mutant fraction, each of a set of candidate loci can be analyzed. A fraction of sequence reads having the sequence variant can be determined, and then compared to the fraction threshold. It can then be determined whether to discard the candidate locus as a potential mutation based on the comparison, e.g., using scores or strict cutoffs. Either way, the fraction being less than the fraction threshold provides a higher likelihood of discarding the candidate locus than the fraction being greater than the fraction threshold (e.g., 5%, 10%, 20%, or 30%). The filtered set of loci can be identified as having somatic mutations in the human subject using the remaining candidate loci.

In some embodiments, the fraction threshold can be determined based on a measured fractional concentration of tumor DNA in the biological sample. The fractional concentration of tumor DNA in the biological sample can be measured for each of a plurality of regions (e.g., using similar techniques but with data specific to one or more loci in the regions). The fraction threshold used for a candidate locus can be the fractional concentration measured for the region that the candidate locus resides.

In another embodiment, aberrant regions may be used to determine a fraction threshold. One or more aberrant regions that have a copy number aberration can be identified. The fraction threshold used for a candidate locus in an aberrant region can be dependent on whether the aberrant region exhibits a copy number gain or a copy number loss. A higher threshold may be used for a gain, and a lower threshold for a loss.

One or more aberrant regions that have a copy number aberration can also be used as part of determining whether to discard sequence reads for determining the number of the sequence reads having a sequence variant relative to the constitutional genome for each of the filtered set of loci. A first sequence read from a first aberrant region exhibiting a copy number gain is more likely to have a somatic mutation than a second sequence read from a second aberrant region exhibiting a copy number loss.

One or more aberrant regions can be identified by analyzing a set of candidate loci. An apparent mutant fraction of a sequence variant relative to the constitutional genome can be calculated. A variance in the apparent mutant fractions of the candidate loci in the aberrant region can be determined for each of a plurality of regions. The variance can be compared to a variance threshold, where an aberrant region exhibiting a copy number gain has a variance greater than the threshold.

5. Methylation Status

For methylation status, the sequencing is methylation-aware sequencing. Each of a set of candidate loci can be analyzed, with each of the sequence reads aligning to the candidate locus and having the sequence variant being analyzed. For a sequence read, a methylation status of the corresponding analyzable DNA molecule at one or more sites (e.g., CpG sites) can be determined. It can be determined whether to discard the sequence read based on the methylation status. As for other filtering criteria, the comparison can be used strictly or as a score. Regardless, the methylation status not being methylated provides a higher likelihood of discarding the sequence read than the methylation status being methylated.

The number of remaining sequence reads can be compared to a candidate threshold, which can be the same as used to identify the candidate loci (as is also true for other uses of a candidate threshold for other filtering criteria). In a similar likelihood analysis as for the sequence read, it can be determined whether to discard the candidate locus based on the comparing of the number of remaining sequence reads to the candidate threshold. The analysis can be strict based on the comparison to the threshold, or use a scoring (weighting) system as mentioned above. Regardless, the number of remaining sequence reads being less than the candidate threshold provides a higher likelihood of discarding the candidate locus than the number of remaining sequence reads being greater than the candidate threshold. The filtered set of loci can be identified as having somatic mutations using the remaining candidate loci.

6. Plasma DNA End Locations

For the plasma DNA end locations, each of a set of candidate loci can be analyzed, with each of the sequence reads aligning to the candidate locus and having the sequence variant being analyzed. For a sequence read, an end location corresponding to where an end of the sequence read aligns can be determined. The end location can be compared to a plurality of cancer-specific or cancer-associated terminal locations. Whether to discard the sequence read is determined based on the comparison. The end location not being a cancer-specific or cancer-associated terminal location provides a higher likelihood of discarding the sequence read than the end location being a cancer-specific or cancer-associated terminal location. The remaining number of sequence reads can be used to determine whether to discard the candidate locus.

7. Single-Stranded Sequencing

The sequencing can be performed using a single-stranded sequencing library preparation process that provides a subsequent sequencing step to yield two strand reads for each template DNA molecule. One example of a single-stranded sequencing library preparation process is described in Snyder et al. Cell 2016; 164: 57-68. Each of a set of candidate loci can be analyzed, with each pair of strand reads aligning to the candidate locus being analyzed. Whether both strands have the sequence variant can be determined. It can then be determined whether to discard the sequence read based on whether both strands have the sequence variant. Both strands not having the sequence variant provides a higher likelihood of discarding the strand reads than the only one strand read having the sequence variant. The remaining number of sequence reads can be used to determine whether to discard the candidate locus.

B. Determining Level of Cancer

Figure 48:
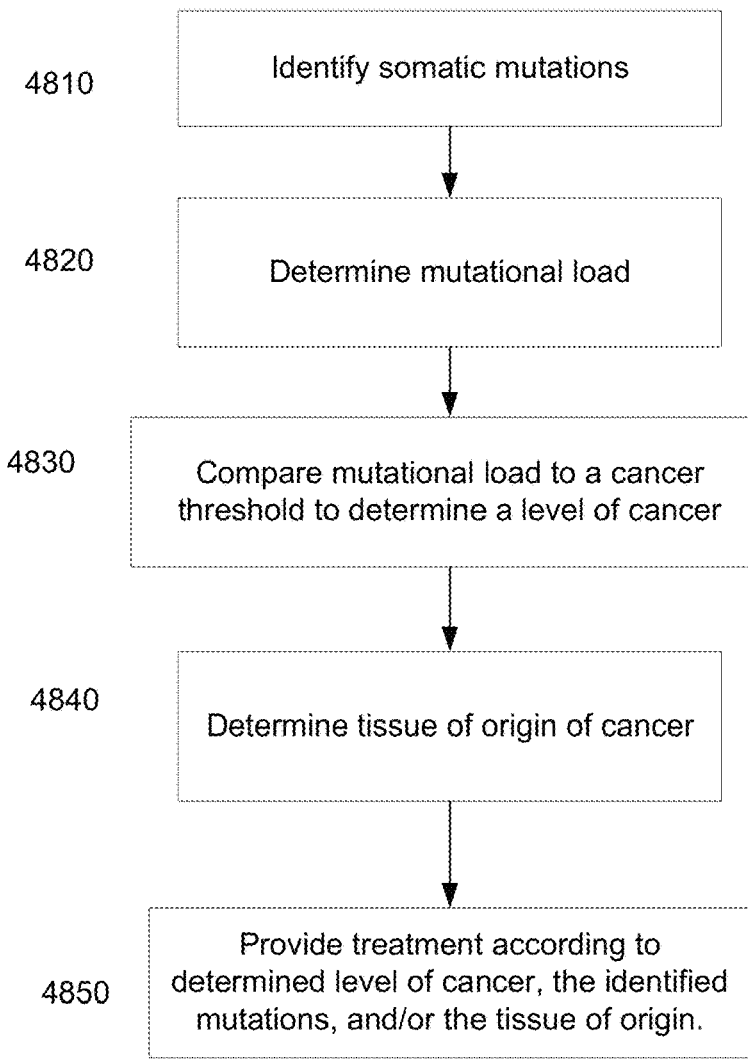
FIG. 48 is a flowchart illustrating a method 4800 for using identified somatic mutations to analyze biological sample of a subject according to embodiments of the present invention.

FIG. 48 is a flowchart illustrating a method 4800 for using identified somatic mutations to analyze a biological sample of a subject according to embodiments of the present invention.

At block 4810, the somatic mutations are identified. The somatic mutations may be identified as described for method 4700 of FIG. 47.

At block 4820, a mutational load for the human subject is determined using an amount of loci in the filtered set of loci. In various embodiments, the mutational load can be determined as a raw number of somatic mutations, a density of somatic mutations per number of bases, a percentage of loci of a genomic region that are identified as having somatic mutations, a number of somatic mutations observed in a particular amount of sample, or an increase compared with a reference load.

At block 4830, the mutational load is compared to a cancer threshold to determine a level of cancer. The cancer threshold can be determined based on a discrimination between cancer patients and subjects without cancer. One skilled in the art will appreciate that different thresholds can be used, depending on a desired sensitivity and specificity. As shown herein, embodiments can be used to determine a mutational load that can discriminate between a healthy subject and one with cancer, e.g., HCC.

At block 4840, when the level of cancer indicates the existence of a tumor, the tissue of origin of the cancer can be determined. As examples, such a determination can be made using methylation signatures or histone modifications or distribution of the end locations of the analyzed DNA fragments.

In one embodiment using histone modifications, a first amount of histone modifications is determined for each of a first plurality of segments of the reference human genome. This first amount can be determined from reference information available about which loci are associated with the relevant histone modifications. A second amount of the filtered set of loci can be determined for each of a second plurality of segments of the reference human genome. The difference segments can then be correlated to each other. Accordingly, a first set of segments having the first amount of histone modifications above a first threshold and having the second amount of the filtered set of loci above a second threshold can be determined. The two thresholds can be the same. The thresholds can ensure that the segments of the genome are those with high histone modifications and high number of somatic mutations. The amounts and thresholds can be raw numbers or densities (e.g., per megabase).

At block 4850, treatment can be provided according to determined level of cancer, the identified mutations, and/or the tissue of origin. For example, the identified mutations can be targeted with a particular drug or chemotherapy. The tissue of origin can be used to guide a surgery. And, the level of cancer can be used to determine how aggressive to be with any type of treatment, which may also be determined based on the level of cancer.

C. Other Uses for Identified Mutations

As mentioned above, the number of mutations can be used an indication that the tested subject has cancer. In one embodiment, an individual can be classified as having a high likelihood of having cancer if the number of mutations detected is higher than that detected in subjects without cancer.

The set of mutations once identified could be used to inform the design of more targeted assays (based on mutations represented in the mutational load) for future monitoring of the patient's cancer, for confirmation purposes, for more precise measurement purposes, or for serial measurement purpose (which would be cheaper than repeating exhaustive sequencing multiple times). Such serial measurements would be useful for follow-up purposes, e.g. to see if the concentration of the mutational signature in plasma is increasing (potentially a bad prognostic sign) or decreasing (potentially a good prognostic sign or that the cancer is responsive to the chosen treatment).

Specific mutations detected in the mutational load would provide information for clinicians to choose the relevant therapy or drug, e.g. targeted therapy. As an example, one can use tyrosine kinase inhibitors for treating cancers with specific mutations in the epidermal growth factor receptor gene.

The spectrum of mutations identified can be used to help identify the site of the tumor because tumors developed from different organs/tissues have been found to have different mutational profiles (Polak et al. Nature 2015; 518: 360-364). It could also provide information about the environmental exposure and carcinogens that are causally linked to the set of mutations detected (Alexandrov et al. Nature 2013; 500: 415-421). The spectrum of mutations identified can be used to help for prognostication. For example, some mutations may be markers of cancers that are particularly aggressive or indolent.

In the context of prenatal testing, the set of mutations identified could be used to inform the design of more targeted assays (based on mutations represented in the mutational load) for the specific detection of such mutations in maternal plasma. Also, in the context of prenatal testing, the set of mutations identified could be used to inform the clinicians of the need for special clinical management of the case. As one example, the detection of sporadic hemophilia mutation in a male fetus could indicate the need for precaution during the delivery procedure (e.g. avoidance of forceps delivery) should the pregnant woman choose to continue with the pregnancy to term. As another example, the detection of a female fetus who is homozygous or compound heterozygous for mutations for congenital adrenal hyperplasia (CAH) in a family with no previous family history of CAH would alert the clinician to the need for early dexamethasone therapy of the pregnant woman, so as to reduce the risk of virilization of the fetal genitalia.

X. Methods for Fetal Analysis

Figure 49:
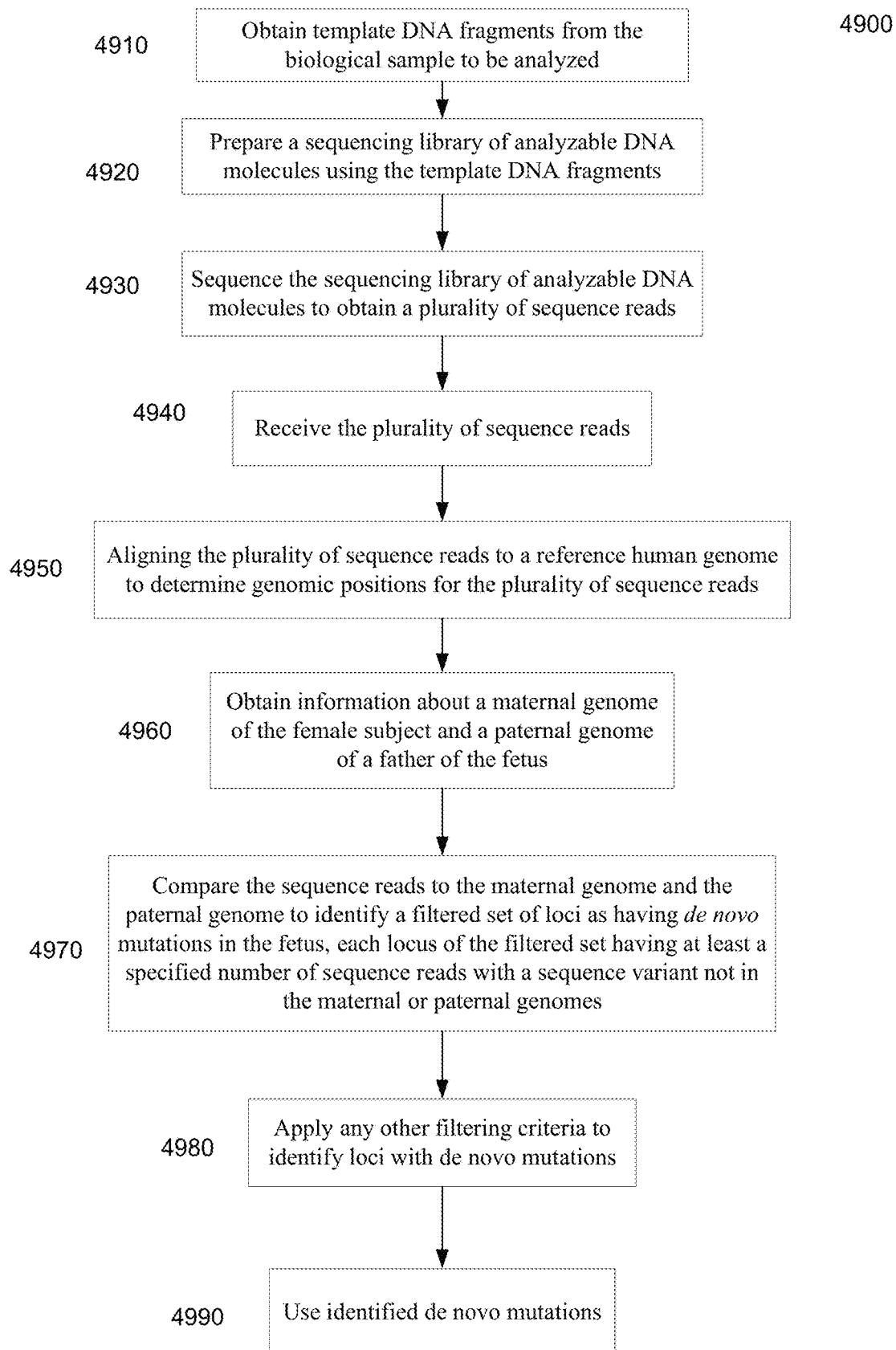
FIG. 49 is a flowchart illustrating a method 4900 for identifying de novo mutations of a fetus by analyzing a biological sample of a female subject pregnant with the fetus according to embodiments of the present invention.

FIG. 49 is a flowchart illustrating a method 4900 for identifying de novo mutations of a fetus by analyzing a biological sample of a female subject pregnant with the fetus according to embodiments of the present invention. The biological sample includes cell-free DNA fragments from the fetus and the female subject.

At block 4910, template DNA fragments are obtained from the biological sample to be analyzed. The template DNA fragments including cell-free DNA fragments. Block 4910 can be performed in a similar manner as block 4710 of FIG. 47.

At block 4920, a sequencing library of analyzable DNA molecules is prepared using the template DNA fragments. Block 4920 can be performed in a similar manner as block 4720 of FIG. 47.

At block 4930, the sequencing library of analyzable DNA molecules is sequenced to obtain a plurality of sequence reads. Block 4930 can be performed in a similar manner as block 4730 of FIG. 47.

At block 4940, the plurality of sequence reads are received at a computer system. Block 4940 can be performed in a similar manner as block 4740 of FIG. 47.

At block 4950, the computer can align the plurality of sequence reads to a reference human genome to determine genomic positions for the plurality of sequence reads. Block 4950 can be performed in a similar manner as block 4750 of FIG. 47.

At block 4960, the computer system can obtain information about a maternal genome of the female subject and a paternal genome of a father of the fetus. The information can include genotype information about both parents at the loci examined for existence of a mutation. Such genotype information can be obtained via any suitable techniques as would be known by one skilled in the art.

At block 4970, the computer system can compare the sequence reads to the maternal genome and the paternal genome to identify a filtered set of loci as having de novo mutations in the fetus. In one aspect, at each locus of the filtered set, a number of the sequence reads having a sequence variant not in the maternal genome and not in the paternal genome is above a cutoff value, where the cutoff value is greater than one.

At block 4980, other filtering criteria can be used to identify the filtered set of loci as having de novo mutations in the fetus. Such filtering criteria are described elsewhere, e.g., in section IX.

At block 4990, the identified de novo mutations can be used for various purposes. Examples of such purposes can be found in section IX.C.

XI. Computer System

Figure 50:
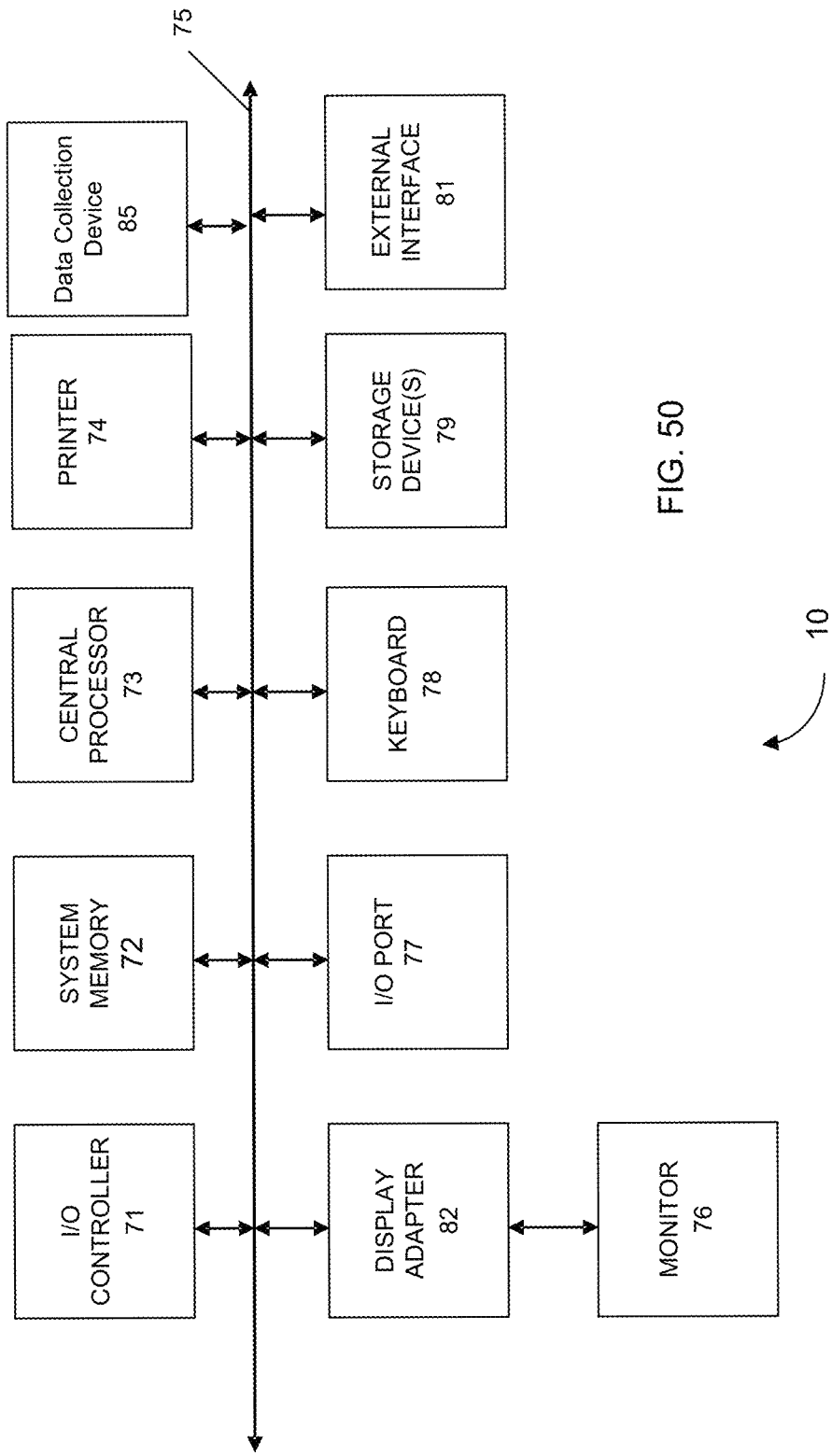
FIG. 50 shows a block diagram of an example computer system 10 usable with system and methods according to embodiments of the present invention.

Any of the computer systems mentioned herein may utilize any suitable number of subsystems. Examples of such subsystems are shown in FIG. 50 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 50 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method for identifying somatic mutations in a human subject by analyzing a biological sample of the human subject, the biological sample including DNA fragments originating from normal cells and potentially from tumor cells or cells associated with cancer, the biological sample including cell-free DNA fragments, the method comprising, performing, by a computer system:
   obtaining information about a constitutional genome corresponding to the human subject; and
   receiving one or more sequence reads for each of a plurality of DNA fragments in the biological sample, thereby obtaining a plurality of sequence reads;
   aligning the plurality of sequence reads to a reference human genome using a first alignment procedure to determine genomic positions for the plurality of sequence reads;
   comparing the sequence reads to the constitutional genome as part of identifying a filtered set of loci as having somatic mutations in some tissue of the human subject, wherein:
      at each locus of the filtered set of loci, a number of the sequence reads having a sequence variant relative to the constitutional genome is above a cutoff value, the cutoff value being greater than one;
   for each candidate locus of a first set of candidate loci identified as potentially having a somatic mutation:
      determining a size difference between a first group of DNA fragments having the sequence variant and a second group of DNA fragments having a wildtype allele;
      comparing the size difference to a size threshold;
      when the size difference is less than the size threshold, discarding the candidate locus as a potential mutation; and
   further identifying the filtered set of loci as having somatic mutations in the human subject using the remaining candidate loci.

2. The method of claim 1, wherein the size difference is a difference in a median size of the first group of DNA fragments and the second group of DNA fragments.

3. The method of claim 1, wherein the size difference is a maximum in a cumulative frequency by size between the first group of DNA fragments and the second group of DNA fragments.

4. The method of claim 1, wherein identifying the filtered set of loci as having somatic mutations in some tissue of the human subject further includes:
   for each candidate locus of a second set of candidate loci identified as potentially having a somatic mutation:
      for each sequence read of the sequence reads aligning to the candidate locus using the first alignment procedure and having the sequence variant:
         determining whether the sequence read aligns to the candidate locus using a second alignment procedure that uses a different matching algorithm than that used for the first alignment procedure;
         when the sequence read realigns to the candidate locus using the second alignment procedure, determining a mapping quality of the realignment for the second alignment procedure;
         comparing the mapping quality to a quality threshold; and
         determining whether to discard the sequence read based on the comparing of the mapping quality to the quality threshold, wherein the mapping quality being less than the quality threshold provides a higher likelihood of discarding the sequence read than the mapping quality being greater than the quality threshold, thereby obtaining a number of remaining sequence reads;
      comparing the number of remaining sequence reads to a candidate threshold; and
      determining whether to discard the candidate locus based on the comparing of the number of remaining sequence reads to the candidate threshold, wherein the number of remaining sequence reads being less than the candidate threshold provides a higher likelihood of discarding the candidate locus than the number of remaining sequence reads being greater than the candidate threshold; and
   identifying the filtered set of loci as having somatic mutations using the remaining candidate loci.

5. The method of claim 1, wherein identifying the filtered set of loci as having somatic mutations in some tissue of the human subject further includes:
   identifying a group of regions known to be associated with histone modifications that are associated with cancer;
   for each candidate locus of a second set of candidate loci identified as potentially having a somatic mutation:
      determining whether the candidate locus is in one of the group of regions;

determining whether to discard the candidate locus based on whether the candidate locus is in one of the group of regions, wherein the candidate locus not being in one of the group of regions provides a higher likelihood of discarding the candidate locus than when the candidate locus is in one of the group of regions; and identifying the filtered set of loci as having somatic mutations using the remaining candidate loci.

6. The method of claim 1, further comprising:
determining a mutational load for the human subject using an amount of loci in the filtered set of loci.

7. The method of claim 6, wherein the mutational load is determined as
a raw number of somatic mutations, a density of somatic mutations per number of bases, a percentage of loci of a genomic region that are identified as having somatic mutations, a number of somatic mutations observed in a particular amount of sample, or an increase compared with a reference load.

8. The method of claim 6, further comprising:
comparing the mutational load to a cancer threshold to determine a level of cancer.

9. The method of claim 8, wherein the level of cancer indicates a tumor, further comprising:
determining a first amount of histone modifications for each of a first plurality of segments of the reference human genome;
determining a second amount of the filtered set of loci for each of a second plurality of segments of the reference human genome;
determining a first set of segments having the first amount of histone modifications above a first threshold and having the second amount of the filtered set of loci above a second threshold; and
identifying a tissue of origin of the tumor based on the first set of segments.

10. The method of claim 1, wherein identifying the filtered set of loci as having somatic mutations in some tissue of the human subject further includes:
for each candidate locus of a second set of candidate loci identified as potentially having a somatic mutation:
determining a fraction of sequence reads having the sequence variant;
comparing the fraction to a fraction threshold;
determining whether to discard the candidate locus as a potential mutation based on the comparison, wherein the fraction being less than the fraction threshold provides a higher likelihood of discarding the candidate locus than the fraction being greater than the fraction threshold; and
identifying the filtered set of loci as having somatic mutations in the human subject using the remaining candidate loci.

11. The method of claim 10, wherein the fraction threshold is at least 20%.

12. The method of claim 10, further comprising:
measuring a fractional concentration of tumor DNA in the biological sample, wherein the fraction threshold is determined based on the fractional concentration of tumor DNA.

13. The method of claim 12, wherein the fractional concentration of tumor DNA in the biological sample is measured for each region of a plurality of regions, and wherein the fraction threshold used for a candidate locus is dependent on the fractional concentration of tumor DNA measured for the region in which the candidate locus resides.

14. The method of claim 10, further comprising:
identifying one or more aberrant regions that have a copy number aberration, wherein the fraction threshold used for a candidate locus in an aberrant region is dependent on whether the aberrant region exhibits a copy number gain or a copy number loss.

15. The method of claim 10, further comprising:
identifying one or more aberrant regions that have a copy number aberration; and
identifying a first sequence read from a first aberrant region exhibiting a copy number gain to be more likely to have a somatic mutation than a second sequence read from a second aberrant region exhibiting a copy number loss as part of determining whether to discard sequence reads for determining the number of the sequence reads having a sequence variant relative to the constitutional genome for each locus of the filtered set of loci.

16. The method of claim 15, wherein the one or more aberrant regions are identified by:
for each candidate locus of the second set of candidate loci identified as potentially having a somatic mutation:
calculating an apparent mutant fraction of a sequence variant relative to the constitutional genome;
for each region of a plurality of regions:
determining a variance in the apparent mutant fractions of the candidate loci in the region; and
comparing the variance to a variance threshold, where an aberrant region exhibiting a copy number gain has the variance greater than the variance threshold.

17. The method of claim 1, wherein the plurality of sequence reads are obtained using methylation-aware sequencing, and wherein identifying the filtered set of loci as having somatic mutations in some tissue of the human subject further includes:
for each candidate locus of a second set of candidate loci identified as potentially having a somatic mutation:
for each sequence read of the sequence reads aligning to the candidate locus and having the sequence variant:
determining a methylation status of the corresponding analyzable DNA molecule at one or more sites;
determining whether to discard the sequence read based on the methylation status, wherein the methylation status not being methylated provides a higher likelihood of discarding the sequence read than the methylation status being methylated, thereby obtaining a number of remaining sequence reads;
comparing the number of remaining sequence reads to a candidate threshold; and
determining whether to discard the candidate locus based on the comparing of the number of remaining sequence reads to the candidate threshold, wherein the number of remaining sequence reads being less than the candidate threshold provides a higher likelihood of discarding the candidate locus than the number of remaining sequence reads being greater than the candidate threshold; and
identifying the filtered set of loci as having somatic mutations using the remaining candidate loci.

18. The method of claim 1, wherein identifying the filtered set of loci as having somatic mutations in some tissue of the human subject further includes:
for each candidate locus of a second set of candidate loci identified as potentially having a somatic mutation:

for each sequence read of the sequence reads aligning to the candidate locus and having the sequence variant:
  determining an end location corresponding to where an end of the sequence read aligns;
  comparing the end location to a plurality of cancer-specific or cancer-associated terminal locations;
  determining whether to discard the sequence read based on the comparison, wherein the end location not being one of the plurality of cancer-specific or cancer-associated terminal locations provides a higher likelihood of discarding the sequence read than the end location being one of the plurality of cancer-specific or cancer-associated terminal locations, thereby obtaining a number of remaining sequence reads;
comparing the number of remaining sequence reads to a candidate threshold; and
determining whether to discard the candidate locus based on the comparing of the number of remaining sequence reads to the candidate threshold, wherein the number of remaining sequence reads being less than the candidate threshold provides a higher likelihood of discarding the candidate locus than the number of remaining sequence reads being greater than the candidate threshold; and
identifying the filtered set of loci as having somatic mutations using the remaining candidate loci.

19. The method of claim 1, wherein the plurality of sequence reads are obtained using methylation-aware sequencing using a single-stranded sequencing library preparation process that provides a subsequent sequencing step to yield two strand reads for each template DNA molecule, wherein identifying the filtered set of loci as having somatic mutations in some tissue of the human subject further includes:
  for each candidate locus of a second set of candidate loci identified as potentially having a somatic mutation:
    for each pair of strand reads aligning to the candidate locus:
      determining whether both strands have the sequence variant;
      determining whether to discard the sequence read based on whether both strands have the sequence variant, wherein both strands not having the sequence variant provides a higher likelihood of discarding the strand reads than only one strand read having the sequence variant, thereby obtaining a number of remaining sequence reads;
    comparing the number of remaining sequence reads to a candidate threshold; and
    determining whether to discard the candidate locus based on the comparing of the number of remaining sequence reads to the candidate threshold, wherein the number of remaining sequence reads being less than the candidate threshold provides a higher likelihood of discarding the candidate locus than the number of remaining sequence reads being greater than the candidate threshold; and
  identifying the filtered set of loci as having somatic mutations using the remaining candidate loci.

20. The method of claim 1, wherein the constitutional genome corresponding to the human subject is a reference genome for a specified population of human subjects.

21. The method of claim 1, wherein cell-free DNA fragments from tumor cells or cells associated with cancer comprise less than 50% of the cell-free DNA fragments in the biological sample.

22. The method of claim 1, wherein the biological sample includes plasma or serum.

23. The method of claim 1, wherein the sequence reads that align to the reference human genome comprise at least 5% of the reference human genome.

24. The method of claim 23 wherein the sequence reads that align to the reference human genome comprise at least 10% of the reference human genome.

25. The method of claim 1, wherein a sequencing depth of at least 25× is used.

26. A computer product comprising a non-transitory computer readable medium storing a plurality of instructions for controlling a computer system to perform a method for identifying somatic mutations in a human subject by analyzing a biological sample of the human subject, the biological sample including DNA fragments originating from normal cells and potentially from tumor cells or cells associated with cancer, the biological sample including cell-free DNA fragments, the method comprising:
  obtaining information about a constitutional genome corresponding to the human subject; and
  receiving one or more sequence reads for each of a plurality of DNA fragments in the biological sample, thereby obtaining a plurality of sequence reads;
  aligning the plurality of sequence reads to a reference human genome using a first alignment procedure to determine genomic positions for the plurality of sequence reads;
  comparing the sequence reads to the constitutional genome as part of identifying a filtered set of loci as having somatic mutations in some tissue of the human subject, wherein:
    at each locus of the filtered set of loci, a number of the sequence reads having a sequence variant relative to the constitutional genome is above a cutoff value, the cutoff value being greater than one;
  for each candidate locus of a first set of candidate loci identified as potentially having a somatic mutation:
    determining a size difference between a first group of DNA fragments having the sequence variant and a second group of DNA fragments having a wildtype allele;
    comparing the size difference to a size threshold;
    when the size difference is less than the size threshold, discarding the candidate locus as a potential mutation; and
  further identifying the filtered set of loci as having somatic mutations in the human subject using the remaining candidate loci.

27. A method for identifying somatic mutations in a human subject by analyzing a biological sample of the human subject, the biological sample including DNA fragments originating from normal cells and potentially from tumor cells or cells associated with cancer, the biological sample including cell-free DNA fragments, the method comprising, performing, by a computer system:
  obtaining information about a constitutional genome corresponding to the human subject; and
  receiving one or more sequence reads for each of a plurality of DNA fragments in the biological sample, thereby obtaining a plurality of sequence reads;

aligning the plurality of sequence reads to a reference human genome using a first alignment procedure to determine genomic positions for the plurality of sequence reads;

comparing the sequence reads to the constitutional genome as part of identifying a filtered set of loci as having somatic mutations in some tissue of the human subject, wherein:

at each locus of the filtered set of loci, a number of the sequence reads having a sequence variant relative to the constitutional genome is above a cutoff value, the cutoff value being greater than one;

identifying a group of regions known to be associated with histone modifications that are associated with cancer;

for each candidate locus of a set of candidate loci identified as potentially having a somatic mutation:

determining whether the candidate locus is in one of the group of regions;

determining whether to discard the candidate locus based on whether the candidate locus is in one of the group of regions, wherein the candidate locus not being in one of the group of regions provides a higher likelihood of discarding the candidate locus than when the candidate locus is in one of the group of regions; and further identifying the filtered set of loci as having somatic mutations using the remaining candidate loci.

* * * * *